US011471118B2

(12) United States Patent
Williams

(10) Patent No.: US 11,471,118 B2
(45) Date of Patent: Oct. 18, 2022

(54) SYSTEM AND METHOD FOR TRACKING X-RAY TUBE FOCAL SPOT POSITION

(71) Applicant: Hologic, Inc., Marlborough, MA (US)

(72) Inventor: Cornell Lee Williams, North East, MD (US)

(73) Assignee: Hologic, Inc., Marlborough, MA (US)

( * ) Notice: Subject to any disclaimer, the term of this patent is extended or adjusted under 35 U.S.C. 154(b) by 31 days.

(21) Appl. No.: 17/211,660

(22) Filed: Mar. 24, 2021

(65) Prior Publication Data

US 2021/0298700 A1    Sep. 30, 2021

Related U.S. Application Data

(60) Provisional application No. 63/000,996, filed on Mar. 27, 2020.

(51) Int. Cl.
*A61B 6/00* (2006.01)
*H05G 1/52* (2006.01)

(52) U.S. Cl.
CPC .......... *A61B 6/4021* (2013.01); *A61B 6/5205* (2013.01); *A61B 6/583* (2013.01); *A61B 6/587* (2013.01); *H05G 1/52* (2013.01)

(58) Field of Classification Search
CPC ..... A61B 6/4021; A61B 6/5205; A61B 6/583; A61B 6/587; H05G 1/52
See application file for complete search history.

(56) References Cited

U.S. PATENT DOCUMENTS

| | | | |
|---|---|---|---|
| 3,365,575 | A | 1/1968 | Strax |
| 3,502,878 | A | 3/1970 | Stewart |
| 3,863,073 | A | 1/1975 | Wagner |
| 3,971,950 | A | 7/1976 | Evans et al. |

(Continued)

FOREIGN PATENT DOCUMENTS

| | | |
|---|---|---|
| CN | 108492874 | 9/2018 |
| DE | 4104166 | 8/1992 |

(Continued)

OTHER PUBLICATIONS

European Extended Search Report in Application 21165189.8, dated Aug. 20, 2021, 7 pages.

(Continued)

*Primary Examiner* — Chih-Cheng Kao
(74) *Attorney, Agent, or Firm* — Merchant & Gould P.C.

(57) ABSTRACT

Methods and devices for tracking an x-ray tube focal spot position are described. As successive images are captured by an image capturing system that includes the x-ray tube, the focal spot may change position. To track the change, one or more artificial targets may be arranged relative to the image capturing system such that an initial image is received that includes the artificial targets at a first position in the initial image. A gain map may be generated based on the initial image, and applied to a subsequent image received that also includes the artificial targets to generate a normalized subsequent image. A shift of the artificial targets from the first position in the initial image to a second position in the normalized subsequent image may be identified, where the shift corresponds to the focal spot's position change. Mathematical and/or physical adjustments may be made to correct for the change.

20 Claims, 23 Drawing Sheets

(56) References Cited

U.S. PATENT DOCUMENTS

| | | |
|---|---|---|
| 4,160,906 A | 7/1979 | Daniels et al. |
| 4,310,766 A | 1/1982 | Finkenzeller et al. |
| 4,380,086 A | 4/1983 | Vagi |
| 4,496,557 A | 1/1985 | Malen et al. |
| 4,513,433 A | 4/1985 | Weiss et al. |
| 4,542,521 A | 9/1985 | Hahn et al. |
| 4,559,641 A | 12/1985 | Caugant et al. |
| 4,662,379 A | 5/1987 | Macovski |
| 4,706,269 A | 11/1987 | Reina et al. |
| 4,721,856 A | 1/1988 | Saotome et al. |
| 4,744,099 A | 5/1988 | Huettenrauch et al. |
| 4,752,948 A | 6/1988 | MacMahon |
| 4,760,589 A | 7/1988 | Siczek |
| 4,763,343 A | 8/1988 | Yanaki |
| 4,773,086 A | 9/1988 | Fujita et al. |
| 4,773,087 A | 9/1988 | Plewes |
| 4,799,248 A | 1/1989 | Furbee |
| 4,819,258 A | 4/1989 | Kleinman et al. |
| 4,821,727 A | 4/1989 | Levene et al. |
| 4,901,335 A | 2/1990 | Ferlic |
| 4,969,174 A | 11/1990 | Scheid et al. |
| 4,989,227 A | 1/1991 | Tirelli et al. |
| 4,998,270 A | 3/1991 | Scheid et al. |
| 5,018,176 A | 5/1991 | Romeas et al. |
| RE33,634 E | 7/1991 | Yanaki |
| 5,029,193 A | 7/1991 | Saffer |
| 5,051,904 A | 9/1991 | Griffith |
| 5,078,142 A | 1/1992 | Siczek et al. |
| 5,129,911 A | 7/1992 | Siczek et al. |
| 5,142,557 A | 8/1992 | Toker |
| 5,163,075 A | 11/1992 | Lubinsky et al. |
| 5,164,976 A | 11/1992 | Scheid et al. |
| 5,199,056 A | 3/1993 | Darrah |
| 5,212,637 A | 5/1993 | Saxena |
| 5,219,351 A | 6/1993 | Teubner |
| 5,240,011 A | 8/1993 | Assa |
| 5,256,370 A | 10/1993 | Slattery et al. |
| 5,274,690 A | 12/1993 | Burke |
| 5,289,520 A | 2/1994 | Pellegrino et al. |
| 5,291,539 A | 3/1994 | Thumann et al. |
| 5,313,510 A | 5/1994 | Ebersberger |
| 5,359,637 A | 10/1994 | Webber |
| 5,365,562 A | 11/1994 | Toker |
| 5,415,169 A | 5/1995 | Siczek et al. |
| 5,426,685 A | 6/1995 | Pellegrino et al. |
| 5,451,789 A | 9/1995 | Wong |
| 5,452,367 A | 9/1995 | Bick et al. |
| 5,479,927 A | 1/1996 | Shmulewitz |
| 5,483,072 A | 1/1996 | Coe |
| 5,506,877 A | 4/1996 | Niklason et al. |
| 5,526,394 A | 6/1996 | Siczek et al. |
| 5,528,658 A | 6/1996 | Hell |
| 5,539,797 A | 7/1996 | Heidsieck et al. |
| 5,553,111 A | 9/1996 | Moore et al. |
| 5,592,562 A | 1/1997 | Rooks |
| 5,594,769 A | 1/1997 | Pellegrino et al. |
| 5,596,200 A | 1/1997 | Sharma et al. |
| 5,598,454 A | 1/1997 | Franetzke et al. |
| 5,606,589 A | 2/1997 | Pellegrino et al. |
| 5,609,152 A | 3/1997 | Pellegrino et al. |
| 5,627,869 A | 5/1997 | Andrew et al. |
| 5,657,362 A | 8/1997 | Giger et al. |
| 5,668,844 A | 9/1997 | Webber |
| 5,668,889 A | 9/1997 | Hara |
| 5,706,327 A | 1/1998 | Adamkowski et al. |
| 5,719,952 A | 2/1998 | Rooks |
| 5,735,264 A | 4/1998 | Siczek et al. |
| 5,769,086 A | 6/1998 | Ritchart et al. |
| 5,773,832 A | 6/1998 | Sayed et al. |
| 5,803,912 A | 9/1998 | Siczek et al. |
| 5,818,898 A | 10/1998 | Tsukamoto et al. |
| 5,828,722 A | 10/1998 | Ploetz et al. |
| 5,841,829 A | 11/1998 | Dolazza |
| 5,844,242 A | 12/1998 | Jalink, Jr. |
| 5,844,965 A | 12/1998 | Galkin |
| 5,864,146 A | 1/1999 | Karellas |
| 5,872,828 A | 2/1999 | Niklason |
| 5,878,104 A | 3/1999 | Ploetz |
| 5,896,437 A | 4/1999 | Ploetz |
| 5,901,197 A | 5/1999 | Khutoryansky |
| 5,930,330 A | 7/1999 | Wolfe |
| 5,941,832 A | 8/1999 | Tumey et al. |
| 5,970,118 A | 10/1999 | Sokolov |
| 5,983,123 A | 11/1999 | Shmulewitz |
| 5,986,662 A | 11/1999 | Argiro et al. |
| 5,999,836 A | 12/1999 | Nelson et al. |
| 6,005,907 A | 12/1999 | Ploetz |
| 6,022,325 A | 2/2000 | Siczek et al. |
| 6,075,879 A | 6/2000 | Roehrig et al. |
| 6,081,577 A | 6/2000 | Webber |
| 6,091,841 A | 7/2000 | Rogers et al. |
| 6,101,236 A | 8/2000 | Wang et al. |
| 6,137,527 A | 10/2000 | Abdel-Malek et al. |
| 6,141,398 A | 10/2000 | He et al. |
| 6,149,301 A | 11/2000 | Kautzer et al. |
| 6,167,115 A | 12/2000 | Inoue |
| 6,175,117 B1 | 1/2001 | Komardin et al. |
| 6,196,715 B1 | 3/2001 | Nambu et al. |
| 6,207,958 B1 | 3/2001 | Giakos |
| 6,216,540 B1 | 4/2001 | Nelson et al. |
| 6,219,059 B1 | 4/2001 | Argiro |
| 6,233,473 B1 | 5/2001 | Shepherd et al. |
| 6,243,441 B1 | 6/2001 | Zur |
| 6,244,507 B1 | 6/2001 | Garland |
| 6,256,369 B1 | 7/2001 | Lai |
| 6,256,370 B1 | 7/2001 | Yavuz |
| 6,269,176 B1 | 7/2001 | Barski |
| 6,272,207 B1 | 8/2001 | Tang |
| 6,282,264 B1 | 8/2001 | Smith |
| 6,289,235 B1 | 9/2001 | Webber et al. |
| 6,292,530 B1 | 9/2001 | Yavus et al. |
| 6,292,531 B1 | 9/2001 | Hsieh et al. |
| 6,293,282 B1 | 9/2001 | Lemelson |
| 6,327,336 B1 | 12/2001 | Gingold et al. |
| 6,341,156 B1 | 1/2002 | Baetz et al. |
| 6,345,194 B1 | 2/2002 | Nelson et al. |
| 6,375,352 B1 | 4/2002 | Hewes et al. |
| 6,399,951 B1 | 6/2002 | Paulus |
| 6,411,836 B1 | 6/2002 | Patel et al. |
| 6,415,015 B2 | 7/2002 | Nicolas et al. |
| 6,418,189 B1 | 7/2002 | Schafer |
| 6,442,288 B1 | 8/2002 | Haerer et al. |
| 6,459,925 B1 | 10/2002 | Nields et al. |
| 6,463,181 B2 | 10/2002 | Duarte |
| 6,480,565 B1 | 11/2002 | Ning |
| 6,490,476 B1 | 12/2002 | Townsend et al. |
| 6,496,557 B2 | 12/2002 | Wilson |
| 6,501,819 B2 | 12/2002 | Unger et al. |
| 6,542,575 B1 | 4/2003 | Schubert |
| 6,553,096 B1 | 4/2003 | Zhou et al. |
| 6,556,655 B1 | 4/2003 | Chichereau et al. |
| 6,574,304 B1 | 6/2003 | Hsieh et al. |
| 6,574,629 B1 | 6/2003 | Cooke, Jr. et al. |
| 6,597,762 B1 | 7/2003 | Ferrant et al. |
| 6,611,575 B1 | 8/2003 | Alyassin et al. |
| 6,620,111 B2 | 9/2003 | Stephens et al. |
| 6,626,849 B2 | 9/2003 | Huitema et al. |
| 6,633,626 B2 | 10/2003 | Trotter et al. |
| 6,633,674 B1 | 10/2003 | Barnes et al. |
| 6,638,235 B2 | 10/2003 | Miller et al. |
| 6,647,092 B2 | 11/2003 | Eberhard et al. |
| 6,674,835 B2 | 1/2004 | Kaufhold |
| 6,702,459 B2 | 3/2004 | Barnes et al. |
| 6,744,848 B2 | 6/2004 | Stanton et al. |
| 6,748,044 B2 | 6/2004 | Sabol et al. |
| 6,748,046 B2 | 6/2004 | Thayer |
| 6,748,047 B2 | 6/2004 | Gonzalez |
| 6,751,285 B2 | 6/2004 | Eberhard et al. |
| 6,758,824 B1 | 7/2004 | Miller et al. |
| 6,813,334 B2 | 11/2004 | Koppe et al. |
| 6,846,289 B2 | 1/2005 | Besson |
| 6,882,700 B2 | 4/2005 | Wang et al. |
| 6,885,724 B2 | 4/2005 | Li et al. |
| 6,895,076 B2 | 5/2005 | Halsmer |

(56) References Cited

U.S. PATENT DOCUMENTS

| | | |
|---|---|---|
| 6,901,132 B2 | 5/2005 | Eberhard |
| 6,909,790 B2 | 6/2005 | Tumey et al. |
| 6,909,792 B1 | 6/2005 | Carrott et al. |
| 6,912,319 B1 | 6/2005 | Barnes et al. |
| 6,931,093 B2 | 8/2005 | Op De Beek et al. |
| 6,940,943 B2 | 9/2005 | Claus |
| 6,950,492 B2 | 9/2005 | Besson |
| 6,950,493 B2 | 9/2005 | Besson |
| 6,957,099 B1 | 10/2005 | Arnone et al. |
| 6,960,020 B2 | 11/2005 | Lai |
| 6,970,531 B2 | 11/2005 | Eberhard et al. |
| 6,970,586 B2 | 11/2005 | Baertsch |
| 6,978,040 B2 | 12/2005 | Berestov |
| 6,987,831 B2 | 1/2006 | Ning |
| 6,999,554 B2 | 2/2006 | Mertelmeier |
| 7,001,071 B2 | 2/2006 | Deuringer |
| 7,016,461 B2 | 3/2006 | Rotondo |
| 7,092,482 B2 | 8/2006 | Besson |
| 7,110,490 B2 | 9/2006 | Eberhard |
| 7,110,502 B2 | 9/2006 | Tsuji |
| 7,116,749 B2 | 10/2006 | Besson |
| 7,123,684 B2 | 10/2006 | Jing et al. |
| 7,127,091 B2 | 10/2006 | Op De Beek et al. |
| 7,142,633 B2 | 11/2006 | Eberhard et al. |
| 7,190,758 B2 | 3/2007 | Hagiwara |
| 7,206,462 B1 | 4/2007 | Betke |
| 7,218,766 B2 | 5/2007 | Eberhard |
| 7,244,063 B2 | 7/2007 | Eberhard |
| 7,245,694 B2 | 7/2007 | Jing et al. |
| 7,263,214 B2 | 8/2007 | Uppaluri |
| 7,286,645 B2 | 10/2007 | Freudenberger |
| 7,302,031 B2 | 11/2007 | Hjarn et al. |
| 7,315,607 B2 | 1/2008 | Ramsauer |
| 7,319,734 B2 | 1/2008 | Besson |
| 7,319,735 B2 | 1/2008 | Defreitas et al. |
| 7,319,736 B2 | 1/2008 | Rotondo |
| 7,323,692 B2 | 1/2008 | Rowlands et al. |
| 7,331,264 B2 | 2/2008 | Ozawa |
| 7,356,113 B2 | 4/2008 | Wu |
| 7,430,272 B2 | 9/2008 | Jing et al. |
| 7,433,507 B2 | 10/2008 | Jabri |
| 7,443,949 B2 | 10/2008 | Defreitas et al. |
| 7,466,795 B2 | 12/2008 | Eberhard et al. |
| 7,577,282 B2 | 8/2009 | Gkanatsios et al. |
| 7,583,786 B2 | 9/2009 | Jing et al. |
| 7,609,806 B2 | 10/2009 | Defreitas et al. |
| 7,609,808 B2 | 10/2009 | Tornai |
| 7,616,731 B2 | 11/2009 | Pack |
| 7,616,801 B2 | 11/2009 | Gkanatsios et al. |
| 7,630,531 B2 | 12/2009 | Chui |
| 7,630,533 B2 | 12/2009 | Ruth et al. |
| 7,688,940 B2 | 3/2010 | Defreitas et al. |
| 7,697,660 B2 | 4/2010 | Ning |
| 7,702,142 B2 | 4/2010 | Ren et al. |
| 7,760,853 B2 | 7/2010 | Jing et al. |
| 7,760,924 B2 | 7/2010 | Ruth et al. |
| 7,792,241 B2 | 9/2010 | Wu |
| 7,792,245 B2 | 9/2010 | Hitzke et al. |
| 7,831,296 B2 | 11/2010 | Defreitas et al. |
| 7,839,979 B2 | 11/2010 | Hauttmann |
| 7,869,563 B2 | 1/2011 | Defreitas et al. |
| 7,869,862 B2 | 1/2011 | Seppi |
| 7,881,428 B2 | 2/2011 | Jing et al. |
| 7,885,384 B2 | 2/2011 | Mannar |
| 7,894,646 B2 | 2/2011 | Shirahata et al. |
| 7,916,915 B2 | 3/2011 | Gkanatsios et al. |
| 7,949,091 B2 | 5/2011 | Jing et al. |
| 7,986,765 B2 | 7/2011 | Defreitas et al. |
| 7,991,106 B2 | 8/2011 | Ren |
| 8,031,834 B2 | 10/2011 | Ludwig |
| 8,131,049 B2 | 3/2012 | Ruth et al. |
| 8,155,421 B2 | 4/2012 | Ren et al. |
| 8,170,320 B2 | 5/2012 | Smith et al. |
| 8,175,219 B2 | 5/2012 | Defreitas et al. |
| 8,285,020 B2 | 10/2012 | Gkanatsios et al. |
| 8,416,915 B2 | 4/2013 | Jing et al. |
| 8,452,379 B2 | 5/2013 | DeFreitas et al. |
| 8,457,282 B2 | 6/2013 | Baorui et al. |
| 8,515,005 B2 | 8/2013 | Ren et al. |
| 8,532,745 B2 | 9/2013 | DeFreitas et al. |
| 8,559,595 B2 | 10/2013 | Defreitas et al. |
| 8,565,372 B2 | 10/2013 | Stein et al. |
| 8,565,374 B2 | 10/2013 | DeFreitas et al. |
| 8,565,860 B2 | 10/2013 | Kimchy |
| 8,571,289 B2 | 10/2013 | Ruth et al. |
| 8,712,127 B2 | 4/2014 | Ren et al. |
| 8,767,911 B2 | 7/2014 | Ren et al. |
| 8,787,522 B2 | 7/2014 | Smith et al. |
| 8,831,171 B2 | 9/2014 | Jing et al. |
| 8,853,635 B2 | 10/2014 | O'Connor |
| 8,873,716 B2 | 10/2014 | Ren et al. |
| 9,042,612 B2 | 5/2015 | Gkanatsios et al. |
| 9,066,706 B2 | 6/2015 | Defreitas et al. |
| 9,226,721 B2 | 1/2016 | Ren et al. |
| 9,460,508 B2 | 10/2016 | Gkanatsios et al. |
| 9,498,175 B2 | 11/2016 | Stein et al. |
| 9,502,148 B2 | 11/2016 | Ren et al. |
| 9,549,709 B2 | 1/2017 | DeFreitas et al. |
| 9,851,888 B2 | 12/2017 | Gkanatsios et al. |
| 9,895,115 B2 | 2/2018 | Ren |
| 10,108,329 B2 | 10/2018 | Gkanatsios et al. |
| 10,194,875 B2 | 2/2019 | DeFreitas et al. |
| 10,296,199 B2 | 5/2019 | Gkanatsios |
| 10,413,255 B2 | 9/2019 | Stein |
| 10,452,252 B2 | 10/2019 | Gkanatsios et al. |
| 10,638,994 B2 | 5/2020 | DeFreitas |
| 10,719,223 B2 | 7/2020 | Gkanatsios |
| 10,881,359 B2 | 1/2021 | Williams |
| 2001/0038681 A1 | 11/2001 | Stanton et al. |
| 2002/0012450 A1 | 1/2002 | Tsujii |
| 2002/0048343 A1 | 4/2002 | Launay et al. |
| 2002/0050986 A1 | 5/2002 | Inouc et al. |
| 2002/0070970 A1 | 6/2002 | Wood et al. |
| 2002/0075997 A1 | 6/2002 | Unger et al. |
| 2002/0090055 A1 | 7/2002 | Zur et al. |
| 2002/0094062 A1 | 7/2002 | Dolazza |
| 2002/0113681 A1 | 8/2002 | Byram |
| 2002/0122533 A1 | 9/2002 | Marie et al. |
| 2002/0126798 A1 | 9/2002 | Harris |
| 2003/0007598 A1 | 1/2003 | Wang et al. |
| 2003/0010923 A1 | 1/2003 | Zur |
| 2003/0018272 A1 | 1/2003 | Treado et al. |
| 2003/0026386 A1 | 2/2003 | Tang et al. |
| 2003/0058989 A1 | 3/2003 | Rotondo |
| 2003/0072409 A1 | 4/2003 | Kaufhold et al. |
| 2003/0072417 A1 | 4/2003 | Kaufhold et al. |
| 2003/0073895 A1 | 4/2003 | Nields et al. |
| 2003/0095624 A1 | 5/2003 | Eberhard et al. |
| 2003/0097055 A1 | 5/2003 | Yanof et al. |
| 2003/0149364 A1 | 8/2003 | Kapur |
| 2003/0169847 A1 | 9/2003 | Karellas et al. |
| 2003/0194050 A1 | 10/2003 | Eberhard |
| 2003/0194051 A1 | 10/2003 | Wang et al. |
| 2003/0194121 A1 | 10/2003 | Eberhard et al. |
| 2003/0210254 A1 | 11/2003 | Doan et al. |
| 2003/0212327 A1 | 11/2003 | Wang et al. |
| 2003/0215120 A1 | 11/2003 | Uppaluri et al. |
| 2004/0008809 A1 | 1/2004 | Webber |
| 2004/0066882 A1 | 4/2004 | Eberhard et al. |
| 2004/0066884 A1 | 4/2004 | Claus et al. |
| 2004/0066904 A1 | 4/2004 | Eberhard et al. |
| 2004/0070582 A1 | 4/2004 | Smith et al. |
| 2004/0094167 A1 | 5/2004 | Brady et al. |
| 2004/0101095 A1 | 5/2004 | Jing et al. |
| 2004/0109529 A1 | 6/2004 | Eberhard |
| 2004/0146221 A1 | 7/2004 | Siegel et al. |
| 2004/0171986 A1 | 9/2004 | Tremaglio, Jr. et al. |
| 2004/0190682 A1 | 9/2004 | Deuringer |
| 2004/0213378 A1 | 10/2004 | Zhou et al. |
| 2004/0247081 A1 | 12/2004 | Halsmer |
| 2004/0264627 A1 | 12/2004 | Besson |
| 2004/0267157 A1 | 12/2004 | Miller et al. |
| 2005/0025278 A1 | 2/2005 | Hagiwara |
| 2005/0049497 A1 | 3/2005 | Krishnan |

(56) References Cited

U.S. PATENT DOCUMENTS

| | | |
|---|---|---|
| 2005/0049521 A1 | 3/2005 | Miller et al. |
| 2005/0063509 A1 | 3/2005 | DeFreitas et al. |
| 2005/0078797 A1 | 4/2005 | Danielsson et al. |
| 2005/0089205 A1 | 4/2005 | Kapur |
| 2005/0105679 A1 | 5/2005 | Wu et al. |
| 2005/0113681 A1 | 5/2005 | Defreitas |
| 2005/0113715 A1 | 5/2005 | Schwindt et al. |
| 2005/0117694 A1 | 6/2005 | Francke |
| 2005/0129172 A1 | 6/2005 | Mertelmeier |
| 2005/0133706 A1 | 6/2005 | Eberhard |
| 2005/0135555 A1 | 6/2005 | Claus et al. |
| 2005/0135664 A1 | 6/2005 | Kaufhold et al. |
| 2005/0226375 A1 | 10/2005 | Eberhard et al. |
| 2005/0248347 A1 | 11/2005 | Damadian |
| 2006/0009693 A1 | 1/2006 | Hanover et al. |
| 2006/0030784 A1 | 2/2006 | Miller et al. |
| 2006/0034426 A1 | 2/2006 | Freudenberger |
| 2006/0074288 A1 | 4/2006 | Kelly |
| 2006/0098855 A1 | 5/2006 | Gkanatsios et al. |
| 2006/0109951 A1 | 5/2006 | Popescu |
| 2006/0126780 A1 | 6/2006 | Rotondo |
| 2006/0129062 A1 | 6/2006 | Nicoson et al. |
| 2006/0155209 A1 | 7/2006 | Miller et al. |
| 2006/0210016 A1 | 9/2006 | Francke |
| 2006/0257009 A1 | 11/2006 | Wang |
| 2006/0262898 A1 | 11/2006 | Partain |
| 2006/0269041 A1 | 11/2006 | Mertelmeier |
| 2006/0291618 A1 | 12/2006 | Eberhard et al. |
| 2007/0030949 A1 | 2/2007 | Jing et al. |
| 2007/0036265 A1 | 2/2007 | Jing et al. |
| 2007/0076844 A1 | 4/2007 | Defreitas et al. |
| 2007/0078335 A1 | 4/2007 | Horn |
| 2007/0140419 A1 | 6/2007 | Souchay |
| 2007/0223651 A1 | 9/2007 | Wagenaar et al. |
| 2007/0225600 A1 | 9/2007 | Weibrecht et al. |
| 2007/0242800 A1 | 10/2007 | Jing et al. |
| 2008/0019581 A1 | 1/2008 | Gkanatsios et al. |
| 2008/0045833 A1 | 2/2008 | Defreitas et al. |
| 2008/0056436 A1 | 3/2008 | Pack |
| 2008/0101537 A1 | 5/2008 | Sendai |
| 2008/0112534 A1 | 5/2008 | Defreitas |
| 2008/0118023 A1 | 5/2008 | Besson |
| 2008/0130979 A1 | 6/2008 | Ren |
| 2008/0198966 A1 | 8/2008 | Hjam |
| 2008/0212861 A1 | 9/2008 | Durgan et al. |
| 2008/0285712 A1 | 11/2008 | Kopans |
| 2008/0317196 A1 | 12/2008 | Imai |
| 2009/0003519 A1 | 1/2009 | Defreitas et al. |
| 2009/0010384 A1 | 1/2009 | Jing et al. |
| 2009/0080594 A1 | 3/2009 | Brooks et al. |
| 2009/0080602 A1 | 3/2009 | Brooks et al. |
| 2009/0080604 A1 | 3/2009 | Shores et al. |
| 2009/0135997 A1 | 5/2009 | Defreitas et al. |
| 2009/0141859 A1 | 6/2009 | Gkanatsios et al. |
| 2009/0143674 A1 | 6/2009 | Nields |
| 2009/0177495 A1 | 7/2009 | Abousy |
| 2009/0213987 A1 | 8/2009 | Stein et al. |
| 2009/0237924 A1 | 9/2009 | Ladewig |
| 2009/0238424 A1 | 9/2009 | Arakita et al. |
| 2009/0268865 A1 | 10/2009 | Ren et al. |
| 2009/0296882 A1 | 12/2009 | Gkanatsios |
| 2009/0304147 A1 | 12/2009 | Jing et al. |
| 2010/0020937 A1 | 1/2010 | Hautmann |
| 2010/0020938 A1 | 1/2010 | Koch |
| 2010/0034450 A1 | 2/2010 | Mertelmeier |
| 2010/0054400 A1 | 3/2010 | Ren |
| 2010/0086188 A1 | 4/2010 | Ruth |
| 2010/0091940 A1 | 4/2010 | Ludwig et al. |
| 2010/0150306 A1 | 6/2010 | Defreitas et al. |
| 2010/0189227 A1 | 7/2010 | Mannar |
| 2010/0195882 A1 | 8/2010 | Ren |
| 2010/0226475 A1 | 9/2010 | Smith |
| 2010/0290585 A1 | 11/2010 | Eliasson |
| 2010/0303202 A1 | 12/2010 | Ren |
| 2010/0313196 A1 | 12/2010 | De Atley et al. |
| 2011/0026667 A1 | 2/2011 | Poorter |
| 2011/0069809 A1 | 3/2011 | Defreitas et al. |
| 2011/0087132 A1 | 4/2011 | DeFreitas et al. |
| 2011/0178389 A1 | 7/2011 | Kumar et al. |
| 2011/0188624 A1 | 8/2011 | Ren |
| 2011/0234630 A1 | 9/2011 | Batman et al. |
| 2011/0237927 A1 | 9/2011 | Brooks et al. |
| 2011/0268246 A1 | 11/2011 | Dafni |
| 2012/0033868 A1 | 2/2012 | Ren |
| 2012/0051502 A1 | 3/2012 | Ohta et al. |
| 2012/0236987 A1 | 9/2012 | Ruimi |
| 2012/0238870 A1 | 9/2012 | Smith et al. |
| 2013/0028374 A1 | 1/2013 | Gkanatsios et al. |
| 2013/0077748 A1 | 3/2013 | Althoff et al. |
| 2013/0211261 A1 | 8/2013 | Wang |
| 2013/0272494 A1 | 10/2013 | DeFreitas et al. |
| 2014/0044230 A1 | 2/2014 | Stein et al. |
| 2014/0044231 A1 | 2/2014 | Defreitas et al. |
| 2014/0086471 A1 | 3/2014 | Ruth et al. |
| 2014/0098935 A1 | 4/2014 | Defreitas et al. |
| 2014/0232752 A1 | 8/2014 | Ren et al. |
| 2014/0314198 A1 | 10/2014 | Ren et al. |
| 2014/0321607 A1 | 10/2014 | Smith |
| 2014/0376690 A1 | 12/2014 | Jing et al. |
| 2015/0049859 A1 | 2/2015 | DeFreitas et al. |
| 2015/0160848 A1 | 6/2015 | Gkanatsios et al. |
| 2015/0310611 A1 | 10/2015 | Gkanatsios et al. |
| 2015/0347693 A1 | 12/2015 | Lam |
| 2015/0352376 A1* | 12/2015 | Wiggers .................. A61B 6/06 378/207 |
| 2016/0106383 A1 | 4/2016 | Ren et al. |
| 2016/0220207 A1 | 8/2016 | Jouhikainen |
| 2016/0256125 A1 | 9/2016 | Smith |
| 2016/0270742 A9 | 9/2016 | Stein et al. |
| 2016/0331339 A1 | 11/2016 | Guo |
| 2017/0024113 A1 | 1/2017 | Gkanatsios et al. |
| 2017/0128028 A1 | 5/2017 | DeFreitas et al. |
| 2017/0135650 A1 | 5/2017 | Stein et al. |
| 2017/0135653 A1 | 5/2017 | Ren |
| 2017/0319167 A1 | 11/2017 | Goto |
| 2017/0372863 A1 | 12/2017 | Price |
| 2018/0005796 A1 | 1/2018 | Iida |
| 2018/0068066 A1 | 3/2018 | Bronkalla |
| 2018/0130201 A1 | 5/2018 | Bernard |
| 2018/0177476 A1 | 6/2018 | Jing et al. |
| 2018/0188937 A1 | 7/2018 | Gkanatsios et al. |
| 2018/0289347 A1 | 10/2018 | DeFreitas et al. |
| 2018/0344276 A1 | 12/2018 | DeFreitas et al. |
| 2019/0059830 A1 | 2/2019 | Williams |
| 2019/0095087 A1 | 3/2019 | Gkanatsios et al. |
| 2019/0138693 A1 | 5/2019 | Serge |
| 2019/0188848 A1 | 6/2019 | Madani |
| 2019/0200942 A1 | 7/2019 | DeFreitas |
| 2019/0221304 A1 | 7/2019 | Ionasec |
| 2019/0295248 A1 | 9/2019 | Nakamura |
| 2019/0336794 A1 | 11/2019 | Li |
| 2020/0012417 A1 | 1/2020 | Gkanatsios |
| 2020/0029927 A1 | 1/2020 | Wilson |
| 2020/0043600 A1 | 2/2020 | Glottmann |
| 2020/0085393 A1 | 3/2020 | Zhang |
| 2020/0167920 A1 | 5/2020 | Hall |
| 2020/0286613 A1 | 9/2020 | Rego |
| 2020/0348835 A1 | 11/2020 | Gkanatsios |
| 2020/0352531 A1 | 11/2020 | Smith |
| 2021/0176850 A1 | 6/2021 | Ru |
| 2021/0303078 A1 | 9/2021 | Wells |

FOREIGN PATENT DOCUMENTS

| | | |
|---|---|---|
| DE | 102004051401 | 5/2006 |
| DE | 102004051820 | 5/2006 |
| DE | 102010027871 | 10/2011 |
| DE | 102011007215 | 10/2012 |
| EP | 0775467 | 5/1997 |
| EP | 0982001 | 3/2000 |
| EP | 1028451 | 8/2000 |
| EP | 1428473 | 6/2004 |
| EP | 1623672 | 2/2006 |
| EP | 1759637 | 3/2007 |

(56) References Cited

FOREIGN PATENT DOCUMENTS

| | | |
|---|---|---|
| EP | 1569556 | 4/2012 |
| EP | 2732764 | 5/2014 |
| EP | 2602743 | 11/2014 |
| EP | 2819145 | 12/2014 |
| EP | 3143935 | 3/2017 |
| EP | 3569148 A1 * 11/2019 | ........... A61B 6/4233 |
| GB | 415709 | 8/1934 |
| JP | 53151381 U | 11/1978 |
| JP | H 05-329143 | 12/1993 |
| JP | H07-230778 | 8/1995 |
| JP | 2000-287960 | 10/2000 |
| JP | 2001-346786 | 12/2001 |
| JP | 2002219124 | 8/2002 |
| JP | 2004-511884 | 4/2004 |
| JP | 2004-188200 | 7/2004 |
| JP | 2004-528682 | 9/2004 |
| JP | 2005-142160 | 6/2005 |
| JP | 2006-519625 | 8/2006 |
| JP | 2006-231054 | 9/2006 |
| JP | 2007-50264 | 3/2007 |
| JP | 2007-054528 | 3/2007 |
| JP | 2007-521911 | 8/2007 |
| JP | 2007229269 | 9/2007 |
| JP | 2008-67933 | 3/2008 |
| JP | 2008086471 | 4/2008 |
| JP | 2008-159317 | 7/2008 |
| JP | 2009500048 | 1/2009 |
| JP | 2011-516116 | 5/2011 |
| WO | 90/05485 | 5/1990 |
| WO | 9803115 | 1/1998 |
| WO | 98/16903 | 4/1998 |
| WO | 00/51484 | 9/2000 |
| WO | 2000068863 | 11/2000 |
| WO | 03/020114 | 3/2003 |
| WO | 03037046 | 5/2003 |
| WO | 2003/057564 | 7/2003 |
| WO | 2004/043535 | 5/2004 |
| WO | 2005/051197 | 6/2005 |
| WO | 2005/110230 | 11/2005 |
| WO | 2005/112767 | 12/2005 |
| WO | 2006/004185 | 1/2006 |
| WO | 2006055830 | 5/2006 |
| WO | 2006/058160 | 6/2006 |
| WO | 2007129244 | 11/2007 |
| WO | 2008072144 | 6/2008 |
| WO | 2009122328 | 10/2009 |
| WO | 2009136349 | 11/2009 |
| WO | 2010/070554 | 6/2010 |
| WO | 2013/184213 | 12/2013 |
| WO | 2019/030410 | 2/2019 |
| WO | 2016/057960 | 5/2019 |

OTHER PUBLICATIONS

"Essentials for life: Senographe Essential Full-Field Digital Mammography system", GE Health-care Brochure, MM-0132-05.06-EN-US, 2006, 12 pgs.
"Filtered Back Projection," (NYGREN) published May 8, 2007; URL:http://web.archive.org/web/19991010131715/http://www.owlnet.rice.edu/.about.e1 ec539/Projects97/cult/node2.html., 2 pgs.
"Lorad Selenia" Document B-BI-SEO US/Intl (May 2006) copyright Hologic 2006, 12 pgs.
Acrin website, located at https://www.acrin.org/PATIENTS/ABOUTIMAGINGEXAMSANDAGENTS/ABOUTMAMMOGRAPHYANDTOMOSYNTHESIS.aspx, "About Mammography and Tomosynthesis", obtained online on Dec. 8, 2015, 5 pgs.
American College of Radiology website, located at http://www.acr.org/FAQs/DBT-FAQ, "Digital Breast Tomosynthesis FAQ for Insurers", obtained online on Dec. 8, 2015, 2 pages.
Arfelli, F. et al., "Mammography with synchrotron radiation: phase-detection techniques", Apr. 2000, retrieved at: https://www.ncbi.nlm.nih.gov/pubmed/10751500, 8 pages.

Aslund, Magnus, "Digital Mammography with a Photon Counting Detector in a Scanned Multislit Geometry", Doctoral Thesis, Dept of Physics, Royal Institute of Technology, Stockholm, Sweden, Apr. 2007, 51 pages.
Boone, J. et al., "Dedicated Breast CT: Radiation Dose and Image Quality Evaluation", Dec. 31, 2001, retrieved at: http://pubs.rsna.org/doi/abs/10.1148/radiol.2213010334, 11 pages.
Chan, Heang-Ping et al., "ROC study of the effect of stereoscopic imaging on assessment of breast lesions", Medical Physics, vol. 32, No. 4, Apr. 2005, 7 pgs.
Choi, Bareum et al., "Surgical-tools detection based on Convolutional Neural Network in Laparoscopic Robot-Assisted Surrgery", 2017 39th Annual Int'l. Conference of the IEEE Engineering in Medicine and Biology Society (EMBC), IEEE, Jul. 11, 2017, pp. 1756-1759.
Cole, Elodia, et al., "The Effects of Gray Scale Image Processing on Digital Mammography Interpretation Performance", Academic Radiology, vol. 12, No. 5, pp. 585-595, May 2005.
Digital Clinical Reports, Tomosynthesis, GE Brochure 98-5493, Nov. 1998, 8 pgs.
Dobbins, James T., "Digital x-ray tomosynthesis: current state of the art and clinical potential," Physics in Medicine and Biology, Taylor and Francis LTD, London GB, vol. 48, No. 19, Oct. 7, 2003, 42 pages.
Grant, David G., "Tomosynthesis: a three-dimensional imaging technique", IEEE Trans. Biomed. Engineering, vol. BME-19, #1, Jan. 1972, pp. 20-28.
Hamberg, Leena M., "Tomosynthesis breast imaging: early detection and characterization of breast cancer", prepared by Massachusetts General Hospital for the U.S. Army Medical Research and Material Command Fort Detrick, Maryland, Jul. 2000, 20 pages.
Han et al., "MatchNet: Unifying Feature and Metric Learning for Patch-Based Matching", 2015 IEEE Conference on Computer Vision and Pattern Recognition (CVPR), Boston, MA, 2015, pp. 3279-3286.
Kachelriess, Marc et al., "Flying Focal Spot (FFS) in Cone-Beam CT", 2004 IEEE Nuclear Science Symposium Conference Record, Oct. 16-22, 2004, Rome Italy, vol. 6, pp. 3759-3763.
Kapur, Ajay et al., "Combination of Digital Mammography with Semiautomated 3D Breast Ultrasound", Aug. 1, 2004, retrieved at: http://journals.sagepub.eom/doi/abs/10.1177/153303460400300402, 10 pages.
Kita et al., "Correspondence between different view breast X-rays using simulation of breast deformation", Proceedings 1998 IEE Computer Society Conference on Computer Vision and Pattern Recognition, Santa Barbara, CA, Jun. 23-25, 1998, pp. 700-707.
Kopans, D., "Development and Clinical Evaluation of Tomosynthesis for Digital Mammography", Oct. 31, 2000, retrieved at: http://oai.dtic.mil/oai/oai?verb=getRecord&metadataPrefix=html&identifier=ADA387722, 91 pages.
Kopans, Daniel B., "Breast Imaging", Chapter 26: Future Advances in Breast Imaging, 2nd Edition, Lippincott-Raven Publishers, Philadelphia, 1998, 37 pages.
Lehmann, V. et al., "MEMS techniques applied to the fabrication of anti-scatter grids for X-ray imaging", 2002, retrieved at: https://www.researchgate.net/profile/S_Ronnebeck/publication/222546207_MEMS_techniques_applied_to_the_fabrication_of_anti-scatter_grids_for_Xray_imaging/links/5570136f08aeccd777417301/MEMS-techniques-applied-to-the-fabrication-of-anti-scatter-grids-for-X-ray-imaging.pdf, 6 pages.
Mammographic Accreditation Phantom, http://www.cirsinc.com/pdfs/015cp.pdf. (2006), 2 pgs.
Niklason et al., "Digital breast tomosynthesis: potentially a new method for breast cancer screening", In Digital Mammography, 1998, 6 pages.
Niklason et al., "Digital Breast Imaging: Tomosynthesis and Digital Subtraction Mammography", Breast Disease, vol. 10, No. 3-4, pp. 151-164, 1998.
Niklason, Loren T. et al., "Digital Tomosynthesis in Breast Imaging", Radiology, Nov. 1997, vol. 205, No. 2, pp. 399-406.
Nykanen, Kirsi, et al., "X-ray scattering in full-field digital mammography", Jul. 2003, retrieved at: http://www.siltanen-research.net/publ/NykanenSiltanen2003.pdf, 10 pages.

(56) References Cited

OTHER PUBLICATIONS

Pediconi, Federica et al., "Color-coded automated signal intensity-curve for detection and characterization of breast lesions: Preliminary evaluation of a new software for MR-based breast imaging", International Congress Series 1281 (2005) 1081-1086.

Pisano, Etta D., "Digital Mammography", Radiology, vol. 234, No. 2, Feb. 2005, pp. 353-362.

Rolf Behling–Ed—Behling et al., Chapter 6: Diagnostic X-Ray Sources from the Inside, Modern Diagnostic X-Ray Sources, Taylor & Francis Group, pp. 177-308, Jan. 1, 2016, retrieved from the internet on Jun. 26, 2015 at: https://ebookcentral.proquest.com/lib/epo-ebooks/detail.action?docID=2075866.

Senographe 700 & 800T (GE); 2-page download on Jun. 22, 2006 from www.gehealthcare.com/inen/rad/whe/products/mswh800t.html.; Figures 1-7 on 4 sheets re lateral shift compression paddle, 2 pgs.

Smith, A., "Fundamentals of Breast Tomosynthesis", White Paper, Hologic Inc., WP-00007, Jun. 2008, 8 pgs.

Smith, Andrew, PhD, "Full Field Breast Tomosynthesis", Hologic White Paper, Oct. 2004, 6 pgs.

Suryanarayanan, S. et al., "Comparison of tomosynthesis methods used with digital mammography", Dec. 31, 2000, retrieved at: http://www.sciencedirect.com/science/article/pii/S1076633200800616, 13 pages.

Suryanarayanan, S. et al., "Evaluation of Linear and Nonlinear Tomosynthetic Reconstruction Methods in Digital Mammography", Mar. 2001, retrieved at: http://www.sciencedirect.com/science/article/pii/S1076633203805305, 6 pages.

Thurfjell, "Mammography screening: one versus two views and independent double reading", Acta Radiologica 35, No. 4, 1994, pp. 345-350.

Webber, Richard, "A controlled evaluation of tuned-aperture computed tomography applied to digital spot mammography", Feb. 2000, retrieved at: https://www.ncbi.nlm.nih.gov/pmc/articles/PMC3453191/, 8 pages.

Wheeler F. W., et al. "Micro-Calcification Detection in Digital Tomosynthesis Mammography", Proceedings of SPIE, Conf-Physics of Semiconductor Devices, Dec. 11, 2001 to Dec. 15, 2001, Delhi, SPIE, US, vol. 6144, Feb. 13, 2006, 12 pgs.

Wu, T. et al., "A comparison of reconstruction algorithms for breast tomosynthesis", Aug. 26, 2004, retrieved at: http://onlinelibrary.wiley.com/doi/10.1118/1.1786692/full.

Wu, Tao, et al. "Tomographic Mammography Using a Limited Number of Low-Dose Cone-Beam Projection Images" Medical Physics, AIP, Melville, NY, vol. 30, No. 3, Mar. 1, 2003, p. 365-380.

* cited by examiner

SYSTEM AND METHOD FOR TRACKING X-RAY TUBE FOCAL SPOT POSITION

CROSS-REFERENCE TO RELATED APPLICATION

This application claims the benefit of U.S. Provisional Patent Application No. 63/000,996, filed Mar. 27, 2020, entitled "SYSTEM AND METHOD FOR TRACKING X-RAY TUBE FOCAL SPOT POSITION," which application is hereby incorporated by reference in its entirety herein.

BACKGROUND

Imaging based on the use of x-rays is commonplace in medical imaging technology, such as mammography or tomosynthesis systems. The x-rays used in such imaging technology are often generated through the use of an x-ray tube. For example, to produce an x-ray beam for imaging, a voltage or signal may be applied across a filament of the x-ray tube causing electrons that form an electron beam to be emitted from the filament. The emitted electrons form an electron beam that accelerates towards an anode of the x-ray tube. The electron beam impacts the anode, which causes the emission of x-rays from the anode that form the x-ray beam used for imaging. The area in which the electron beam impacts the anode is referred to as the focal spot.

Due to the design of the x-ray tube and additional outside factors, the x-ray tube is susceptible to unstable focal spot position during successive image captures. A change in focal spot position can induce artifacts that may reduce the diagnostic usefulness of the resultant medical images. Additionally, the change in focal spot position is uncertain and unpredictable from one image capture to the next.

It is with respect to these and other general considerations that the aspects disclosed herein have been made. Also, although relatively specific problems may be discussed, it should be understood that the examples should not be limited to solving the specific problems identified in the background or elsewhere in this disclosure.

SUMMARY

Examples of the present disclosure describe a method and system for tracking a change in position of a focal spot of an x-ray tube.

In one aspect, the technology relates to a method for tracking a position of a focal spot of an x-ray tube. An example method may include receiving an initial image from an image capturing system comprising the x-ray tube, where the initial image may include an artificial target at a first position in the initial image, generating a gain map based on the initial image, and receiving a subsequent image from the image capturing system, where the subsequent image may include the artificial target. The method may also include applying the gain map to the subsequent image to generate a normalized subsequent image, and identifying a shift of the artificial target from the first position in the initial image to a second position in the normalized subsequent image, the shift corresponding to a change in the position of the focal spot from the capture of the initial image to the capture of the subsequent image.

In an example, to identify the shift, a profile plot may be generated along a line intersecting the artificial target in a region of the normalized subsequent image, where the profile plot includes pixel intensity values for a predefined range of pixels in the region along a direction of the line. A first pixel having a local maximum pixel intensity value and a second pixel having a local minimum pixel intensity value may be identified within the predefined range of pixels, and a pixel distance between the first pixel and the second pixel may be determined. In some examples, a median pixel intensity value for the predefined range of pixels may be determined. The first pixel having the local maximum pixel intensity value may be identified based on a determination that a pixel intensity value of the first pixel is greater than the median pixel intensity value by at least a threshold value. The second pixel having the local minimum pixel intensity value may be identified based on a determination that a pixel intensity value of the second pixel is less than the median pixel intensity value by at least a threshold value.

In another example, the normalized subsequent image may be adjusted based on the pixel distance. The gain map may be adjusted based on the pixel distance and reapplied to the subsequent image. The pixel distance may be converted to a focal spot shift vector representing the change in the position of the focal spot in the direction of the line. A control signal may be generated based on the focal spot shift vector for transmission to an apparatus that is capable of controlling dimensions of an electron beam received at an anode of the x-ray tube, where the dimensions of the electron beam may affect the position of the focal spot on the anode, and the control signal may cause the apparatus to adjust the dimensions of the electron beam to reverse the change in the position of the focal spot in the direction of the line.

In a further example, the artificial target may be arranged substantially parallel to an x-axis of a detector, and the shift of the artificial target from the first position to the second position may be identified in a direction parallel to a y-axis of the detector, the shift corresponding to the change in the position of the focal spot in the direction parallel to the y-axis of the detector. The artificial target may be arranged substantially parallel to a y-axis of a detector, and the shift of the artificial target from the first position to the second position may be identified in a direction parallel to an x-axis of the detector, the shift corresponding to the change in the position of the focal spot in the direction parallel to the x-axis of the detector.

In a yet further example, the initial image and the subsequent image may include at least two artificial targets. A first artificial target of the at least two artificial targets may be arranged in a first direction and a second artificial target of the at least two artificial targets may be arranged in a second direction. A shift of the first artificial target from a first position in the initial image to a second position in the normalized subsequent image may be identified, the shift corresponding to a change in the position of the focal spot in the second direction. A shift of the second artificial target from a first position in the initial image to a second position in the normalized subsequent image may be identified, the shift corresponding to a change in the position of the focal spot in the first direction.

In an example, to identify the shift of the first artificial target, a profile plot may be generated along a line in the second direction that intersects the first artificial target in a region of the normalized subsequent image, where the profile plot includes pixel intensity values for a predefined range of pixels in the region along the second direction of the line. A first pixel having a local maximum pixel intensity value and a second pixel having a local minimum pixel intensity value may be identified within the predefined range of pixels, a pixel distance between the first pixel and the second pixel in the second direction may be determined, and the pixel distance may be converted to a second direction focal spot shift vector representing the change in the position of the focal spot in the second direction. To identify the shift of the second artificial target, a profile plot may be generated along a line in the first direction that intersects the second artificial target in a region of the normalized subsequent image, where the profile plot includes pixel intensity values for a predefined range of pixels in the region along the first direction of the line. A first pixel having a local maximum pixel intensity value and a second pixel having a local minimum pixel intensity value may be identified within the predefined range of pixels, a pixel distance between the first pixel and the second pixel in the first direction may be determined, and the pixel distance may be converted to a first direction focal spot shift vector representing the change in the position of the focal spot in the first direction.

In another example, a resultant focal spot shift vector may be determined based on the first direction focal spot shift vector and the second direction focal spot shift vector. An angle associated with the resultant focal spot shift vector may be determined based on the first direction focal spot shift vector and the second direction focal spot shift vector, and a control signal may be generated based on the angle for transmission to an apparatus that is capable of controlling dimensions of an electron beam received at an anode of the x-ray tube, where the dimensions of the electron beam may affect the position of the focal spot on the anode, and the control signal may cause the apparatus to adjust the dimensions of the electron beam to reverse the change in the position of the focal spot in the first direction and the second direction.

In another aspect, the technology relates to a system for tracking and adjusting a position of a focal spot of an x-ray tube. An example system may include an image capturing system comprising at least the x-ray tube and a detector, an artificial target, an apparatus that is capable of controlling dimensions of an electron beam received at an anode of the x-ray tube, where the dimensions of the electron beam may affect the position of the focal spot on the anode, and an image processing system communicatively coupled to the image capturing system and the apparatus. The image processing system may include at least a processor, and a memory coupled to the processor and storing instructions. When the instructions are executed by the processor, the processor may receive, from the image capturing system, an initial image including the artificial target at a first position in the initial image, and generate a gain map based on the initial image. When the instructions are executed by the processor, the processor may also receive a subsequent image including the artificial target from the image capturing system, apply the gain map to the subsequent image to generate a normalized subsequent image, and identify a shift of the artificial target from the first position in the initial image to a second position in the normalized subsequent image, where the shift corresponds to a change in the position of the focal spot from the capture of the initial image to the capture of the subsequent image. When the instructions are executed by the processor, the processor may further generate a control signal to cause the apparatus to adjust the dimensions of the electron beam to reverse the change in the position of the focal spot, and transmit the control signal to the apparatus.

In a further aspect, the technology relates to a calibration method to enable a position of a focal spot of an x-ray tube to be tracked during patient imaging. An example method includes receiving an initial image and a subsequent image from an image capturing system comprising an x-ray tube, the initial image including a mesh object artificial target at a first position in the initial image and the subsequent image including the mesh object artificial target at a second position in the subsequent image, and generating a gain map from the initial image and applying the gain map to the subsequent image to generate a normalized subsequent image. The example method also includes identifying, for a plurality of regions across the x-axis and the y-axis in the normalized subsequent image, a shift of the mesh object artificial target within the respective region from the first position to the second position, where the respective region corresponds to one of x- and y-axis pixel coordinates of the image. The example method further includes determining a maximum shift across the x-axis and the y-axis, the maximum shift representing a change in a position of the focal spot, identifying at least one of an x-axis pixel coordinate and a y-axis pixel coordinate where an artificial target is to be positioned for patient imaging, deriving a ratio of the maximum shift to a shift identified at a region corresponding to the at least one of the x-axis pixel coordinate and the y-axis pixel coordinate where the artificial target is to be positioned for patient imaging, and applying the ratio to an identified shift of the artificial target in a pair of subsequently captured patient images to determine the change in the position of the focal spot.

In a yet further aspect, the technology relates to a computing device to track a change to a position of a focal spot of an x-ray tube for correcting image shifts caused by the change. An example computing device may include a processor and a memory coupled to the processor. The memory may store instructions, that when executed by the processor, cause the processor to: receive an initial image from an image capturing system comprising the x-ray tube, the initial image including an artificial target at a first position in the initial image; generate a gain map based on the initial image; receive a subsequent image captured by the image capturing system, the subsequent image including the artificial target; apply the gain map to the subsequent image to generate a normalized subsequent image; identify a shift of the artificial target from the first position in the initial image to a second position in the normalized subsequent image, the shift corresponding to a change in the position of the focal spot from the capture of the initial image to the capture of the subsequent image; and adjust the normalized subsequent image based on the identified shift.

In an aspect, the technology relates to a method for identifying an artifact induced by a change in a position of a focal spot of an x-ray tube. An example method may include receiving an initial pair of images from an image capturing system comprising the x-ray tube, the initial pair of images including an artificial target at a first position in an initial high energy image and an initial low energy image, generating a high energy gain map based on the initial high energy image, and generating a low energy gain map based on the initial low energy image. The method may also include receiving a subsequent pair of images from the image capturing system, the subsequent pair of images including the artificial target in a subsequent high energy image and a subsequent low energy image, applying the high energy gain map to the subsequent high energy image to create a high-gain normalized high energy image, applying the low energy gain map to the subsequent high energy image to create a low-gain normalized high energy image, and subtracting the low-gain normalized high energy image from the high-gain normalized high energy image to identify an artifact in the high-gain normalized high energy image In another aspect, the technology relates to a method for identifying an artifact induced by a change in a position of a focal spot of an x-ray tube. An example method includes receiving an initial pair of images from an image capturing system comprising the x-ray tube, the initial pair of images including an artificial target at a first position in an initial high energy image and an initial low energy image, generating a high energy gain map based on the initial high energy image, and generating a low energy gain map based on the initial low energy image. The method also includes receiving a subsequent pair of images from the image capturing system, the subsequent pair of images including the artificial target in a subsequent high energy image and a subsequent low energy image, applying the low energy gain map to the subsequent low energy image to create a low-gain normalized low energy image, applying the high energy gain map to the subsequent low energy image to create a high-gain normalized low energy image, and subtracting the high-gain normalized low energy image from the low-gain normalized low energy image to identify an artifact in the low-gain normalized low energy image.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Additional aspects, features, and/or advantages of examples will be set forth in part in the description which follows and, in part, will be apparent from the description, or may be learned by practice of the disclosure.

BRIEF DESCRIPTION OF THE DRAWINGS

Non-limiting and non-exhaustive examples are described with reference to the following figures.

DETAILED DESCRIPTION

Figure 1A:
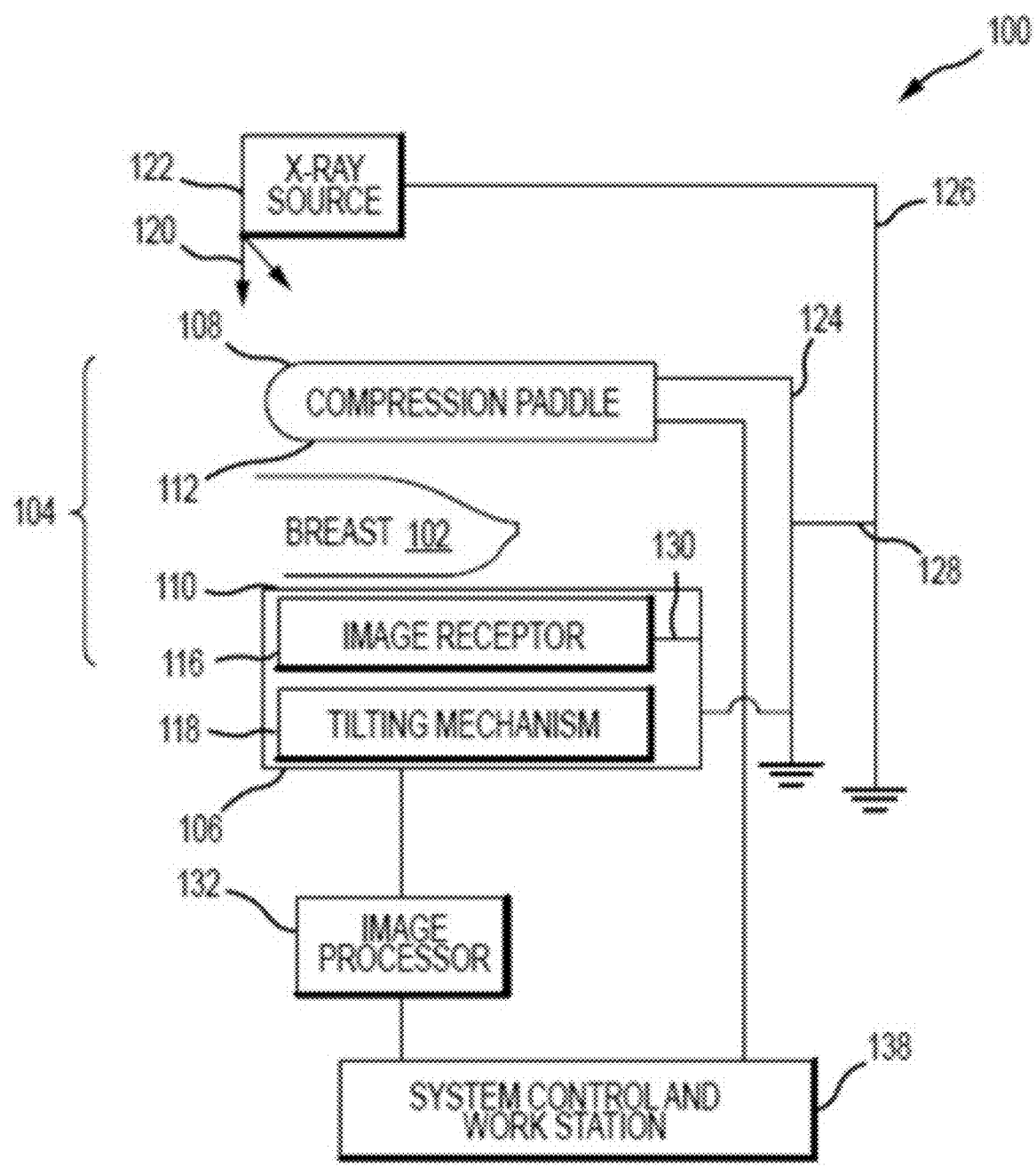
FIG. 1A is a schematic view of an example breast imaging system.

As discussed above, x-ray tubes in medical imaging systems are susceptible to an unstable focal spot position during successive image captures. The unstable focal spot position may be caused by heat generation during tube loading, where the heat increases over successive usage (e.g., successive image captures), and thus instability increases as the number of image captures increase. The change in focal spot position is uncertain and unpredictable from capture to capture. The unstable focal spot positions result in arbitrary projection paths for the x-ray beams that may cause any objects in the projection paths to be in different spatial locations among the successive images. Therefore, if the focal spot position has changed, when a gain map generated from an initial image is applied to a subsequent image to normalize the subsequent image, a spatial shift of the objects in the subsequent image may cause two sets of objects to be visualized in the normalized subsequent image rather than a blank, uniform image. For example, one set may be visualized at a first position of the objects in the initial image, while the other set may be visualized at a second position of the objects in subsequent image, as described in detail below.

In some examples, the spatial shift may cause the objects to manifest as artifacts in the normalized subsequent image. Additional factors in conjunction with the focal spot instability may contribute to the induction of artifacts. For example, other objects in the projection paths of the x-ray beams, such as an x-ray filter, a collimator blade tip, an anti-scatter grid, or carbon fiber material within the imaging system may appear differently (e.g., spatially shift) as successive images are captured. Among other examples, the change in focal spot position may cause a defect in the x-ray filter (e.g., a wrinkle) that forms an x-ray filter induced artifact. The change in focal spot position may also cause the collimator blade tip, based on its position, to induce a chest wall band artifact. These artifacts may reduce the diagnostic usefulness of the resultant medical images.

The technologies described herein relate to a method and system for tracking changes in focal spot position throughout successive images captures to overcome the challenges caused by the focal spot instability. For example, one or more artificial targets are captured in an initial image from which a gain map is generated. The artificial targets are further captured in subsequent images, and the artificial targets accounted for within the gain map may serve as references when the gain map is applied to the subsequent images to identify shifts in position of the artificial targets from the initial image to the subsequent image (e.g., in pixels). The shift may correspond to a change in position of the focal spot from capture of the initial image to capture of the subsequent image. Once the shift and corresponding position change are identified, one or more of mathematical corrections may be applied to the subsequent image and/or physical corrections may be applied to the system for future imaging to reduce or eliminate any undesirable artifacts and improve image quality for diagnostic evaluations.

In describing examples and embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Figure 1B:
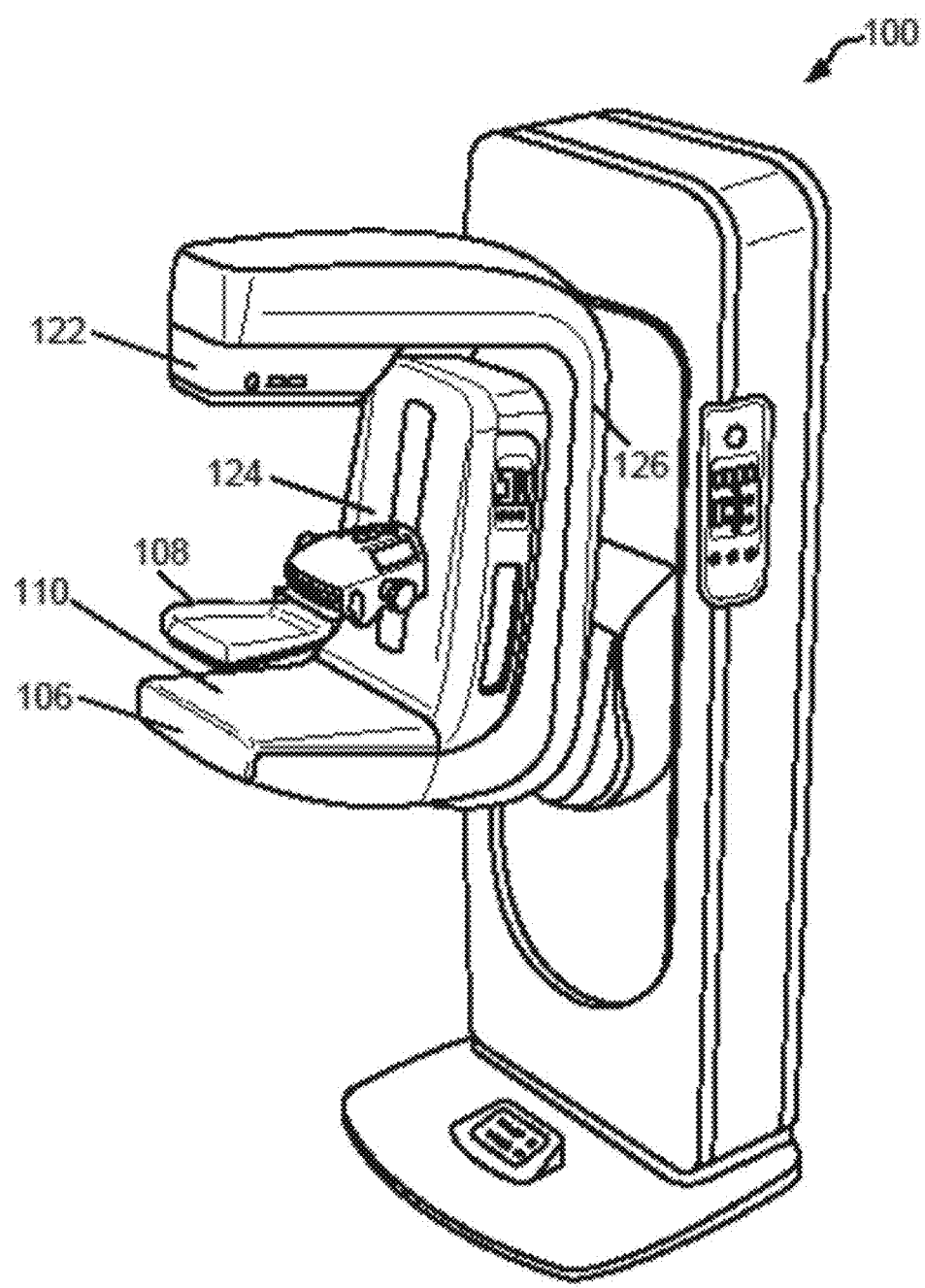
FIG. 1B is a perspective view of the breast imaging system of FIG. 1A.

FIG. 1A is a schematic view of an example breast imaging system 100. FIG. 1B is a perspective view of the breast imaging system 100. Referring concurrently to FIGS. 1A and 1B, the breast imaging system 100 immobilizes a patient's breast 102 for x-ray imaging (one or more of a mammography mode, a tomosynthesis mode, and a computed tomography (CT) mode) via a breast compression immobilizer unit 104 that includes a static breast support platform 106 and a moveable compression paddle 108. The breast support platform 106 and the compression paddle 108 each have a compression surface 110 and 112, respectively, that move towards each other to compress and immobilize the breast 102. In known systems, the compression surface 110, 112 is exposed so as to directly contact the breast 102. The breast support platform 106 also houses an image receptor 116 and, optionally, a tilting mechanism 118, and optionally an anti-scatter grid. The immobilizer unit 104 is in a path of an imaging beam 120 emanating from x-ray source 122, such that the beam 120 impinges on the image receptor 116.

The immobilizer unit 104 is supported on a first support arm 124 and the x-ray source 122 is supported on a second support arm 126. For mammography, support arms 124 and 126 can rotate as a unit about an axis 128 between different imaging orientations such as cranial-caudal (CC) and mediolateral oblique (MLO) views, so that the breast imaging system 100 can take a mammogram projection image at each orientation. In operation, the image receptor 116 remains in place relative to the breast support platform 106 while an image is taken. The immobilizer unit 104 releases the breast 102 for movement of arms 124, 126 to a different imaging orientation. For tomosynthesis, the support arm 124 stays in place, with the breast 102 immobilized and remaining in place, while at least the second support arm 126 rotates the x-ray source 122 relative to the immobilizer unit 104 and the compressed breast 102 about the axis 128. The breast imaging system 100 takes plural tomosynthesis projection images of the breast 102 at respective angles of the beam 120 relative to the breast 102.

Concurrently and optionally, the image receptor 116 may be tilted relative to the breast support platform 106 and in sync with the rotation of the second support arm 126. The tilting can be through the same angle as the rotation of the x-ray source 122, but may also be through a different angle selected such that the beam 120 remains substantially in the same position on the image receptor 116 for each of the plural images. The tilting can be about an axis 130, which can but need not be in the image plane of the image receptor 116. The tilting mechanism 118 that is coupled to the image receptor 116 can drive the image receptor 116 in a tilting motion. For tomosynthesis imaging and/or CT imaging, the breast support platform 106 can be horizontal or can be at an angle to the horizontal, e.g., at an orientation similar to that for conventional MLO imaging in mammography. The breast imaging system 100 can be solely a mammography system, a CT system, or a tomosynthesis system, or a "combo" system that can perform multiple forms of imaging. An example of such a combo system has been offered by the assignee hereof under the trade name Selenia Dimensions.

The breast imaging system 100 images the breast 102 by emitting an x-ray beam 120 from the x-ray source 122. In some examples, an x-ray filter may be placed between the x-ray source 122 and the breast 102 to control wavelengths present in the x-ray beam 120 in order to regulate an energy of the x-rays that pass through the breast 102. After passing through the filter, the x-ray beam 120 passes through the breast 102 where it is detected by the image receptor 116. The image receptor 116 may include a plurality of pixels that detect the intensity of the x-ray beam 120 at a plurality of locations after the x-ray beam has passed through the breast 102. The attenuation of the x-ray beam 120 as it passes through the breast 102 changes depending on the structures of the breast 102. Accordingly, images of the breast may be produced from the detected x-ray beam 120. For instance, the image receptor 116 produces imaging information in the form of electric signals, and supplies that imaging information to an image processor 132 for processing and generating x-ray images of the breast 102. A system control and work station unit 138 including software controls the operation of the system and interacts with the operator to receive commands and deliver information including images of the breast 102. The system control and work station unit 138 may also include software for controlling the operation of the x-ray source 122.

One challenge with the breast imaging system 100, particularly when x-ray imaging is a mode requiring successive image captures such as a contrast-enhanced digital mammography (CEDM) mode and a tomosynthesis mode, is focal spot instability throughout the successive image captures. Focal spot instability may degrade image quality and thus reduce the diagnostic usefulness of the resultant medical images. For example, the x-ray beam 120 may be generated through the use of the x-ray source 122 that includes an x-ray tube. As described in more detail with reference to FIG. 2, a voltage or signal may be applied across a filament of the x-ray tube causing electrons to be emitted from the filament. The emitted electrons form an electron beam that accelerates towards an anode of the x-ray tube. The electron beam impacts the anode, which causes the emission of x-rays from the anode that form the x-ray beam 120 used for imaging. The area in which the electron beam impacts the anode is referred to as the focal spot.

Figure 2:
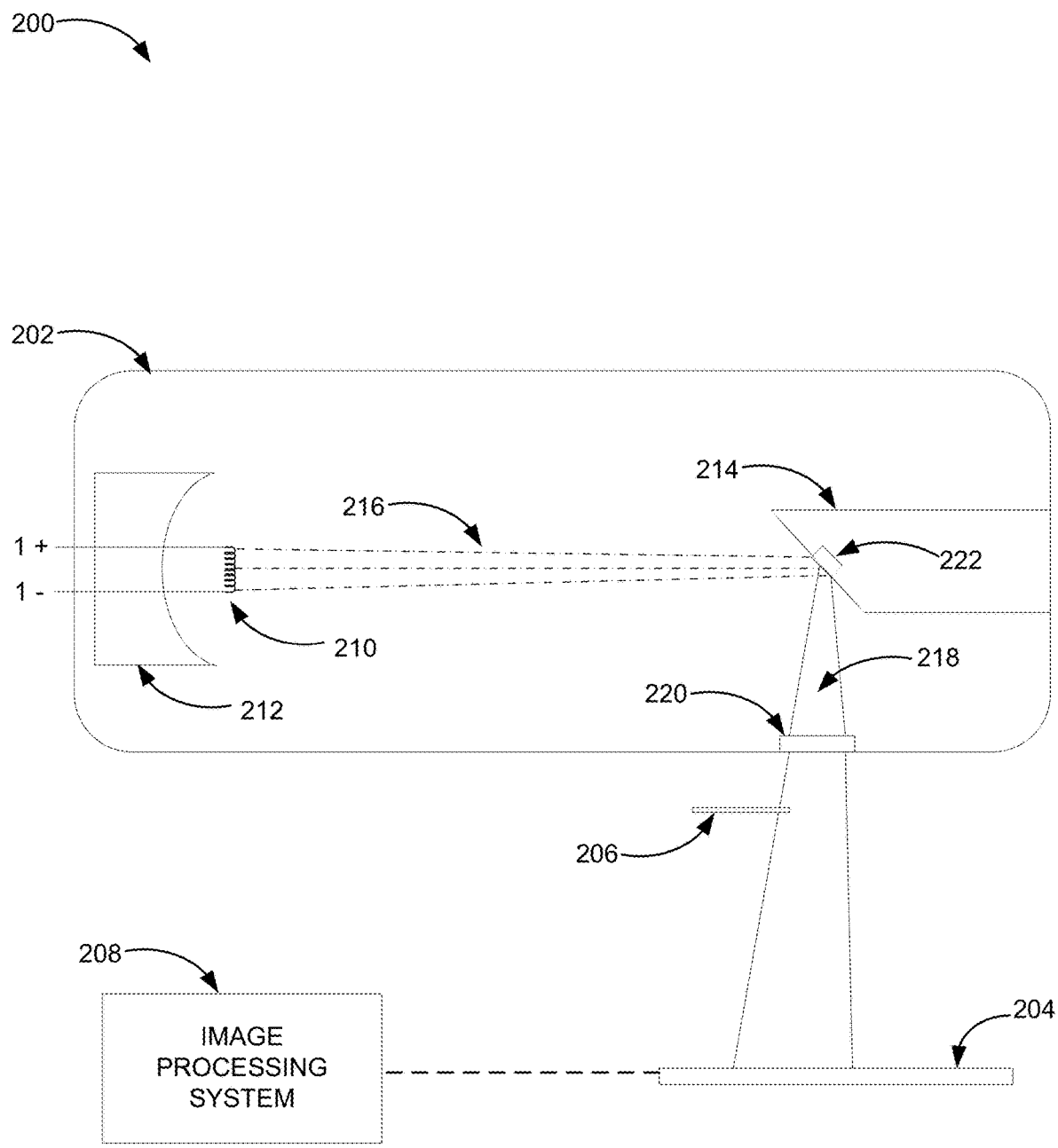
FIG. 2 is an example system for tracking a position of a focal spot of an x-ray tube.

FIG. 2 is an example system 200 for tracking a position of a focal spot of an x-ray tube. The system 200 may be a part of the breast imaging system 100 described with reference to FIGS. 1A and 1B. The system 200 may include an image capturing system comprising at least an x-ray tube 202 and a detector 204, at least one artificial target 206, and an image processing system 208.

The x-ray tube 202 may be included as at least part of the x-ray source 122 shown and described above with reference to FIGS. 1A and 1B. A body of the x-ray tube 202 houses a cathode assembly including at least one filament 210 and a focusing cup 212. The filament 210 may be placed adjacent to the focusing cup 212 and between the focusing cup 212 and an anode 214. The filament 210 may be made from a material with a high melting point, such as tungsten. A voltage or signal may be applied across the filament 210 via wires connected to each end of the filament 210, indicated by the 1+ for the positive connection to the filament 210 and the 1− for the negative connection to the filament 210. When the signal or voltage is applied across the filament 210, a current flows through the filament 210, which heats the filament 210 and causes electrons to be emitted from the filament 210. Due to a voltage difference between the cathode assembly and the anode 214, the electrons emitted from the filament 210 are accelerated towards the anode 214. The accelerated electrons form an electron beam 216 that travels along an electron beam path. The electron beam 216 impacts the anode 214, which causes the emission of x-rays 218 from the anode 214. The x-rays 218 exit the body of the x-ray tube 202 through a tube window 220. The x-rays 218 that exit through the window 220 form the x-ray beam that is used for imaging, such as x-ray beam 120 discussed above with reference to FIGS. 1A-1B.

The area in which the electron beam 216 impacts the anode 214 is referred to as the focal spot 222. The size of the focal spot 222 relates to the resolution desired for the imaging process. For instance, a small focal spot 222 may be used where high resolution of a small area is desired. The position of the focal spot 222 on the anode 214, as well as the angle of the anode 214, also has an effect on the direction of the x-rays 218 produced from the anode 214. The size and position of the focal spot 222 may be controlled or modified by the focusing cup 212. For instance, the focusing cup 212 may include a negative charge that repels the electrons emitted from the filament 210. That charge, the distribution of that charge, and the shape of the focusing cup 212 may be selected or configured to direct the electrons emitted from the filament 210 to the focal spot 222 on the anode 214.

The artificial target 206 may be composed of a material that highly attenuates x-rays, such as metal. One example type of metal that may be used is titanium. The artificial target may be a flexible strand or rod (e.g., a wire) of varying diameters. In some examples, the artificial target 206 may be arranged substantially parallel to an x-axis of the detector 204 and at least a portion of the artificial target 206 may be within a projection path of an x-ray beam formed from the x-rays 218. In other examples, the artificial target 206 may be arranged substantially parallel to a y-axis of the detector 204 and at least a portion of the artificial target 206 may be within a projection path of an x-ray beam formed from the x-rays 218. In further examples, the system 200 may include at least two artificial targets, as shown and described in FIG. 3. In yet further examples, the artificial target 206 may be a mesh object that is arranged to extend across an entirety of the window 220 of the x-ray tube 202, as shown and described with reference to FIG. 8. The artificial target 206 may be attached to the exterior of the body of the x-ray tube 202 or otherwise fastened to another component of the imaging system such that the artificial target 206 remains substantially stationary throughout the imaging process. In some examples, the artificial target 206 may be removable (e.g., detachable) from the body of the x-ray tube 202 and/or attached in a manner that the artificial target 206 may be moved in and out of the projection path of an x-ray beam.

The detector 204 may be included as at least part of the image receptor 116 shown and described above with reference to FIGS. 1A and 1B. The detector 204 may detect an x-ray beam formed from the x-rays 218 after the x-ray beam passes through at least a portion of the artificial target 206. The detector 204 may convert the attenuated x-ray beam into an electrical signal that is then converted to an image by the image processing system 208. For instance, the detector 204 may be a flat-panel digital x-ray detector that includes a plurality of pixels. Each pixel may capture a portion of the x-ray beam. The captured x-rays for each pixel may then be converted into an image having corresponding pixels. The image can include at least the portion of the artificial target 206 as the artificial target is located within the x-ray beam and positioned between the x-ray tube 202 and the detector 204. The image processing system may include at least the image processor 132 shown and described above with reference to FIGS. 1A and 1B.

Each time a new electron beam impacts the anode 214 (e.g., each time a signal or voltage is applied across the filament 210, causing electrons to be emitted from the filament 210 and form an electron beam that accelerates towards the anode 214), a position of the focal spot 222 may change. When the position of the focal spot 222 changes from one image capture to a next image capture, a projection path for the x-ray beam may correspondingly change causing any objects, such as the artificial target 206, in the respective projection paths to be different (e.g., spatially shifted) among the image captures. Resultantly, although the artificial target 206 is a substantially stationary target, a first position of the artificial target 206 in an initial image may be different than a second position of the artificial target 206 in a subsequent image.

The image processing system 208 may identify the shift of the artificial target 206 from the first position to the second position, where the shift corresponds to the change in the position of the focal spot 222 from the capture of the initial image to the capture of the subsequent image. Once the shift is identified, a current image (e.g., the subsequent image) can be adjusted to correct for the shift. For example, the subsequent image may be adjusted according to a same magnitude but opposite direction of the identified shift. Additionally or alternatively, the system 200 may also include an apparatus that is capable of controlling dimensions of an electron beam received at the anode 214, where the dimensions of the electron beam affect the position of the focal spot 222 on the anode 214. Therefore, a control signal may be generated that causes the apparatus to adjust the dimensions of the electron beam to reverse the change in the position of the focal spot 222 for subsequent imaging. Example apparatuses are described in detail below with reference to FIGS. 10-12.

Figure 3:
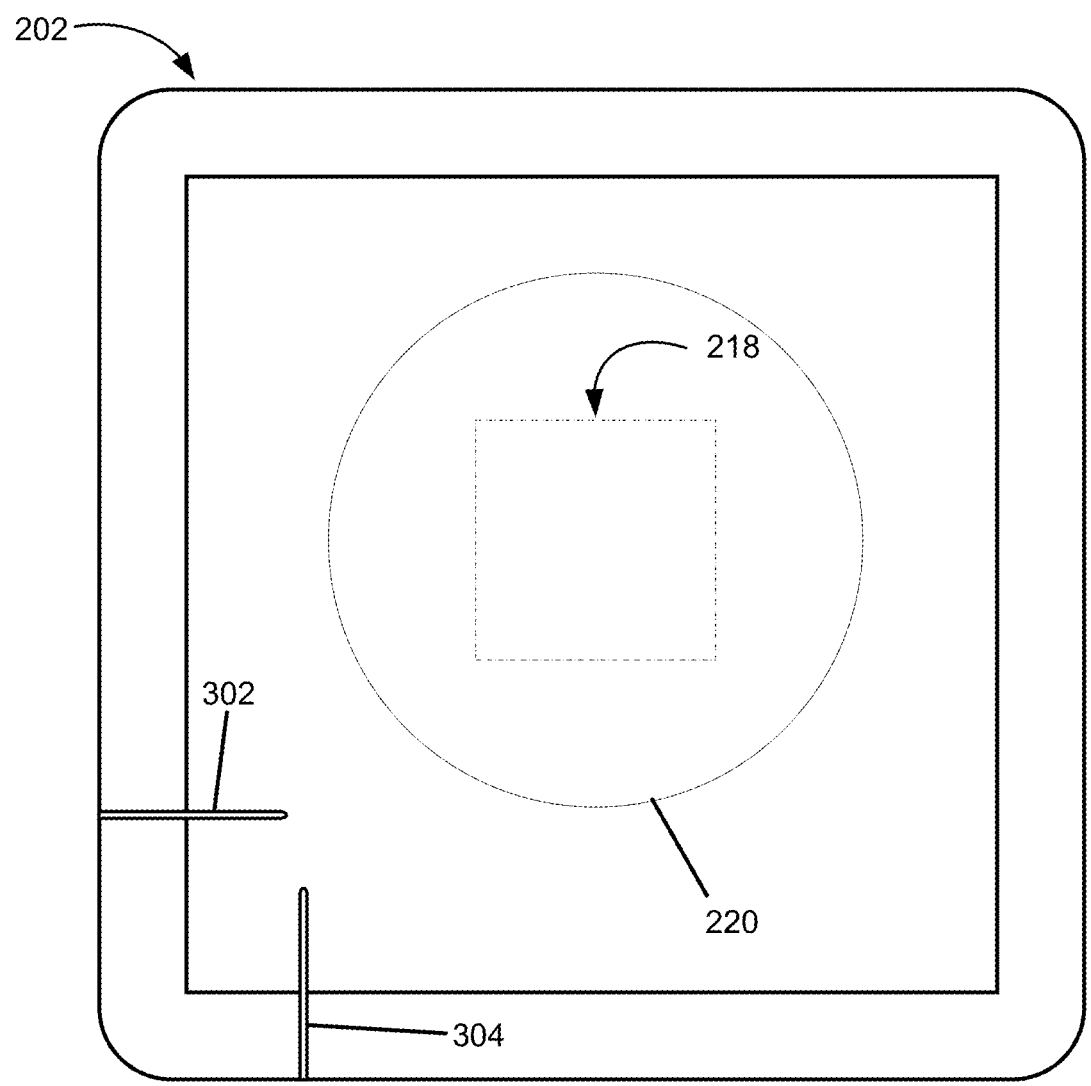
FIG. 3 is a view of an example arrangement of at least two artificial targets in the system shown and described in FIG. 2.

FIG. 3 is a view of an example arrangement of at least two artificial targets 302, 304 in a system for tracking a position of a focal spot of an x-ray tube 202. The system may be similar to the system 200, shown and described above with reference to FIG. 2, with the exception that the system includes two artificial targets 302, 304. The view is from the perspective of a detector, such as the detector 204 shown and described with reference to FIG. 2, looking up towards the body of the x-ray tube 202.

The first artificial target 302 and the second artificial target 304 may be arranged relative to the tube window 220 of the x-ray tube 202 and the detector. As one example, the first artificial target 302 and the second artificial target 304 may be arranged such that the x-rays 218 exiting the body of the x-ray tube 202 through the tube window 220 form an x-ray beam that passes through at least a portion of the artificial targets 302, 304 for detection by the detector. In other words, the artificial targets 302, 304 may be arranged such that at least a portion of each of the artificial targets 302, 304 is within a projection path of the x-ray beam. The detector may convert the attenuated x-ray beam into an electrical signal that is then converted to an image by an image processing system, such as the image processing system 208 shown and described with reference to FIG. 2. The image may include the portions of first artificial target 302 and the second artificial target 304 that are within the x-ray beam path.

In some examples, the first artificial target 302 may be arranged in a first direction and the second artificial target 304 may be arranged in a second direction. As one example, the first direction may be substantially parallel to an x-axis of the detector and the second direction may be parallel to a y-axis of the detector. As described above with reference to FIG. 2, a position of the focal spot of the anode may change each time a new electron beam impacts the anode (e.g., each time a new image is to be captured). A projection path for an x-ray beam formed by the x-rays 218 emitted from the anode may correspondingly change causing any objects, such as the first artificial target 302 and the second artificial target 304, in the respective projection path to be different (e.g., spatially shifted) among the image captures. Resultantly, a position of the first artificial target 302 and the second artificial target 304 in an initial image may be different than a position of the first artificial target 302 and the second artificial target 304 in a subsequent image.

The image processing system may identify a shift of the first artificial target 302 from a first position in the initial image to a second position in the subsequent image. The shift may correspond to a change in the position of the focal spot in the second direction. For example, continuing the above example where the first artificial target 302 is arranged in a first direction that is substantially parallel to the x-axis of the detector, the image processing system may identify the shift along a second direction that is substantially parallel to the y-axis of the detectors and thus, the change in the position of the focal spot along the y-axis.

Similarly, the image processing system may identify a shift of the second artificial target 304 from a first position in the initial image to a second position in the subsequent image. The shift may correspond to a change in the position of the focal spot in the first direction. For example, continuing the above example where the second artificial target 304 may be arranged in a second direction that is substantially parallel to the y-axis of the detector, the image processing system may identify the shift along a first direction that is substantially parallel to the x-axis of the detector and thus, the change in the position of the focal spot along the x-axis.

Additional details for identifying the shift in position of the first artificial target 302 and the second artificial target 304 from the capture of the initial image to the capture of the subsequent image is discussed with reference to FIGS. 4A-B, 5 and 6 below.

Figure 4A:
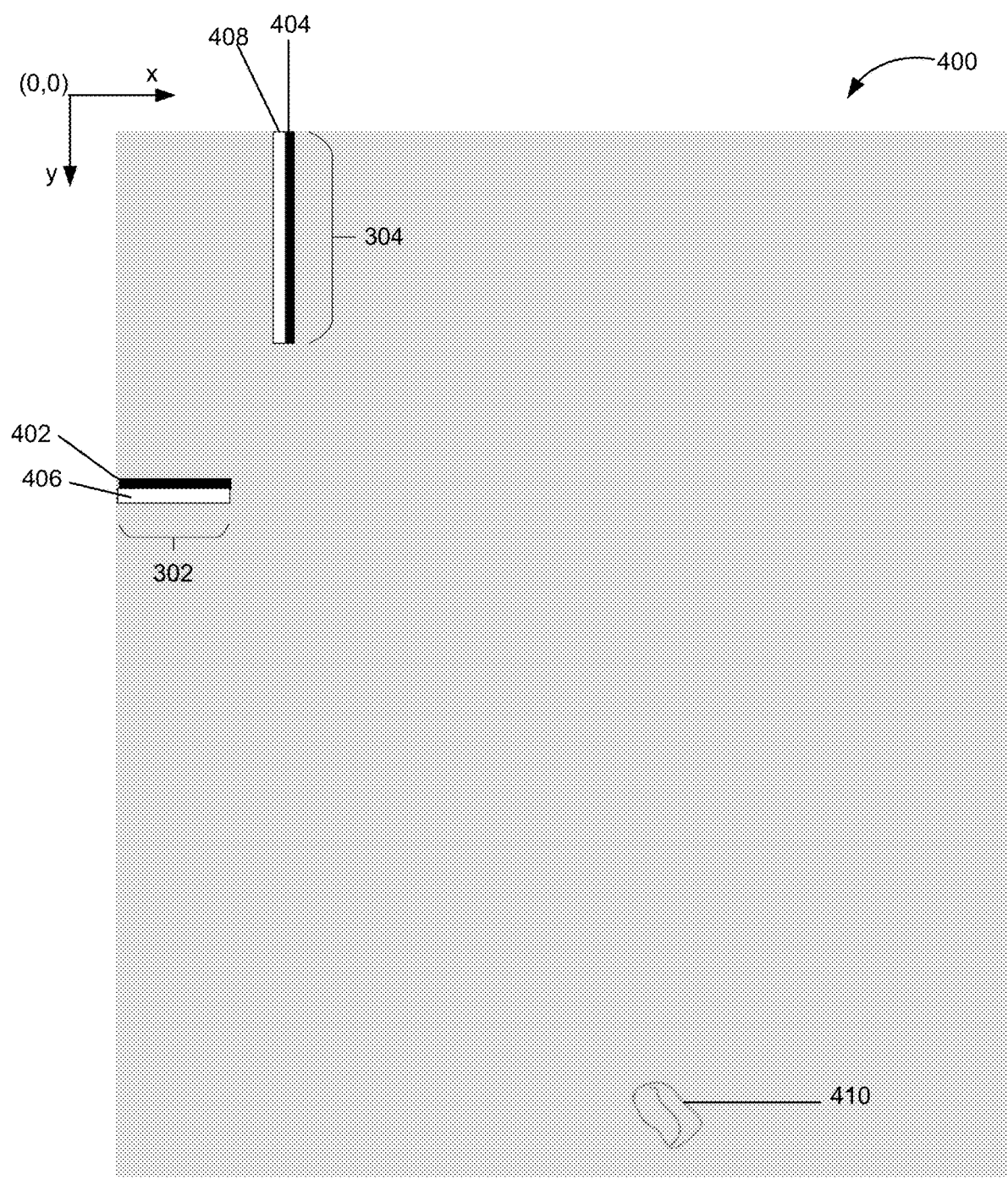
FIG. 4A is an example representation of a normalized subsequent image when a focal spot position has changed.
Figure 4B:
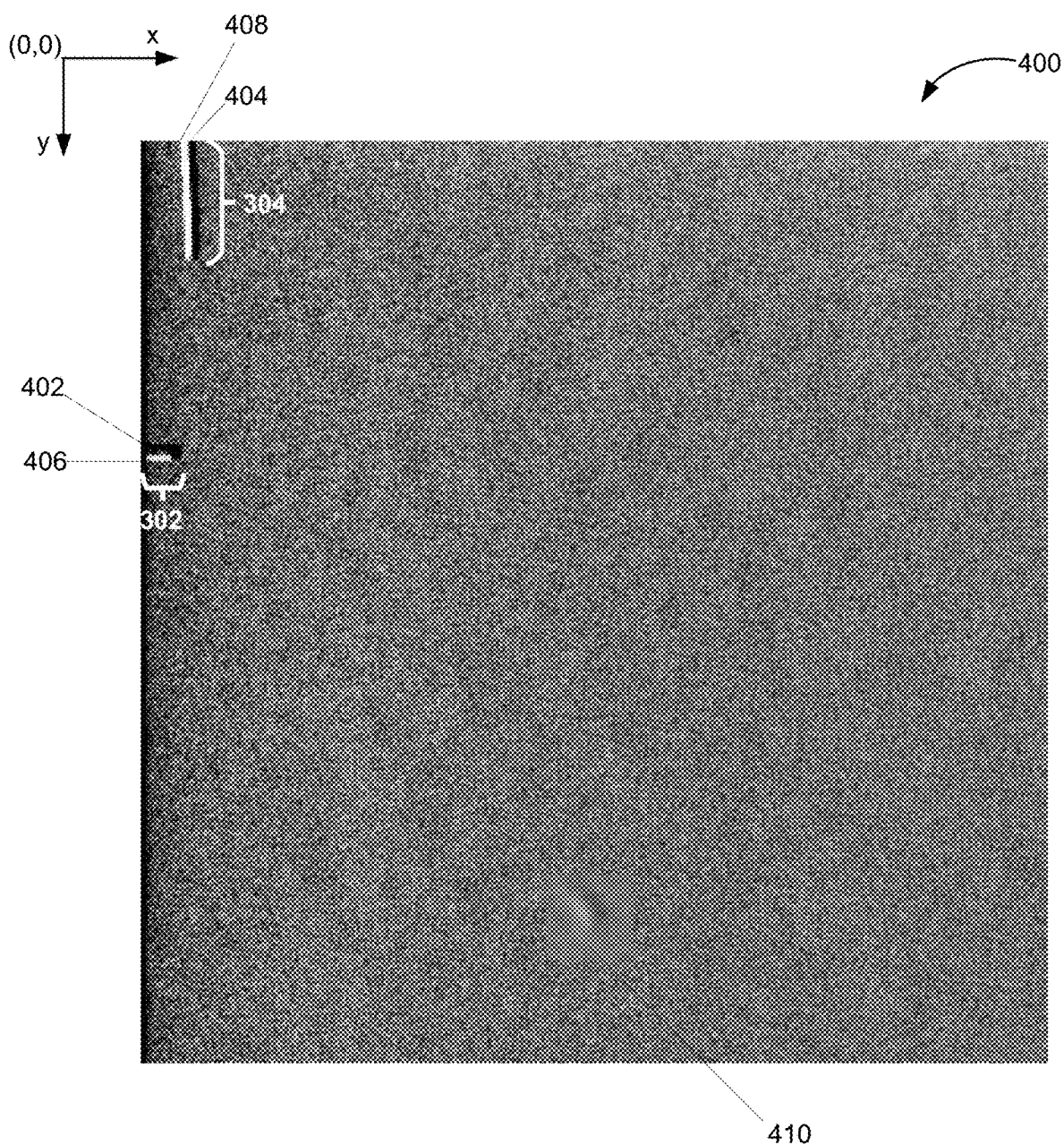
FIG. 4B is an example of an actual normalized subsequent image from which the representation in FIG. 4A is based.

FIG. 4A illustrates an example representation of a normalized subsequent image 400 when a focal spot position has changed. FIG. 4B depicts the normalized subsequent image 400 from which the representation in FIG. 4A is based. Referring concurrently to FIGS. 4A and 4B, the image 400 may be generated by a system that is similar to the system 200 shown and described with reference to FIG. 2, with the exception that it includes at least a first artificial target 302 and a second artificial target 304 as shown and described with reference to FIG. 3. The image processing system may receive an initial image from the image capturing system for use in gain map generation, as described further below. In some examples, the initial image may be an Automatic Exposure Control (AEC) Scout image. The initial image may include the first artificial target 302 and the second artificial target 304 at respective positions in the initial image.

In some examples, initial image data that is received from the detector of the image capturing system may be in a raw format, such as pixels. For example, the detector may include a plurality of pixels, and there may be inherent differences (e.g., different amplification gains and offsets) in the response of different pixels to the x-ray beam detected at the detector. In some examples, there are variances between pixel values that the pixels provide, even when exposed to the same x-ray input. Additionally, incident x-ray intensity across the detector surface may be non-uniform due to the "heel effect", for example, leading to further variances between pixel values that the pixels provide. To equalize or correct for the variances in pixel values, gain calibration and image correction techniques may be employed.

As one example of gain calibration, a gain map may be generated on a pixel-by-pixel basis to equalize or correct for the variances in pixel values recorded in the initial image data. For example, in an initial captured image, a median pixel intensity value for all the pixels of the detector may be determined. For each individual pixel, a ratio of the median intensity value to a value of the respective pixel may yield a coefficient that is applied to the respective pixel to correct the respective pixel (e.g., to equalize the intensity value of the pixel each of the other pixels). The collection of those coefficients for each pixel may be referred to as a gain map. A gain map may be generated for each type of exposure mode (e.g., for each type of filter applied for CEDM as discussed further with reference to FIGS. 15 and 16). In some examples, a new gain map may be generated at predetermined time intervals. In further examples, particularly when tomosynthesis imaging is implemented, the gain map may be generated using techniques described in commonly assigned U.S. Pat. No. 7,991,106, which is hereby incorporated by reference in its entirety. These techniques are provided merely as examples, and those having skill in the art will recognize and understand additional or different techniques for generating a gain map.

When the x-rays within the x-ray beam are projected from the focal spot to the detector, the artificial targets 302, 304 block the x-rays attempting to pass therethrough and prevent these x-rays from reaching the detector. Accordingly, in the initial image data that is received from the detector, the pixels corresponding to the respective positions of the artificial targets 302, 304 in the initial image may appear white due to lower pixel intensity values than the surrounding imaged environment resulting from the artificial targets 302, 304 blocking the x-rays from reaching the detector. Accordingly, when generating a gain map based on the initial image, the pixel intensity values corresponding to the respective positions of the artificial targets 302, 304 in the initial image will be lower than the median pixel intensity value for all the pixels. Therefore, the coefficients in the gain map for the pixels corresponding to the respective positions of the first artificial target 302 and the second artificial target 304 in the initial image will be a value greater than one to increase intensity (e.g., to equalize intensity with other pixels), or another type of value that compensates for the presence of the first artificial target 302 and the second artificial target 304.

The gain map may be stored in memory of the image processing system and applied to subsequent images that are received to normalize the subsequent images. Normalization may involve correction of pixel values according to the gain map to bring the pixel values in the subsequent image closer to the pixel values that would have been produced if all the pixels had the same response to uniform exposure to the x-ray beam. Additionally, the coefficients in the gain map for the pixels corresponding to the respective positions of the artificial targets 302, 304 in the initial image may serve as references for an initial position of the focal spot during the capture of the initial image, and thus application of the gain map can identify whether the focal spot position has changed or not.

As one example, a subsequent image including the artificial targets 302, 304 may be received. Similar to the initial image, the artificial targets 302, 304 in the subsequent image may appear white due to lower pixel intensity values associated with the artificial targets 302, 304 than the surrounding imaged environment. The gain map generated from the initial image can then be applied to correct for these lower pixel intensity values such that the pixel intensity values will be equal across all pixels (e.g., equal one) forming a blank, uniform image as the normalized subsequent image. However, this equalization is dependent on the respective positions of the artificial targets 302, 304 in the initial image from which the gain map was generated not changing in the subsequent image such that the coefficients of the gain map, when applied, may align with the corresponding pixels to create the blank, uniform image.

If the position of the focal spot has not changed from the capture of the initial image and the subsequent image, the projection paths for the x-ray beams may be maintained such that the artificial targets 302, 304 remain in a same respective position in the subsequent image as the initial image. Thus, the application of the gain map causes the proper coefficients to be applied to the pixels corresponding the artificial targets 302, 304 in the subsequent image. As a result, the pixel intensity values will be equal across all pixels (e.g., equal one) forming the blank, uniform image as the normalized subsequent image. In other words, the artificial targets 302, 304 will not be visible in the normalized subsequent image.

Alternatively, if the focal spot has changed from the capture of the initial image and the subsequent image, the projection paths for the x-ray beams may be different causing the artificial targets 302, 304 to be in different positions in the subsequent image. Resultantly, when the gain map generated from the initial image is applied, the coefficients for the pixels corresponding to the respective positions of the artificial targets 302, 304 in the initial image do not align with the pixels corresponding to the position of the artificial targets 302, 304 in the subsequent image, which prevents the blank, uniform image from forming. Rather the coefficients are applied to pixels in the subsequent image that are of a higher pixel intensity value (e.g., applied to pixels corresponding to areas where x-rays were not blocked from reaching detector). As a result of applying the coefficients, which are values greater than one, to pixels in the subsequent image that are of a higher pixel intensity value, phantom targets that appear overcompensated (e.g., that are black in color) are visible in the normalized subsequent image. The phantom targets are present at the first position of the artificial targets 302, 304 in the initial image from which the gain map was generated. Additionally, because the coefficients are not being applied to the pixels corresponding to the positions of the artificial targets 302, 304 in the subsequent image, the artificial targets 302, 304 maintain their white appearance in the normalized subsequent image and are present at the second position of the artificial targets 302, 304 in the subsequent image. Thus, two sets of the artificial targets 302, 304 are visible in the normalized subsequent image, one set corresponding to the position of the artificial targets 302, 304 in the initial image and the other set corresponding to the position of the artificial targets 302, 304 in the subsequent image.

The image 400 is an example of the normalized subsequent image when the focal spot position has changed. The image 400 shows a first position 402 of the first artificial target 302 and a first position 404 of the second artificial target 304 in the initial image from which the gain map was generated (e.g. the phantom targets), as well as a second position 406 of the first artificial target 302 and a second position 408 of the second artificial target 304 in the subsequent image.

The image processing system may identify a shift of the first artificial target 302 from the first position 402 to the second position 406, where the shift corresponds to a change in the position of the focal spot from the capture of the initial image to the capture of the subsequent image. When the first artificial target 302 is arranged substantially parallel to the x-axis of the detector, as illustrated, the shift identified is along the y-axis, and thus the shift corresponds to a focal spot position change along the y-axis. To identify the shift, a profile plot is generated, as shown and described with reference to FIG. 6.

Additionally, the image processing system may identify a shift of the second artificial target 304 from the first position 404 to the second position 408, where the shift corresponds to a change in the position of the focal spot from the capture of the initial image to the capture of the subsequent image. When the second artificial target 304 is arranged substantially parallel to the y-axis of the detector, as illustrated, the shift identified is along the x-axis, and thus the shift corresponds to a focal spot position change along the x-axis. To identify the shift, a profile plot is generated, as shown and described with reference to FIG. 5.

The changes in focal spot position may induce artifacts that degrade a quality of the image 400. In conjunction with focal spot position changes, other factors, may contribute to the induction of artifacts. For example, other objects in the projection paths of the x-ray beams, such as an x-ray filter, a collimator blade tip, an anti-scatter grid, or carbon fiber material of the breast support platform 106, may appear differently (e.g., spatially shift) as successive images are captured. As one example, the change in focal spot position may cause a defect in the x-ray filter (e.g., a wrinkle) forming an x-ray filter induced artifact, such as artifact 410. As another example, a position of collimator blade tip may result in a chest wall band artifact. Degradation of image quality caused by artifacts, such as the artifact 410, may reduce the diagnostic usefulness of the resultant medical images.

By identifying the shift of the artificial targets 302, 304, the image 400 can be adjusted to account for the shift and remove the artifact 410. For example, the image 400 can be adjusted according to a same magnitude but opposite direction of the shift. Additionally or alternatively, the changes in the position of the focal spot determined based on the shift can be reversed for subsequent imaging by utilizing an apparatus of the system that is capable of controlling dimensions of an electron beam received at the anode, where the dimensions of the electron beam affect the position of the focal spot. In other examples, dependent on a type of imaging implemented, methods described in detail with reference to FIGS. 15 and 16 may be performed to remove the x-ray filter induced artifact 410 from the image 400.

Figure 5:
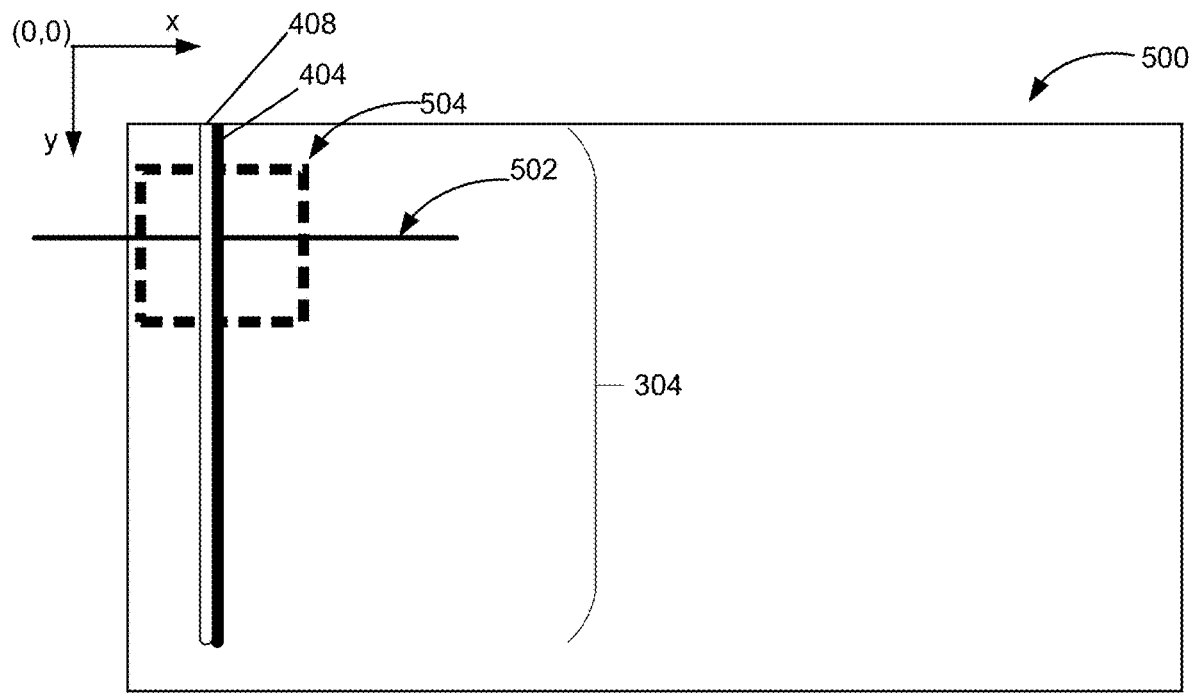
FIG. 5 illustrates a profile plot generated to identify a shift in position of an artificial target along an x-axis.
Figure 5:
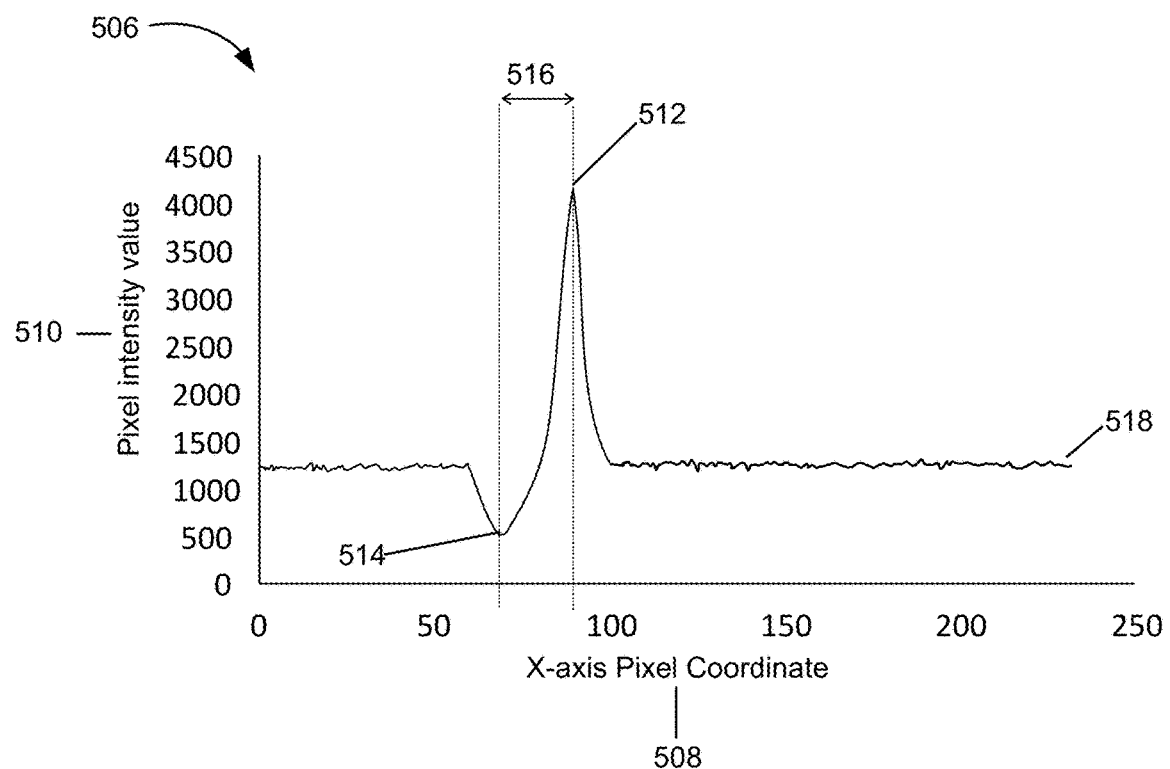

FIG. 5 illustrates a profile plot generated to identify a shift in position of an artificial target along an x-axis. Image 500 may be a portion of the image 400 shown and described with reference to FIGS. 4A and 4B (e.g., a portion of the normalized subsequent image). Image 500 includes the second artificial target 304 that is arranged substantially parallel to the y-axis of the detector, enabling identification of the shift in position of the second artificial target 304 along a direction that is substantially parallel to the x-axis of the detector (e.g., enable identification of a shift along the x-axis). A profile plot 506 may be generated along a line 502 intersecting the second artificial target 304 in a region 504 of the image 500. As illustrated, a direction of the line 502 may be along the x-axis.

The profile plot 506 may include pixel intensity values for a predefined range of pixels in the region 504 along the direction of the line 502. For example, the x-axis 508 of the profile plot 506 may include the predefined range of pixels along the x-axis (e.g., a range of x-axis pixel coordinates), and the y-axis 510 of the profile plot 506 may include pixel intensity values corresponding to each pixel within the predefined range of pixels. Within the predefined range of pixels, a local maximum and a local minimum and the pixel intensity values thereof may be identified. For example, a first pixel 512 having a local maximum pixel intensity value and a second pixel 514 having a local minimum pixel intensity value may be identified.

In some examples, identifying the local maximum and the local minimum may further include determining a median pixel intensity value 518 for the predefined range of pixels, where the pixels having local maximum and minimum intensity values are greater than or less than the median pixel intensity value 518, respectively, by at least a threshold value. For example, the first pixel 512 having the local maximum pixel intensity value may have a pixel intensity value greater than the median pixel intensity value 518 by at least a threshold value. The second pixel 514 having the local minimum pixel intensity value may have a pixel intensity value less than the median pixel intensity value 518 by at least a threshold value.

In some examples, local maxima and local minima may be identified using parsing methods, such as C++ or two-dimensional (2D) array parsing methods. For example, a 2D region of interest (ROI) for both the artificial targets 302, 304 may be known. Because there are only the artificial targets 302, 304 in the fixed regions, the minimum and the maximum from a row or column of the fixed 2D ROI is easily identified via parsing the 2D array. With respect to FIG. 5 specifically, the 2D ROI for the second artificial target 304 may be parsed to identify the first pixel 512 having the local maximum pixel intensity value and the second pixel 514 having the local minimum pixel intensity value from a row of the fixed 2D ROI.

In other examples, local maxima and local minima may be identified through data analytics algorithms. For example, the findpeaks function and the islocalmin functions available in the MATLAB software product available from The MathWorks, Inc. of Natick, Mass., are capable of identifying local maxima and minima as well as the values for those local maxima and minima. Additionally, the findpeaks function and the islocalmin functions may be capable of identifying local maxima and minima that satisfy threshold value requirements using prominence measurements (e.g., prominence of a peak or valley measures how much the peak or valley stands out due to its intrinsic height and its location relative to other peaks or valleys). These functions are provided merely as examples, and those having skill in the art will recognize and understand additional or different techniques for identifying maxima and minima within sets of data.

As described in greater detail with reference to FIGS. 4A and 4B, when the focal spot position has changed from the initial image capture to the subsequent image capture, the position of the second artificial target 304 changes from the first position 404 to the second position 408. Therefore, when the gain map generated from the initial image is applied to the subsequent image to generate the normalized subsequent image (e.g., image 500), the gain map coefficients for the pixels corresponding to the first position 404 of the second artificial target 304 in the initial image do not align with the pixels corresponding to the second position 408 of the second artificial target 304 in the subsequent image, which prevents a blank, uniform image from forming in the image 500. Rather the gain map coefficients for the pixels corresponding to the first position 404 of the second artificial target 304, which are values greater than one, are applied to pixels in the subsequent image that are of a higher pixel intensity value. As a result, a phantom target having an overcompensated appearance (e.g., due to the higher intensity value comparative to the median pixel intensity value 518) is visible in the image 500 at the first position 404 of the second artificial target 304. Accordingly, the first pixel 512 having the local maximum pixel intensity value in the profile plot 506 may correspond to the first position 404. Additionally, because the gain map coefficients for the pixels corresponding to the first position 404 of the second artificial target 304 are not being applied to the pixels corresponding to the position of the second artificial target 304 in the subsequent image, the second artificial target 304 maintains a white appearance (e.g., due to a lower intensity value comparative to the median pixel intensity value 518) in the image 500 at the second position 408 of the second artificial target 304. Accordingly, the second pixel 514 having the local minimum pixel intensity value in the profile plot 506 may correspond to the second position 408 of the second artificial target 304.

Once the pixels corresponding to the local maximum and the local minimum are identified (e.g., the first pixel 512 and the second pixel 514, respectively), a pixel distance 516 between the first pixel 512 and the second pixel 514 may be determined. The pixel distance 516 may represent the shift (in pixels) of the position of the second artificial target 304 along the x-axis from the initial image to the subsequent image.

Figure 6:
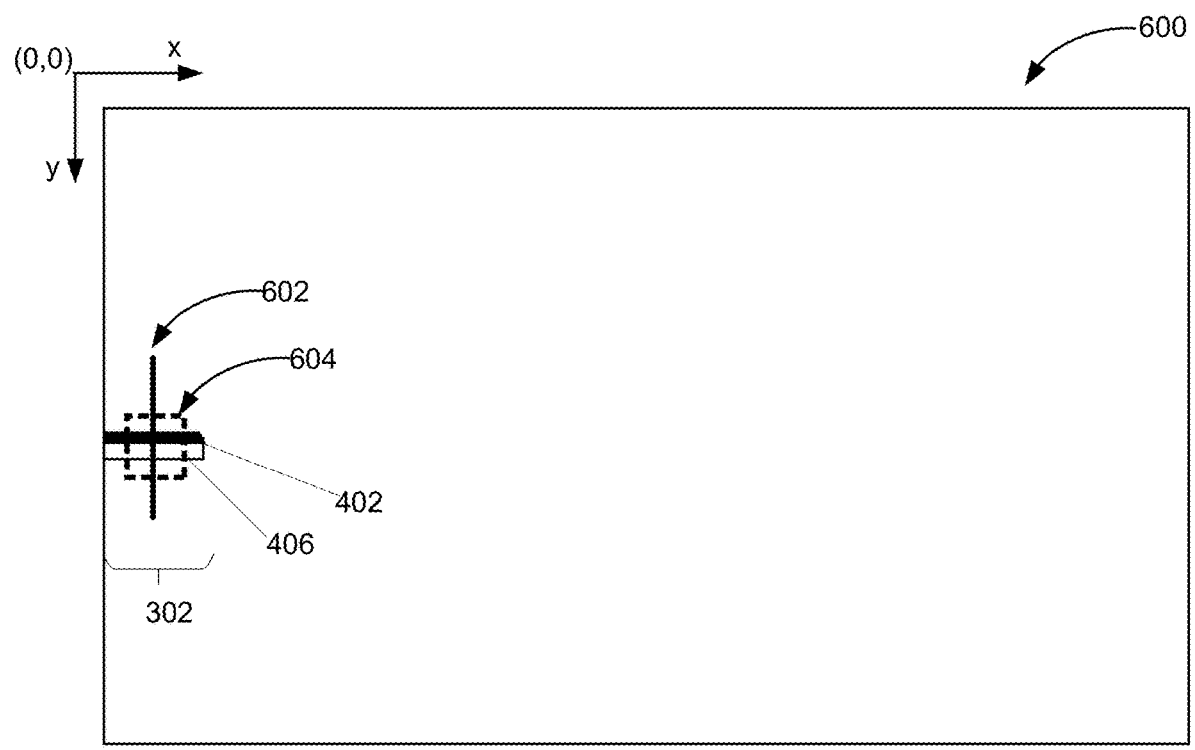
FIG. 6 illustrates a profile plot generated to identify a shift in position of an artificial target along a y-axis.
Figure 6:
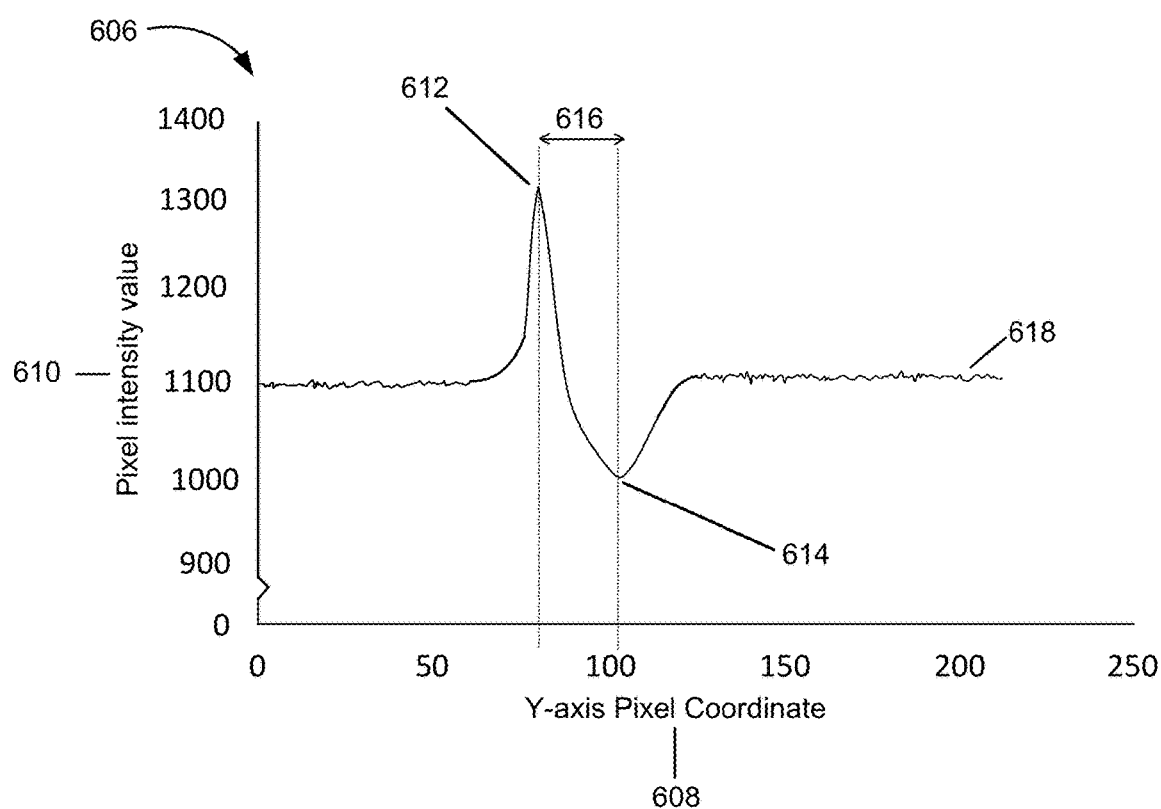

FIG. 6 illustrates a profile plot generated to identify a shift in position of an artificial target along a y-axis. Image 600 may be a portion of the image 400 shown and described with reference to FIGS. 4A and 4B (e.g., a portion of the normalized subsequent image). Image 600 includes the first artificial target 302 that is arranged substantially parallel to the x-axis of the detector, enabling identification of the shift in position of the first artificial target 302 along a direction that is substantially parallel to the y-axis of the detector (e.g., enabling identification of a shift along the y-axis). A profile plot 606 may be generated along a line 602 intersecting the first artificial target 302 in a region 604 of the image 600. As illustrated, a direction of the line 602 may be along the y-axis.

The profile plot 606 may include pixel intensity values for a predefined range of pixels in the region 604 along the direction of the line 602. For example, the x-axis 608 of the profile plot 606 may include the predefined range of pixels along the y-axis (e.g., a range of y-axis pixel coordinates), and the y-axis 610 of the profile plot 606 may include pixel intensity values corresponding to each pixel within the predefined range of pixels. Within the predefined range of pixels, a local maximum and a local minimum and the pixel intensity values thereof may be identified. For example, a first pixel 612 having a local maximum pixel intensity value and a second pixel 614 having a local minimum pixel intensity value may be identified. As previously discussed with reference to FIG. 5, the local maxima and local minima may be identified using parsing methods. With respect to FIG. 6 specifically, the 2D ROI for the first artificial target 302 may be parsed to identify the first pixel 612 having the local maximum pixel intensity value and the second pixel 614 having the local minimum pixel intensity value from a column of the fixed 2D ROI. Alternatively, the local maxima and local minima may be identified through data analytics algorithms. Additionally, in some examples, identifying the local maximum and the local minimum may further include determining a median pixel intensity value 618 for the predefined range of pixels, where the pixels having local maximum and minimum intensity values are greater than or less than the median pixel intensity value 618, respectively, by at least a threshold value.

As described in greater detail with reference to FIGS. 4A and 4B, when the focal spot position has changed from the initial image capture to the subsequent image capture, the position of the artificial target 302 changes from the first position 402 to the second position 406. Therefore, when the gain map generated from the initial image is applied to the subsequent image to generate the normalized subsequent image (e.g., image 600), the gain map coefficients for the pixels corresponding to the first position 402 of the artificial target 302 in the initial image do not align with the pixels corresponding to the second position 406 of the artificial target 302 in the subsequent image, which prevents a blank, uniform image from forming in the image 600. Rather the gain map coefficients for the pixels corresponding to the first position 402 of the artificial target 302 in the initial image, which are values greater than one, are applied to pixels in the subsequent image that are already of a higher pixel intensity value. As a result, a phantom target having an overcompensated appearance (e.g., due to the higher intensity value comparative to the median pixel intensity value 618) is visible in the image 600 at the first position 402 of the artificial target 302. Accordingly, the first pixel 612 having the local maximum pixel intensity value in the profile plot 606 may correspond to the first position 402. Additionally, because the gain map coefficients for the pixels corresponding to the first position 402 of the artificial target 302 in the initial image are not being applied to the pixels corresponding to the position of the artificial target 302 in the subsequent image, the artificial target 302 maintains a white appearance (e.g., due to a lower intensity value comparative to the median pixel intensity value 618) in the image 600 at the second position 406 of the artificial targets 302. Accordingly, the second pixel 614 having the local minimum pixel intensity value in the profile plot 606 may correspond to the second position 406 of the first artificial target 302.

Once the pixels corresponding to the local maximum and the local minimum are identified (e.g., the first pixel 612 and the second pixel 614, respectively), a pixel distance 616 between the first pixel 612 and the second pixel 614 may be determined. The pixel distance 616 may represent the shift (in pixels) of the position of the first artificial target 302 from the initial image to the subsequent image along the y-axis.

In some examples, once the pixel distance 516 representing the shift of the second artificial target 304 along the x-axis, shown and described with reference to FIG. 5, and the pixel distance 616 representing the shift of the first artificial target 302 along the y-axis are determined, an entirety of the image 400 may be adjusted based on the pixel distance 516 and the pixel distance 616 to correct for the shift along the x-axis and the y-axis, respectively. The image may be corrected in the x- and y-axes according to a same magnitude but opposite direction of the identified shifts. For example, if the pixel distance 516 is determined to be 21 pixels in a negative direction along the x-axis and the pixel distance 616 is determined to be 22 pixels in a negative direction along the y-axis, the image 400 may be shifted 21 pixels in a positive direction along the x-axis and 22 pixels in the positive direction along the y-axis. In other examples, the gain map generated based on the initial image may be adjusted based on the pixel distance 516 and the pixel distance 616, and reapplied to the subsequent image to generate a new normalized subsequent image.

Additionally, the pixel distance 516 may correspond to a change in position of the focal spot along the x-axis and the pixel distance 616 may correspond to a change in position of the focal spot along the y-axis. In further examples, the pixel distance 516 may be converted to a first focal spot shift vector representing the change in the position of the focal spot along the x-axis, and the pixel distance 616 may be converted to a second focal spot shift vector representing the change in the position of the focal spot along the y-axis, as described in greater detail with reference to FIG. 7 below. A control signal may then be generated based on the first and second focal spot shift vectors for transmission to an apparatus of the system that is capable of controlling dimensions of an electron beam received at the anode of the x-ray tube. For example, dimensions of the electron beam may affect the position of the focal spot on the anode, and thus the control signal may cause the apparatus to adjust the dimensions of the electron beam to reverse the change in the position of the focal spot along the x-axis and y-axis for subsequent imaging.

Figure 7:
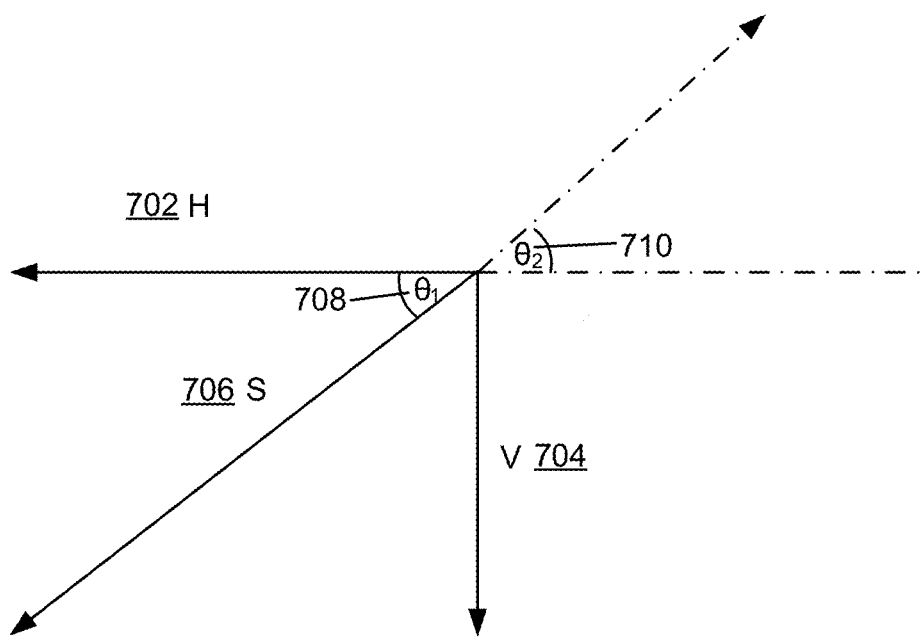
FIG. 7 illustrates example focal spot shift vectors.

FIG. 7 illustrates example focal spot shift vectors. A pixel distance representing the shift of the second artificial target along the x-axis may be determined as described with reference to FIG. 5. The pixel distance may correspond to a change in position of the focal spot along the x-axis. The pixel distance may be a magnitude of a first focal spot shift vector (H) 702. The first focal spot shift vector (H) 702 may have one of a positive or a negative direction along the x-axis. As illustrated in FIG. 7, the first focal spot shift vector (H) 702 may have a negative direction along the x-axis. The positive or negative direction may be based on a position of the first pixel where the local maximum occurs (e.g., a peak) relative to the second pixel where the local minimum occurs (a valley). For example, if the first pixel has a higher x-axis coordinate value than the second pixel causing the valley to occur to the left of the peak, such as first pixel 512 and second pixel 514 in FIG. 5, the first focal spot shift vector (H) 702 may have a negative direction along the x-axis. Alternatively, if the first pixel has a lower x-axis coordinate value than the second pixel causing the peak to occur to the left of the valley, the first focal spot shift vector (H) 702 may have a positive direction along the x-axis.

A pixel distance representing the shift of the first artificial target along the y-axis may be determined as described with reference to FIG. 6. The pixel distance may correspond to a change in position of the focal spot along the y-axis. The pixel distance may be a magnitude of a second focal spot shift vector (V) 704. The second focal spot shift vector (V) 704 may have one of a positive or a negative direction along the y-axis. As illustrated in FIG. 7, the second focal spot shift vector (V) 704 may have a negative direction along the y-axis. The positive or negative direction may be based on a position of the first pixel where the local maximum occurs (e.g., a peak) relative to the second pixel where the local minimum occurs (a valley). For example, if the first pixel has a lower y-axis coordinate value than the second pixel causing the peak to occur to the left of the valley, such as first pixel 612 and second pixel 614 in FIG. 6, the second focal spot shift vector (V) 704 may have a negative direction along the y-axis. Alternatively, if the first pixel has a higher y-axis coordinate value than the second pixel along the y-axis causing the valley to occur to the left of the peak, the first focal spot shift vector (H) 702 may have a positive direction along the y-axis.

A resultant focal spot shift vector (S) 706 may be determined based on the first focal spot shift vector (H) 702 and the second focal spot shift vector (V) 704. For example, to determine the resultant focal spot shift vector (S) 706, the Pythagorean Theorem may be applied (e.g., $S^2=H^2+V^2$). As one example, when H is 21 pixels and V is 22 pixels, $S^2=21^2+22^2$, therefore $S=\sqrt{(441+484)}=30.41$ pixels. The resultant focal spot shift vector 706 (S) may be converted from pixels to another distance unit (e.g., micrometers) at the focal spot using a multiplier. For example, each pixel has a defined width and length that may be measured in micrometers.

A first angle (θ1) 708 associated with the resultant focal spot shift vector (S) 706 may be determined based on the first focal spot shift vector (H) 702 and the second focal spot shift vector (V) 704. For example, tan $(\theta_1)$=V/H represents a direction of the resultant focal spot shift vector (S) 706, and therefore $\theta_1=\tan^{-1}$ (V/H). Continuing the above example, when H is 21 pixels and V is 22 pixels, $\theta_1=\tan^{-1}$ (22/21)=46.33°.

A control signal may then be generated based on the first angle $(\theta_1)$ 708 for transmission to an apparatus of the system, shown and described with reference to FIGS. 10-12, that is capable of controlling dimensions of an electron beam received at the anode of the x-ray tube. The dimensions of the electron beam affect the position of the focal spot on the anode, and therefore, the control signal may cause the apparatus to adjust the dimensions of the electron beam to reverse the change in the position of the focal spot along the x-axis and the y-axis. For example, a second angle $(\theta_2)$ 710 congruent to the first angle $(\theta_1)$ 708 may be identified. The second angle $(\theta_2)$ 710 may have a same measure in degrees (e.g., 46.33°) but is in an opposite direction to enable reversal of the change of the position of the focal spot. The control signal may cause the apparatus to adjust the dimensions of the electron beam by the magnitude and direction of the second angle $(\theta_2)$ 710.

Figure 8:
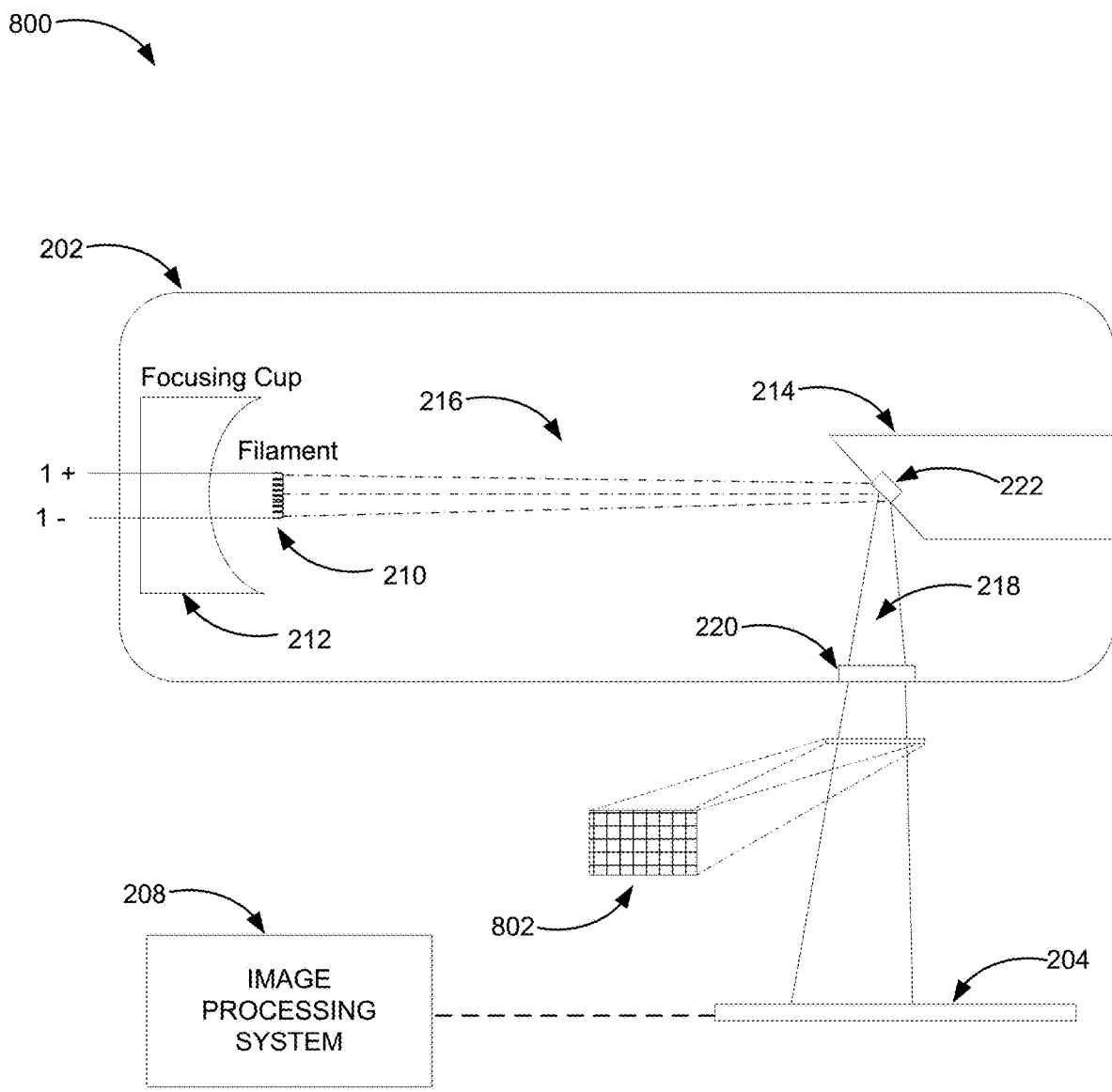
FIG. 8 is an example system having a mesh object artificial target for tracking a position of a focal spot of an x-ray tube.

FIG. 8 is an example system 800 having a mesh object artificial target 802 for tracking a position of a focal spot 222 of an x-ray tube 202. In some examples, the system 800 may be utilized for calibration, as discussed in greater detail below. The system 800 is similar to the system 200 shown and described with reference to FIG. 2, with the exception of a type of artificial target implemented by the system 800. For example, the artificial target in system 800 may be a mesh object artificial target 802.

The mesh object artificial target 802 may be arranged relative to the tube window 220 and the detector 204 to extend along an x-axis and a y-axis across an entirety of the tube window 220. In some examples, the mesh object artificial target 802 may be formed from connected strands of metal (e.g., wires) or other material that highly attenuates x-rays. As one example, the strands can be connected to form a grid pattern. For example, a first set of strands may be arranged substantially parallel to the y-axis of the detector 204 and extend across an entirety of the tube window 220, while a second set of strands may be arranged substantially parallel to the x-axis of the detector 204 and extend across an entirety of the tube window 220. The mesh object artificial target 802 or at least a portion of the strands thereof may be attached to the body of the x-ray tube 202 or otherwise positioned such that the mesh object artificial target 802 remains stationary throughout the imaging process. In some examples, the mesh object artificial target 802 may be removable (e.g., detachable) from the body of the x-ray tube 202 and/or attached in a manner that the mesh object artificial target 802 may be moved in and out of the projection path of an x-ray beam.

Each time a new electron beam impacts the anode 214 (e.g., each time a signal or voltage is applied across the filament 210, causing electrons to be emitted from the filament 210 and form an electron beam that accelerates towards the anode 214), a position of the focal spot 222 may change. When the position of the focal spot 222 changes from one image capture to another, a projection path for the x-ray beam may correspondingly change causing any objects, such as the mesh object artificial target 802, in the respective projection paths to be different (e.g., spatially shifted) among the image captures. Resultantly, although the mesh object artificial target 802 is a substantially stationary target, a first position of the mesh object artificial target 802 in an initial image may be different than a second position of the mesh object artificial target 802 in a subsequent image due to the focal spot shift. The image processing system 208 may identify the shift of the mesh object artificial target 802 from the first position to the second position, where the shift corresponds to the change in the position of the focal spot 222.

In some examples, the shift of the mesh object artificial target 802 may be identified on a per-strand basis. For example, the shift may be identified for each strand of the first set of strands in the mesh object artificial target 802 that are positioned substantially parallel to the y-axis of the detector 204. Additionally, the shift may be identified for each strand of the second set of strands in the mesh object artificial target 802 that are positioned substantially parallel to the x-axis of the detector 204. In some examples, shifts may be identified throughout the entirety of the image, however the value or rate of the shifts identified for the respective strands may be different based on the x-axis or y-axis position of the strands relative to an apex of the focal spot.

Figure 9A:
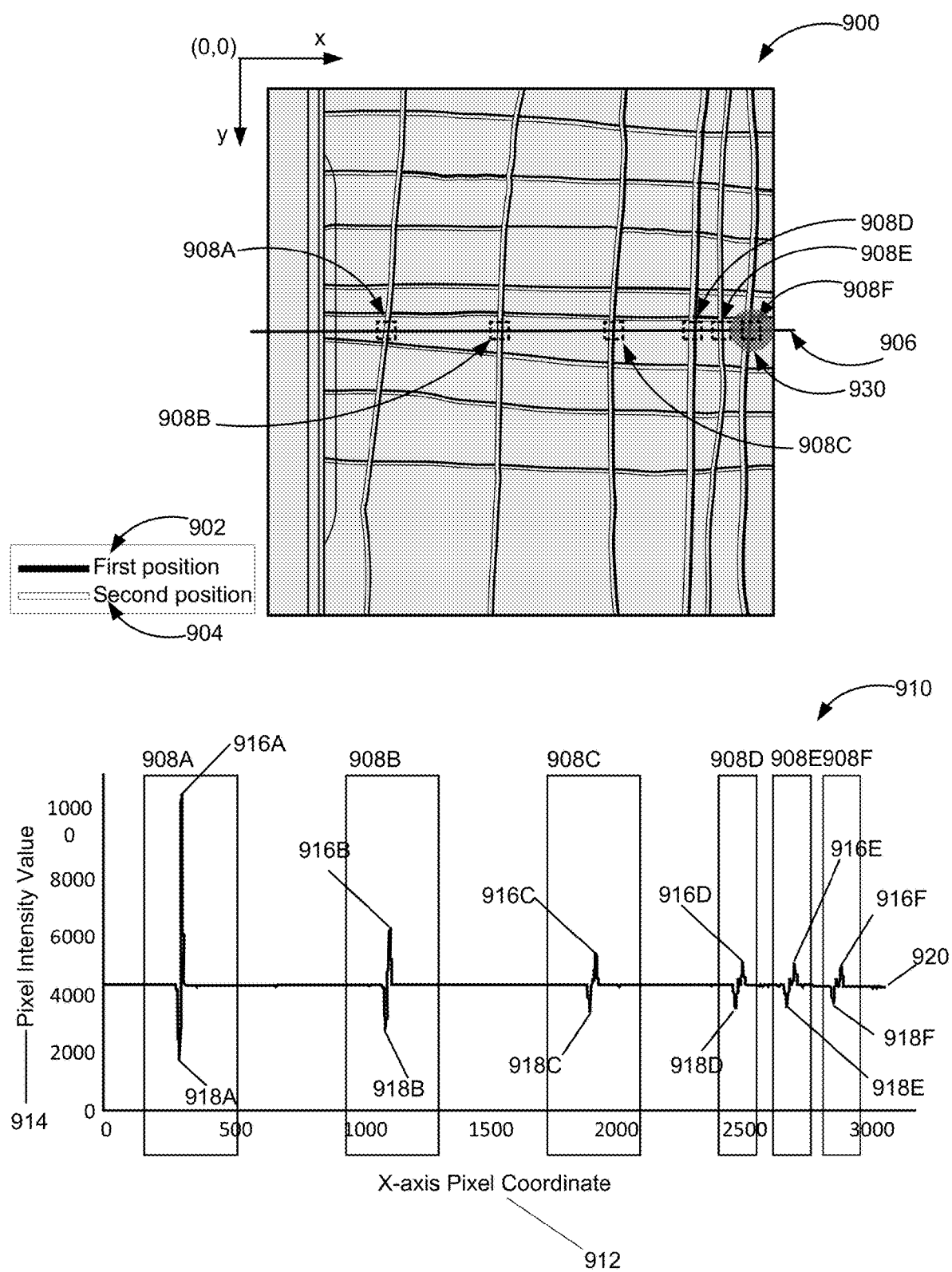
FIG. 9A illustrates an example representation of a normalized subsequent image when a focal spot position has changed and a corresponding profile plot generated to identify a shift in position of a mesh object artificial target along an x-axis.
Figure 9B:
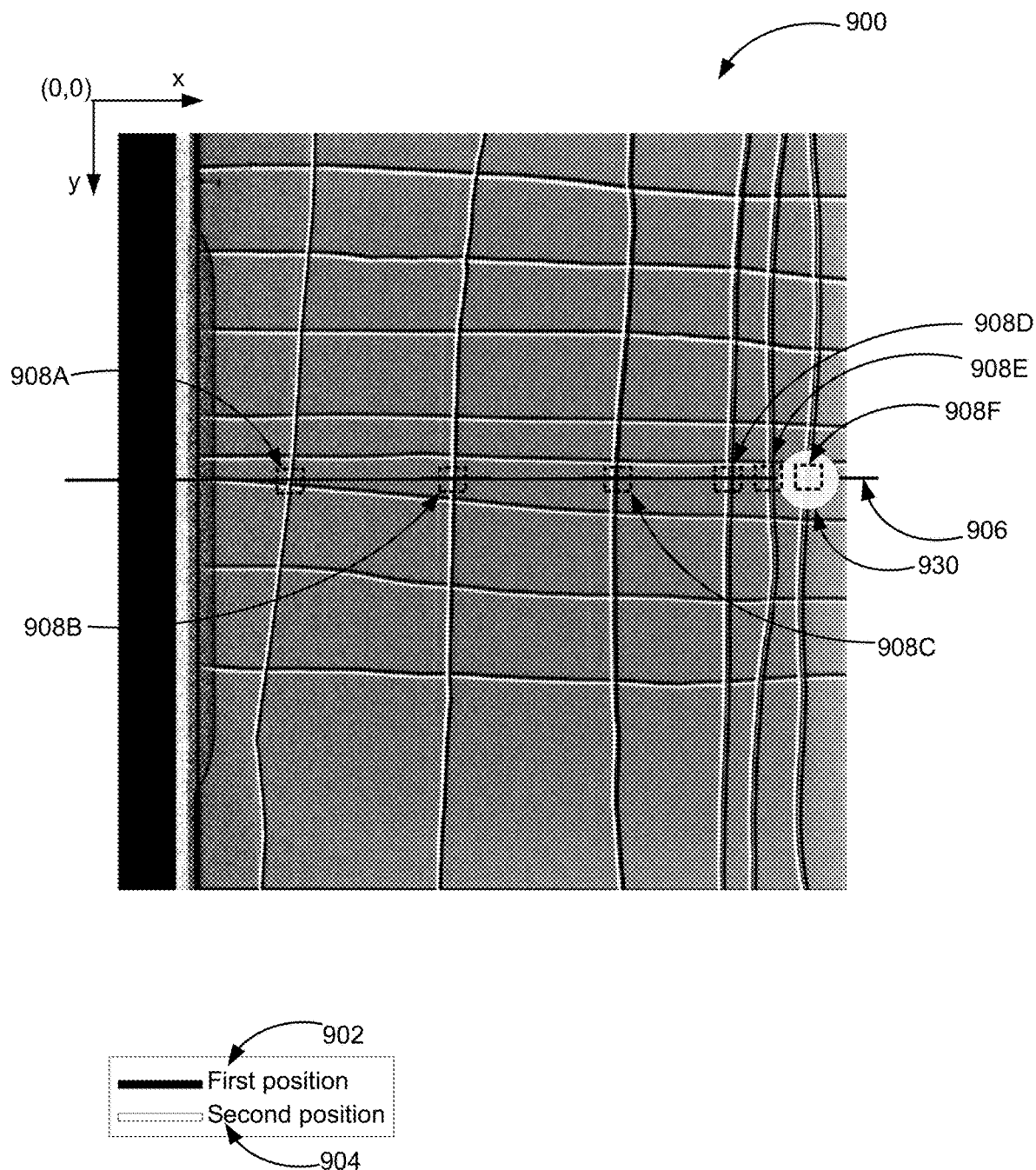
FIG. 9B is an example of an actual normalized subsequent image from which the representation in FIG. 9A is based.

FIG. 9A illustrates an example representation of a normalized subsequent image 900 when a focal spot position has changed, and a corresponding profile plot 910 generated to identify a shift in position of a mesh object artificial target along an x-axis. FIG. 9B depicts the normalized subsequent image 900 from which the representation in FIG. 9A is based. Referring concurrently to FIGS. 9A and 9B, the image 900 may be generated by the system 800 having a mesh object artificial target 802 as shown and described with reference to FIG. 8. For example, the image processing system may receive an initial image from the image capturing system. The initial image may include the mesh object artificial target 802 at a respective position in the initial image. A gain map may be generated based on the initial image, and applied to a subsequently received image that includes the mesh object artificial target 802 to generate a normalized subsequent image. The gain map may be generated and applied in a similar manner described above with reference to FIGS. 4A and 4B, where application of the gain map may identify whether the focal spot position during the capture of the initial image and the capture of the subsequent image has changed.

The image 900 is an example of the normalized subsequent image when the focal spot position has changed. When the focal spot changes, the projection paths for the x-ray beams may be different causing the mesh object artificial target 802 to be in different positions in the subsequent image For example, the mesh object artificial target 802 is at a first position in the initial image versus a second position in the subsequent image. As a result, when the gain map generated from the initial image is applied to the subsequent image, two sets of the mesh object artificial target 802 are visualized in the normalized subsequent image, where one set is at the first position and the other set is at the second position for reasons further detailed with reference to FIGS. 4A and 4B. For example, the image 900 shows a first position 902 of the mesh object artificial target 802 in the initial image from which the gain map was generated (e.g., the phantom targets), as well as a second position 904 of the mesh object artificial target 802 in the subsequent image. Had there been no change to the focal spot position, the mesh object artificial target 802 would not be visible in the normalized subsequent image resulting in a blank, uniform image for reasons further detailed with reference to FIGS. 4A and 4B.

The image processing system may identify a shift of the mesh object artificial target 802 from the first position 902 to the second position 904 along a direction substantially parallel to the x-axis of the detector (e.g., along the x-axis). The shift corresponds to a change in the position of the focal spot along the x-axis from the capture of the initial image to the capture of the subsequent image. In some examples, the shift may be identified on a per-strand basis. For example, a shift may be identified for each strand of the first set of strands in the mesh object artificial target 802 that are positioned substantially parallel to the y-axis of the detector.

To identify the shift, the profile plot 910 may be generated along a line 906 intersecting each strand of the first set of strands in respective regions 908A, 908B, 908C, 908D, 908E, and 908F, collectively regions 908, of the image 900. As illustrated, a direction of the line 906 may be along the x-axis.

The profile plot 910 may include pixel intensity values for a predefined range of pixels in each of the regions 908 along the direction of the line 906. For example, the x-axis 912 of the profile plot 910 may include the predefined range of pixels along the x-axis, and the y-axis 914 of the profile plot 910 may include pixel intensity values corresponding to each pixel within the predefined range of pixels. Within the predefined range of pixels for each of the regions 908, a first pixel 916 having a local maximum pixel intensity value and a second pixel 918 having a local minimum pixel intensity value may be identified. For example, first pixels 916A, 916B, 916C, 916D, 916E, and 916F may correspond to a local maximum pixel intensity value for the respective regions 908A, 908B, 908C, 908D, 908E, and 908F. Second pixels 918A, 918B, 918C. 918D, 918E, and 918F may correspond to a local minimum pixel intensity value for the respective regions 908A, 908B, 908C, 908D, 908E, and 908F.

As previously discussed with reference to FIGS. 5 and 6, local maxima and local minima may be identified through parsing methods or data analytics algorithms. Additionally, in some examples, identifying pixels having local maximum and minimum intensity values may further include determining a median pixel intensity value 920 for the predefined range of pixels, where the pixels having local maximum and minimum intensity values are greater than or less than the median pixel intensity value 920, respectively, by at least a threshold value.

A pixel distance between the first pixel 916 and the second pixel 918 may be determined for each of the regions 908. The pixel distance may represent the shift (in pixels) of the particular strand of the mesh object artificial target 802 corresponding to the region 908 from the capture of the initial image to the capture of the subsequent image. As described in greater detail below following the description of FIGS. 10A and 10B, the value or rate of the shifts identified for the respective strands (e.g., a pixel distance between the first pixel 916 and the second pixel 918 for each of the regions 908) are different based on the x-axis coordinate position of the strands relative to an apex of the focal spot.

Figure 10A:
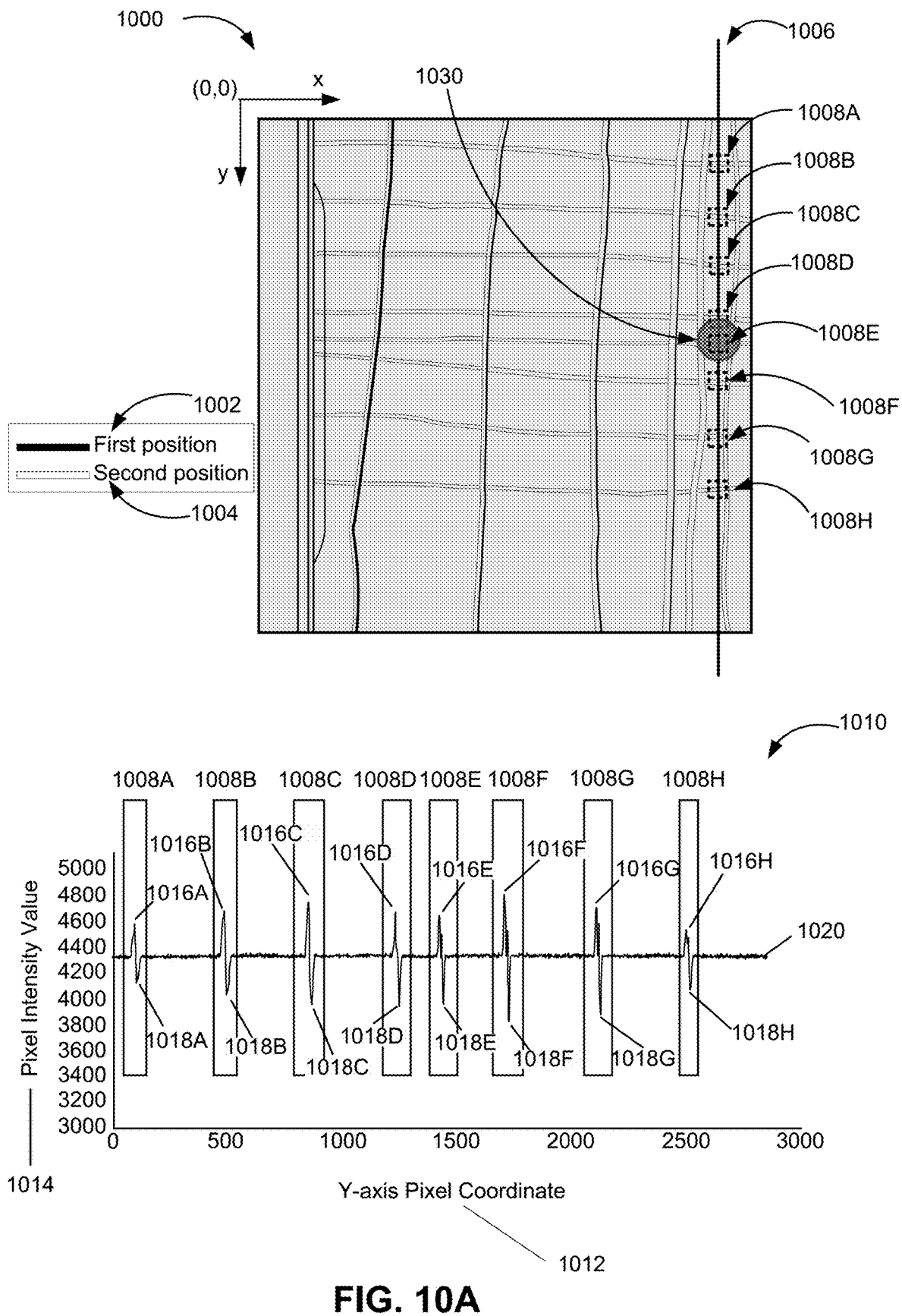
FIG. 10A illustrates an example representation of a normalized subsequent image when a focal spot position has changed and a corresponding profile plot generated to identify a shift in position of a mesh object artificial target along a y-axis.
Figure 10B:
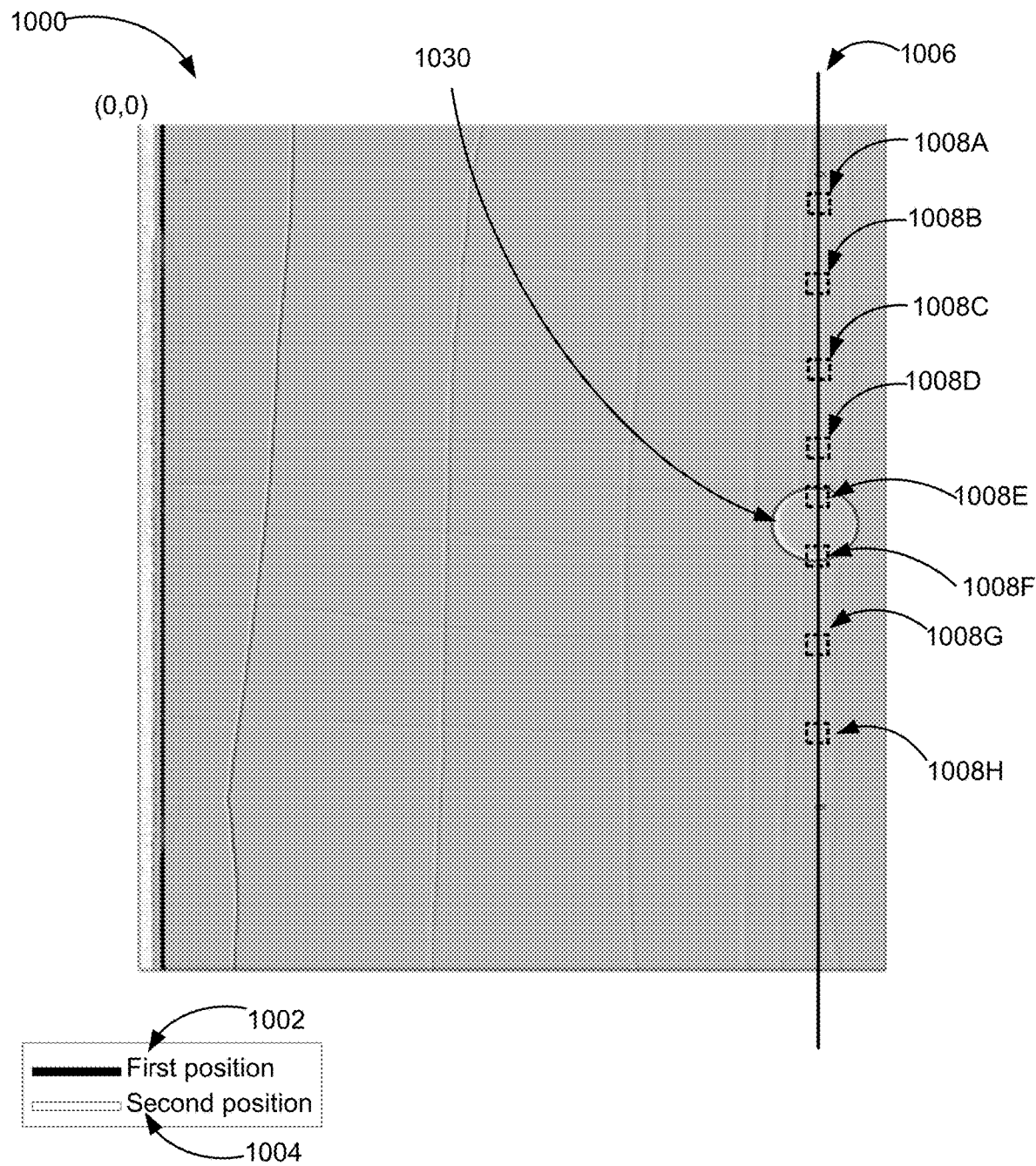
FIG. 10B is an example of an actual normalized subsequent image from which the representation in FIG. 10A is based.

FIG. 10A illustrates an example representation of a normalized subsequent image when a focal spot position has changed and a corresponding profile plot generated to identify a shift in position of a mesh object artificial target along a y-axis. FIG. 10B is an example of an actual normalized subsequent image from which the representation in FIG. 10A is based.

Referring concurrently to FIGS. 10A and 10B, the image 1000 may be generated by the system 800 having a mesh object artificial target 802 as shown and described with reference to FIG. 8. For example, the image processing system may receive an initial image from the image capturing system. The initial image may include the mesh object artificial target 802 at a respective position in the initial image. A gain map may be generated based on the initial image, and applied to a subsequently received image that includes the mesh object artificial target 802 to generate a normalized subsequent image. The gain map may be generated and applied in a similar manner described above with reference to FIGS. 4A and 4B, where application of the gain map may identify whether the focal spot position during the capture of the initial image and the capture of the subsequent image has changed.

The image 1000 is an example of the normalized subsequent image when the focal spot position has changed. When the focal spot changes, the projection paths for the x-ray beams may be different causing the mesh object artificial target 802 to be in different positions in the subsequent image. For example, the mesh object artificial target 802 is at a first position in the initial image versus a second position in the subsequent image. As a result, when the gain map generated from the initial image is applied to the subsequent image, two sets of the mesh object artificial target 802 are visualized in the normalized subsequent image, where one set is at the first position and the other set is at the second position for reasons further detailed with reference to FIGS. 4A and 4B. For example, the image 1000 shows a first position 1002 of the mesh object artificial target 802 in the initial image from which the gain map was generated (e.g., the phantom targets), as well as a second position 1004 of the mesh object artificial target 802 in the subsequent image. Had there been no change to the focal spot position, the mesh object artificial target 802 would not be visible in the normalized subsequent image resulting in a blank, uniform image for reasons further detailed with reference to FIGS. 4A and 4B.

The image processing system may identify a shift of the mesh object artificial target 802 from the first position 1002 to the second position 1004 along a direction substantially parallel to the y-axis of the detector (e.g., along the y-axis). The shift corresponds to a change in the position of the focal spot along the y-axis from the capture of the initial image to the capture of the subsequent image. In some examples, the shift may be identified on a per-strand basis. For example, a shift may be identified for each strand of the second set of strands in the mesh object artificial target 802 that are positioned substantially parallel to the x-axis of the detector.

To identify the shift, the profile plot 1010 may be generated along a line 1006 intersecting each strand of the second set of strands in respective regions 1008A, 1008B, 1008C, 1008D, 1008E, 1008F, 1008G, and 1008H, collectively regions 1008, of the image 1000. As illustrated, a direction of the line 1006 may be along the y-axis.

The profile plot 1010 may include pixel intensity values for a predefined range of pixels in each of the regions 1008 along the direction of the line 1006. For example, the x-axis 1012 of the profile plot 1010 may include the predefined range of pixels along the y-axis, and the y-axis 1014 of the profile plot 1010 may include pixel intensity values corresponding to each pixel within the predefined range of pixels. Within the predefined range of pixels for each of the regions 1008, a first pixel 1016 having a local maximum pixel intensity value and a second pixel 1018 having a local minimum pixel intensity value may be identified. For example, first pixels 1016A, 1016B, 1016C, 1016D, 1016E, 1016F, 1016G, and 1016H may correspond to a local maximum pixel intensity value for the respective regions 1008A, 1008B, 1008C, 1008D, 1008E, 1008F, 1008G, and 1008H. Second pixels 1018A, 1018B, 1018C, 1018D, 1018E, 1018F, 1018G, and 1018H may correspond to a local minimum pixel intensity value for the respective regions 1008A, 1008B, 1008C, 1008D, 1008E, 1008F, 1008G, and 1008H.

As previously discussed with reference to FIGS. 5 and 6, local maxima and local minima may be identified through parsing methods or data analytics algorithms. Additionally, in some examples, identifying pixels having local maximum and minimum intensity values may further include determining a median pixel intensity value 1020 for the predefined range of pixels, where the pixels having local maximum and minimum intensity values are greater than or less than the median pixel intensity value 1020, respectively, by at least a threshold value.

A pixel distance between the first pixel 1016 and the second pixel 1018 may be determined for each of the regions 1008. The pixel distance may represent the shift (in pixels) of the particular strand of the mesh object artificial target 802 corresponding to the region 1008 from the capture of the initial image to the capture of the subsequent image. As described next, the value or rate of the shifts identified for the respective strands (e.g., a pixel distance between the first pixel 1016 and the second pixel 1018 for each of the regions 1008) are different based on the y-axis coordinate position of the strands relative to an apex of the focal spot.

Referring concurrently to FIGS. 9A-9B and 10A-10B, as the plurality of x-rays are projected within the x-ray beam from the focal spot to the detector, at least a portion of the x-rays (e.g., focal spot central rays) follow a substantially linear projection path from an apex of the focal spot to the detector. This path is illustrated by element 930 in FIGS. 9A-9B and element 1030 in FIGS. 10A-10B. When performing x-ray imaging of a patient's breast, this substantially linear path is adjacent to a chest wall of the patient whose breast is positioned in a breast imaging system, such as the breast imaging system 100. Remaining portions of the x-rays follow progressively angled projection paths from the focal spot to the detector as the projection paths increase in distance from the substantially linear projection path along the x- and y-axes. The progressively angled projection paths cause the intensity of the x-rays to drop as they are projected further away from the apex of the focal spot. As a result, a value or rate of the shifts identified for the respective strands of the mesh object artificial target 802 may be different based on the position of the strands along the x- and y-axes relative to the apex of the focal spot (e.g., relative to elements 930, 1030 representing the projection path of the focal spot central rays from the apex of the focal spot).

For example, for the first set of strands arranged substantially parallel to the y-axis of the detector described with respect to FIGS. 9A-9B, the strands positioned on the right hand side of the image 900 that are closest to the apex of the focal spot may experience larger shifts than the strands positioned toward the middle and left hand side of the image 900. For example, values of the shifts may decrease for strands that are positioned increasingly further away from the apex of the focal (e.g., shift values decrease from regions 908F to 908A). Thus, the maximum shift may be associated with an x-axis pixel coordinate within the substantially linear projection path of the focal spot central rays 930. The maximum shift identified may be determined as the central focal spot shift along the x-axis, which represents an actual change in position of the focal spot (in pixels) along the x-axis.

Table 1 includes example values for relative focal spot shift across the x-axis of the image 900, where each x-axis pixel coordinate corresponds to one of the regions 908A, 908B, 908C, 908D, 908E, and 908F. The maximum shift may be 33.58 pixels at x-axis pixel coordinate 2849 corresponding to region 908F in image 900, the region within the substantially linear projection path of the focal spot central rays 930.

TABLE 1

Relative Focal Spot Shift Values along x-axis

| Region | X-axis Pixel Coordinate | Relative Focal Spot Shift (in pixels) |
|---|---|---|
| 908A | 288 | 9.4 |
| 908B | 1095 | 17.77 |
| 908C | 1894 | 22.4 |
| 908D | 2466 | 27.9 |
| 908E | 2666 | 32.53 |
| 908F | 2849 | 33.58 |

For the second set of strands arranged substantially parallel to the x-axis of the detector described with respect to FIGS. 10A-10B, the strands positioned in the middle of the image 1000 that are closest to the apex of the focal spot may experience larger shifts than those strands positioned further away in the top and the bottom of the image 1000. For example, values of the shifts may decrease for strands that are positioned increasingly further away from the apex of the focal spot (e.g., shift values decrease from regions 1008E to 1008A and from regions 1008E to 1008H). Thus, the maximum shift may be associated with a y-axis pixel coordinate within the substantially linear projection path of the focal spot central rays 1030. The maximum shift identified may be determined as the central focal spot shift along the y-axis, which represents an actual change in position of the focal spot (in pixels) along the y-axis.

Table 2 includes example pixel values for relative focal spot shift across the y-axis of the image 1000, where each y-axis pixel coordinate corresponds to one of the regions 1008A, 1008B, 1008C, 1008D, 1008E, 1008F, 1008G and 1008H. The maximum shift may be 20.6 pixels at y-axis pixel coordinate 1421 corresponding to region 1008E in image 1000, the region within the substantially linear projection path of the focal spot central rays 1030.

TABLE 2

Relative Focal Spot Shift Values along y-axis

| Region | Y-axis Pixel Coordinate | Relative Focal Spot Shift (in pixels) |
| --- | --- | --- |
| 1008A | 98 | 9.3 |
| 1008B | 487 | 10.2 |
| 1008C | 854 | 14 |
| 1008D | 1233 | 16.8 |
| 1008E | 1421 | 20.6 |
| 1008F | 1706 | 18.6 |
| 1008G | 2107 | 18.6 |
| 1008H | 2497 | 17.7 |

As discussed above, the central focal spot shift along the x- and y-axes represents the actual change of position in the focal spot along the x- and y-axes. However, in a clinical setting, targets such as the mesh object artificial target 802 and/or any other target positioned within the substantially linear projection path of the focal spot central rays 930, 1030 cannot be used while imaging the breast because the targets will obstruct a view of the breast. Instead, artificial targets, such as the artificial targets 302, 304 are positioned at a back of the field of view (e.g., furthest away from the chest wall) so that the artificial targets 302, 304 do not overlap with any portion of the imaged breast. For example, the second artificial target 304 may be positioned near x-axis pixel coordinate 288 corresponding to region 908A, and the first artificial target 302 may be positioned near y-axis pixel coordinate 98 corresponding to region 1008A. Accordingly, when identifying the shift of the artificial targets 302, 304 in captured images of the breast, the position of the artificial targets 302, 304 must be taken into account as the shift identified will be less than the actual change of position in the focal spot due to the highly angled projection path of the x-rays at the back of the field of view relative to the substantially linear projection path of the focal spot central rays 930, 1030 near the chest wall.

Therefore, the system 800 having the mesh object artificial target 802 may be implemented prior to imaging the patient's breast for calibration purposes. For example, prior to positioning and imaging the breast, images, such as images 900, 1000, may be captured that include the mesh object artificial target 802. From these images 900, 1000, shifts across the x- and y-axes are identified, and values such as those shown in Table 1 and Table 2 are obtained.

To account for the position of the artificial targets in subsequent images, a ratio of the central focal spot shift to the relative spot shift at the back of the field of view where the artificial targets 302, 304 are to be positioned when imaging the patient's breast can be determined. This ratio is also referred to herein as the central focal spot to target ratio. The central focal spot to target ratio can then be applied to the shift of the artificial targets 302, 304 identified in subsequent captured images of the breast. For example, referring back to Table 1, if the relative spot shift at the central focal spot is 33.58 pixels and the relative spot shift at the x-axis pixel coordinate 288 where the second artificial target 304 is to be positioned in subsequent images is 9.4 pixels, then the central focal spot to target ratio is 33.58:9.4, which is approximately 3.57. Similarly, referring back to Table 2, if the relative spot shift at the central focal spot is 20.6 pixels and the relative spot shift at the y-axis pixel coordinate 98 where the first artificial target 302 is to be positioned in subsequent images is 9.3 pixels, then the central focal spot to target ratio is 20.6:9.3, which is approximately 2.2.

In further examples, similar ratios may be obtained between the relative spot shift at the central focal spot and the relative spot shift at each of the x-axis pixel coordinates and the y-axis pixel coordinates obtained (e.g., for each of coordinates in Table 1 and Table 2). Therefore, when adjusting an image to correct for the shift created by the change in focal spot position, each portion of the image may be adjusted appropriately, as described in greater detail below.

Following calibration, the mesh object artificial target 802 may then be replaced with the artificial targets 302, 304 so as not to obstruct the imaging of the breast. For example, the artificial targets 302, 304 are positioned at a back of the field of view (e.g., furthest away from the chest wall) so that the artificial targets 302, 304 do not overlap with any portion of the imaged breast. The breast may then be positioned in the imaging field and at least a pair of images (e.g., an initial image and a subsequent image) of the breast may be captured with the artificial targets 302, 304 present. Shifts of each of the artificial targets 302, 304 from a first position to a second position between the initial image and subsequent image may be identified as described in detail with reference to FIGS. 5 and 6. The identified shift for the first artificial target 302 may then be multiplied by the central focal spot to target ratio determined during the calibration (e.g., by approximately 2.2) to reflect the actual change in focal spot position along the y-axis. Similarly, the identified shift for the second artificial target 304 may then be multiplied by the central focal spot to target ratio determined during the calibration (e.g., by approximately 3.57) to reflect the actual change in focal spot position along the x-axis. The subsequent image of the breast may then be adjusted based on the identified change in focal spot position along the x- and y-axes and/or the change in the position of the focal spot may be physically reversed (e.g., using electrodes or magnets positioned relative the x-ray tube) for subsequent imaging.

In some examples, when adjusting the subsequent image of the breast, each region of the image may be adjusted independently to account for the differences in shift across the image. For example, using the ratios obtained between the relative spot shift at the central focal spot and the relative spot shift at each of the x-axis pixel coordinates and the y-axis pixel coordinates obtained (e.g., for each of coordinates in Table 1 and Table 2), appropriate shift values for each region of the image can be calculated. The pixels of the image in each region may then be shifted according to a same magnitude as the calculated shift value for the region but in an opposite direction. To provide an example, if in the pair of images of the breast, the identified shift of the second artificial target 304 along the x-axis is 10 pixels and the second artificial target was placed at x-axis coordinate 288, then using the central focal spot to target ratio obtained from Table 1, it can be determined that the maximum shift at x-axis coordinate 2849 was 35.7 pixels (e.g., ratio of 3.57 multiplied by the shift of 10 pixels). The shift can then be identified at each of the other x-coordinates corresponding to the respective regions of the image based on ratios obtained. For example, for x-axis coordinate 1095, the ratio of the relative shift of central focal spot to the relative shift of at the x-axis coordinate 1095 is 1.89 (e.g., 33.58:17.77). Therefore, when it is determined that the maximum shift at x-coordinate 2849 is 35.7 pixels, the shift for the region in the image corresponding to the x-coordinate 1095 is 18.8 (e.g., 35.7/1.89).

When the position of the focal spot is physically reversed for subsequent imaging, the maximum shift along the x- and y-axes representing the actual change in position of the focal spot may be the pixel distance values converted to the focal spot shift vectors. Therefore, the pixel distance shift identified for the first artificial target 302 along the y-axis and the pixel distance shift identified for the second artificial target 304 along the x-axis are multiplied by the respective central focal spot to target ratios to obtain the maximum shift along the x- and y-axes. Using a similar method described above with reference to FIG. 7, the pixel distances associated with the maximum shift may be converted to focal spot shift vectors representing the change in the position of the focal spot along the x- and y-axes. A control signal may then be generated based on the focal spot shift vectors for transmission to an apparatus of the system that is capable of controlling dimensions of an electron beam received at the anode of the x-ray tube. For example, dimensions of the electron beam may affect the position of the focal spot on the anode, and thus the control signal may cause the apparatus to adjust the dimensions of the electron beam to reverse the change in the position of the focal spot along the x- and y-axes for subsequent imaging.

Figure 11:
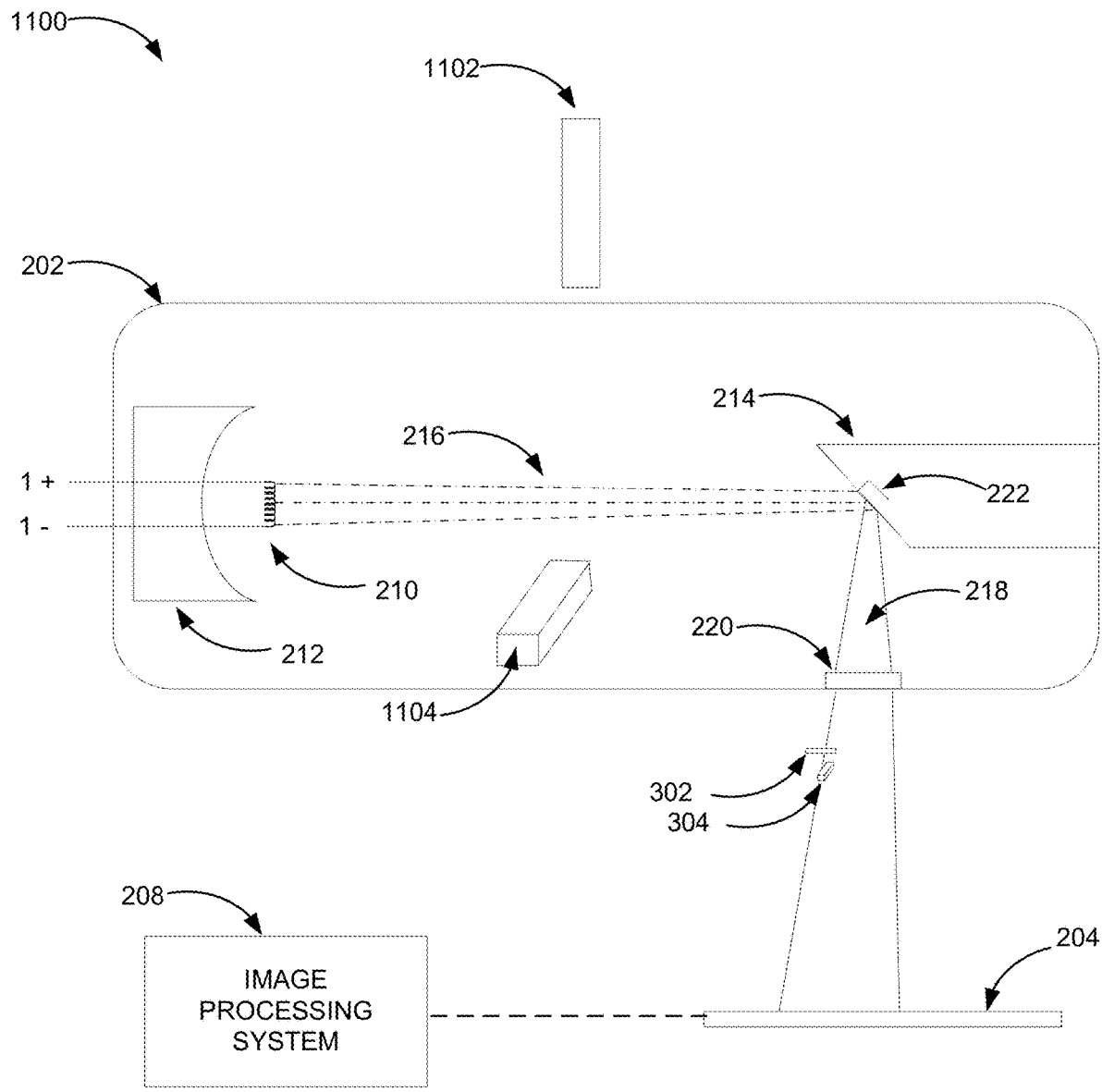
FIG. 11 is an example system having an apparatus comprised of magnets that is capable of controlling dimensions of an electron beam.

FIG. 11 is an example system 1100 having an apparatus comprised of magnets 1102, 1104 that is capable of controlling dimensions of an electron beam 216. The system 1100 is similar to the system 200 shown and described with reference to FIG. 2, with the exception that the system 1100 includes the apparatus comprised of magnets 1102, 1104, and at least a first artificial target 302 and a second artificial target 304 as shown and described with reference to FIG. 3. In other examples, the system 1100 may include only one artificial target, such as the artificial target 206, as shown and described with reference to FIG. 2. In further examples, the system 1100 may include a mesh object artificial target, similar to the mesh object artificial target 802 shown and described with reference to FIG. 8.

In some examples, the apparatus may be a component housed within the x-ray tube 202. In other examples, and as illustrated in FIG. 11, the apparatus may be arranged exterior to the x-ray tube 202. The apparatus can include at least two magnets: a first magnet 1102 and a second magnet 1104. The magnets 1102, 1104 may be electromagnets that are capable of being controlled electronically. For example, providing a signal to the magnets 1102, 1104 may vary the strength of the magnetic field of the magnets 1102, 1104. The first magnet 1102 may be configured to deflect the electron beam 216 in one direction. The second magnet 1104 may be configured to deflect the electron beam 216 in an opposite direction.

Each time a new electron beam 216 impacts the anode 214 (e.g., each time a new image is to be captured), a position of the focal spot 222 of the anode 214 can change. A projection path for an x-ray beam formed by the x-rays emitted from the anode 214 may correspondingly change causing any objects, such as the first artificial target 302 and the second artificial target 304, in the respective projection path to be different (e.g., spatially shifted) among the image captures. Resultantly, a position of the first artificial target 302 and the second artificial target 304 in an initial image can be different than a position of the first artificial target 302 and the second artificial target 304 in a subsequent image even though the first artificial target 302 and the second artificial target 304 are stationary targets. The image processing system 208 can identify a shift of the first artificial target 302 and the second artificial target 304 from a first position in the initial image to a second position in the subsequent image, where the shift corresponds to a change in the position of the focal spot 222. As one example, the first artificial target 302 may be arranged substantially parallel to the x-axis of the detector 204, and the second artificial target 304 may be arranged substantially parallel to the y-axis of the detector 204. Therefore, the image processing system 208 may identify the shift along both x- and y-axes and thus, the change in the position of the focal spot 222 along the x- and y-axes.

As shown and described with reference to FIG. 5 and FIG. 6, the shift of the first artificial target 302 and the second artificial target 304 from the first position in the initial image to the second position in the subsequent image may be identified in one or more directions (e.g., along x- and y-axes) by generating profile plots. As shown and described with reference to FIG. 7, pixel distances representing the identified shift of the artificial targets 302, 304 along the x- and/or y-axes may be converted to first and second focal spot shift vectors, respectively. A resultant focal spot shift vector and a first angle associated with the resultant focal spot shift vector may then be determined based on the first and second focal spot shift vectors.

A control signal may then be generated based on the first angle associated with the resultant focal spot shift vector that may cause the apparatus of the system 1100 to adjust the dimensions of the electron beam 216. For example, the control signal may identify a second angle that is congruent to the first angle associated with the resultant focal spot shift vector (e.g., has a same measure in degrees or magnitude) but is in an opposite direction to enable reversal of the change of the position of the focal spot 222. The control signal may cause the apparatus of the system 1100 to adjust the dimensions of the electron beam 216 by the magnitude and direction of the second angle to reverse the change in the position of the focal spot 222 for subsequent (e.g., future) imaging. For example, based on the direction of the second angle, the control signal may cause the first magnet 1102 to deflect the electron beam 216 in the one direction based on a strength of the first magnet 1102 as a function of the identified shift. Additionally or alternatively, based on the direction of the second angle, the control signal may cause the second magnet 1104 to deflect the electron beam 216 in the opposite direction based on a strength of the second magnet 1104 as a function of the identified shift.

In some examples, at least one of the first magnet 1102 and the second magnet 1104 may be positioned parallel to the first focal spot shift vector, while the other of the first magnet 1102 and the second magnet 1104 may be positioned parallel to the second focal spot shift vector. Thus, the first magnet 1102 and the second magnet 1104 may be positioned 90 degrees from another, and may work individually or in conjunction with one another based on the direction of the second angle to deflect the electron beam 216 along the x- and/or y-axes. In other examples, the first magnet 1102 and the second magnet 1104 may be arranged in a different manner (e.g., diagonally). Additionally, while two magnets are shown and described herein to enable deflection of the electron beam 216 in two directions (e.g., along the x- and y-axes) in other examples, the apparatus may include a single magnet that is able to deflect electron beam 216 in one direction.

Figure 12:
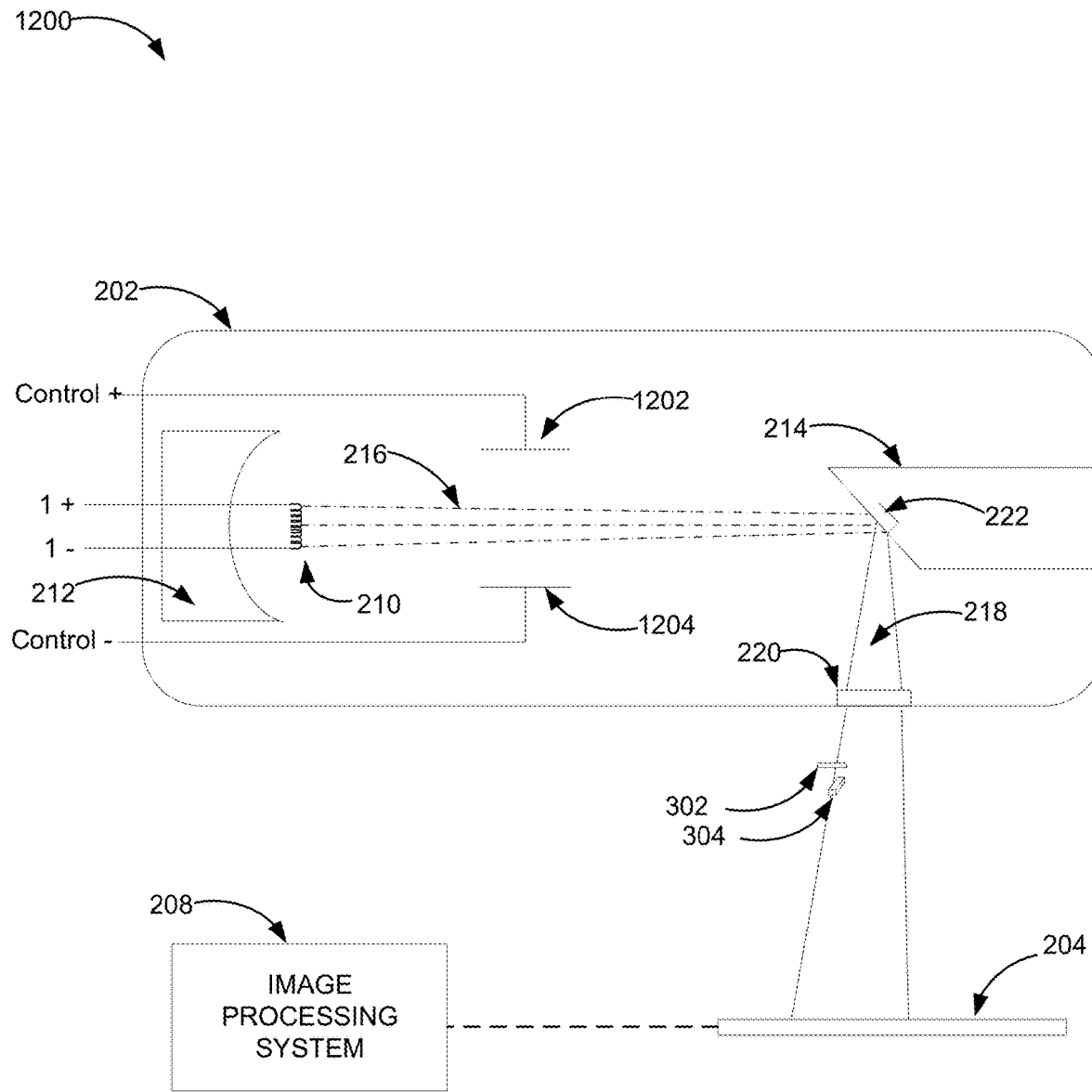
FIG. 12 is another example system having an apparatus comprised of electrodes that is capable of controlling dimensions of an electron beam.

FIG. 12 is another example system 1200 having an apparatus comprised of electrodes that is capable of controlling dimensions of an electron beam. The system 1200 is similar to the system 200 shown and described with reference to FIG. 2, with the exception that the system 1200 includes the apparatus comprised of electrodes, and at least a first artificial target 302 and a second artificial target 304 as shown and described with reference to FIG. 3. In other examples, the system 1200 may include only one artificial target, such as the artificial target 206, as shown and described with reference to FIG. 2. In further examples, the system 1200 may include a mesh object artificial target, similar to the mesh object artificial target 802 shown and described with reference to FIG. 8.

In some examples, the apparatus may be a component housed within the x-ray tube 202, as illustrated. In other examples, the apparatus may be arranged exterior to the x-ray tube 202. The apparatus can include a set of electrodes: a first electrode 1202 and a second electrode 1204. A control signal may be applied across wires or terminals connected to the electrodes 1202, 1204 as depicted by the Control+ and Control− in FIG. 11. The first electrode 1202 may be positioned opposite a path of the electron beam 216 from the second electrode 1204.

When the control signal is applied across the first electrode 1202 and the second electrode 1204, an electric field is generated between them. The electric field interacts with the electrons in the electron beam 216 due to the negative charge of the electrons in the electron beam 216. Depending on the control signal, the electrons in the electron beam 216 may either be drawn towards the first electrode 1202 (e.g., electrons may be deflected in one direction) or drawn towards the second electrode 1204 (e.g., electrons may be deflected in an opposite direction). By manipulating the control signal applied across the first electrode 1202 and the second electrode 1204, the position that the electron beam 216 impacts the anode 214 may be altered. Thus, the position of the focal spot 222 may be altered.

Each time a new electron beam 216 impacts the anode 214 (e.g., each time a new image is to be captured), a position of the focal spot 222 of the anode 214 can change. A projection path for an x-ray beam formed by the x-rays emitted from the anode 214 may correspondingly change causing any objects, such as the first artificial target 302 and the second artificial target 304, in the respective projection path to be different (e.g., spatially shifted) among the image captures. Resultantly, a position of the first artificial target 302 and the second artificial target 304 in an initial image may be different than a position of the first artificial target 302 and the second artificial target 304 in a subsequent image. The image processing system 208 may identify a shift of the first artificial target 302 and the second artificial target 304 from a first position in the initial image to a second position in the subsequent image, where the shift corresponds to a change in the position of the focal spot 222. As one example, the first artificial target 302 may be arranged substantially parallel to the x-axis of the detector 204, and the second artificial target 304 may be arranged substantially parallel to the y-axis of the detector 204. Therefore, the image processing system 208 may identify the shift along both x- and y-axes and thus, the change in the position of the focal spot 222 along the x- and y-axes.

As shown and described with reference to FIG. 5 and FIG. 6, the shift of the first artificial target 302 and the second artificial target 304 from the first position in the initial image to the second position in the subsequent image may be identified in one or more directions (e.g., along x- and y-axes) by generating profile plots. As shown and described with reference to FIG. 7, pixel distances representing the identified shift of the artificial targets 302, 304 along the x- and/or y-axes may be converted to first and second focal spot shift vectors, respectively. A resultant focal spot shift vector and a first angle associated with the resultant focal spot shift vector may then be determined based on the first and second focal spot shift vectors.

To reverse the change in position of the focal spot 222, the control signal applied across the wires or terminals connected to the electrodes 1202, 1204 may be generated based on the first angle associated with the resultant focal spot shift vector. For example, a second angle that is congruent to the first angle associated with the resultant focal spot shift vector (e.g., has a same measure in degrees or magnitude) but is in an opposite direction may be identified to enable reversal of the change of the position of the focal spot 222 for subsequent (e.g., future) imaging. The control signal may cause the dimensions of the electron beam 216 to adjust by the magnitude and direction of the second angle. For example, based on the direction of the second angle, the control signal may cause the electrons in the electron beam 216 to be drawn towards the first electrode 1202 (e.g., electrons may be deflected in one direction). The electrons may be deflected in the one direction based on the strength of the electrical field generated by the electrodes 1202, 1204 as a function of the identified shift. Additionally or alternatively, based on the direction of the second angle, the control signal may cause the electrons in the electron beam 216 to be drawn towards the second electrode 1204 (e.g., electrons may be deflected in an opposite direction). The electrons may be deflected in the opposite direction based on the strength of the electrical field generated by the electrodes 1202, 1204 as a function of the identified shift.

In some examples, the first electrode 1202 and the second electrode 1204 may only enable movement of the electron beam 216 in a first direction (e.g., only up and down along the y-axis or right and left along the x-axis). Therefore, the apparatus may include additional pairs of electrodes, described in greater detail with reference to FIG. 13 below, to allow for additional control of the electron beam 216 such that the electron beam 216 may be moved in a second direction, as well as the first (e.g., the electron beam 216 may move both up and down along the y-axis and right and left along the x-axis).

Figure 13:
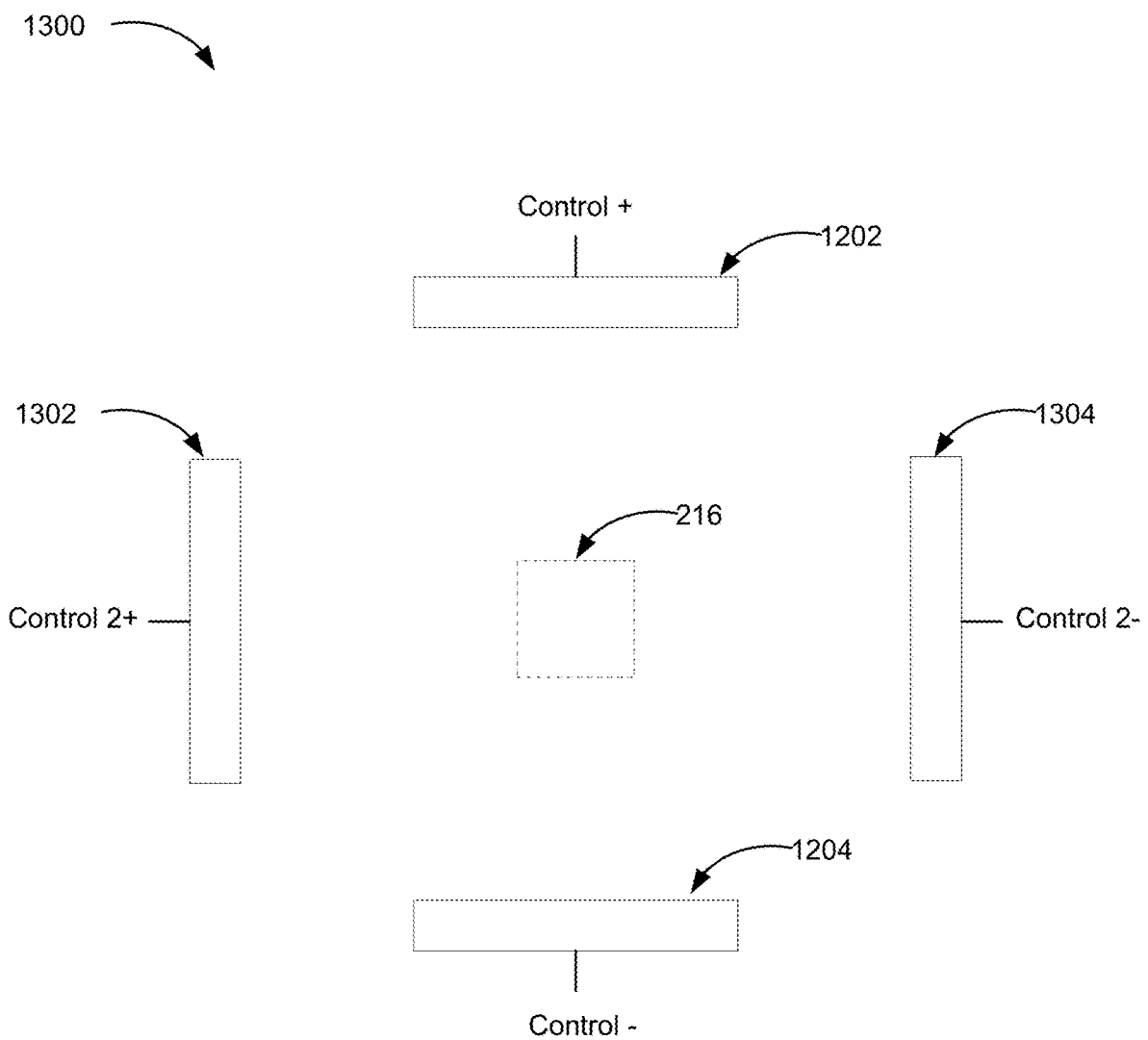
FIG. 13 is an example arrangement of electrodes.

FIG. 13 is an example arrangement 1300 of electrodes. While only two electrodes (e.g., the first electrode 1202 and the second electrode 1204) were depicted in the apparatus shown and described with reference to FIG. 12, additional electrodes, such as a third electrode 1302 and a fourth electrode 1304, may also be included to manipulate or control the electron beam 216. The first electrode 1202 and the second electrode 1204 may form a first pair of electrodes 1202, 1204, while the third electrode 1302 and the fourth electrode 1304 may form a second pair of electrodes 1302, 1304. The view depicted in FIG. 13 is an orthogonal view from the schematic view depicted in FIG. 12. Accordingly, the electron beam 216 may be viewed as coming out of the page.

Within the second pair of electrodes 1302, 1304, the third electrode 1302 may be positioned opposite a path of the electron beam 216 from the fourth electrode 1304. The second pair of electrodes 1302, 1304 may be positioned such that they are orthogonal to the first pair of electrodes 1202,

1204. The second pair of electrodes 1302, 1304 allow for additional control of the electron beam 216 such that the electron beam 216 may be moved in a second direction. In the example depicted, the first pair of electrodes 1202, 1204 may be used to move the electron beam 216 in a first direction (e.g., along the y-axis) and the second pair of electrodes 1302, 1304 may be used to move the electron beam in a second direction (e.g., along the x-axis). Additional pairs of electrodes may also be added to move the electron beam 216 in different or additional directions as well.

The second pair of electrodes 1302, 1304 may be controlled by a second control signal. For instance, a terminal of the third electrode 1302 and the terminal of the fourth electrode 1304 may be connected to the control signal source as indicated by the Control2+ and Control2− designations in FIG. 13. The second control signal may be generated and determined in substantially the same manner as the first control signal used to control the first pair of electrodes 1202, 1204 described above with reference to FIG. 12. The first control signal, however, may be different from the second control signal and have different characteristics.

Figure 14A:
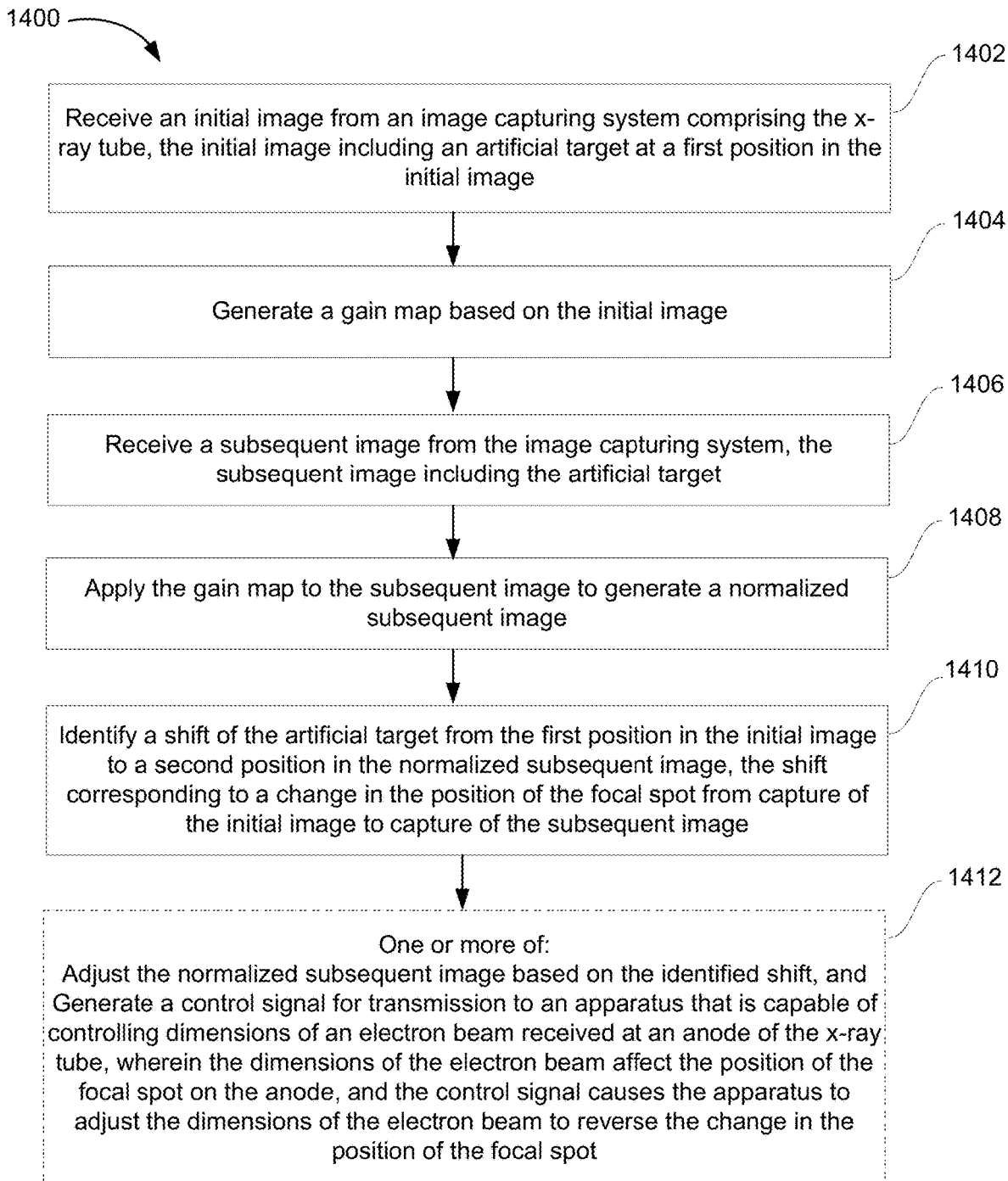
FIG. 14A depicts an example method for tracking a position of a focal spot.

FIG. 14A illustrates an example method 1400 for tracking a position of a focal spot of an x-ray tube, such as the focal spot 222 of the x-ray tube 202 shown and described with reference to FIG. 2. In some examples, the method 1400 may be performed by an image processing system, such as image processing system 208 shown and described with reference to FIG. 2.

The method 1400 may begin at operation 1402, where an initial image may be received from an image capturing system that includes the x-ray tube. The initial image may include an artificial target at a first position in the initial image. At operation 1404, a gain map may be generated based on the initial image.

At operation 1406, a subsequent image may be received from the image capturing system. The subsequent image may also include the artificial target. At operation 1408, the gain map generated at operation 1404 may be applied to the subsequent image to generate a normalized subsequent image. The application of the gain map to the subsequent image may reveal that a position of the artificial target has changed from the first position in the initial image.

At operation 1410, a shift of the artificial target from the first position in the initial image to a second position in the normalized subsequent image may be identified, where the shift corresponds to a change in the position of the focal spot from the capture of the initial image to the capture of the subsequent image. Identification of the shift of the artificial target, and thus identification of the change in the position of the focal spot, is described with reference to FIG. 14B.

At optional operation 1412, the normalized subsequent image may be adjusted based on the identified shift to correct for the shift in the normalized subsequent image. Additionally or alternatively, a control signal may be generated for transmission to an apparatus of the system capable of reversing the change in the position of the focal spot for subsequent imaging by adjusting dimensions of an electron beam received at an anode of the x-ray tube that affect the position of the focal spot on the anode.

To provide an example clinical scenario in which the method 1400 may be implemented, an imaging system, such as the breast imaging system 100 in FIG. 1, may be used to capture images of a patient's breast. Prior to positioning and imaging the breast, an initial image may be captured that includes the artificial target. The artificial target may then be removed such that the artificial target is no longer within the projection path of the x-ray beam. The breast may then be positioned in the imaging field and an image of the breast may be captured without the artificial target present. The breast may be removed and the artificial target repositioned such that artificial target is again within the projection path of the x-ray beam. A subsequent image that includes the artificial target may then be captured. A change in focal spot position may then be identified using the initial and subsequent images having the artificial target. The captured image of the breast may then be adjusted based on the identified change in focal spot position and/or the change in the position of the focal spot may be physically reversed (e.g., using electrodes or magnets positioned relative the x-ray tube) for subsequent imaging. In other examples, the artificial target may remain present when the image of the breast is captured, as described below with reference to FIG. 15. In such examples, the artificial target may be positioned such that the location of the artificial target in the result image does not overlap with any portion of the imaged breast.

Figure 14B:
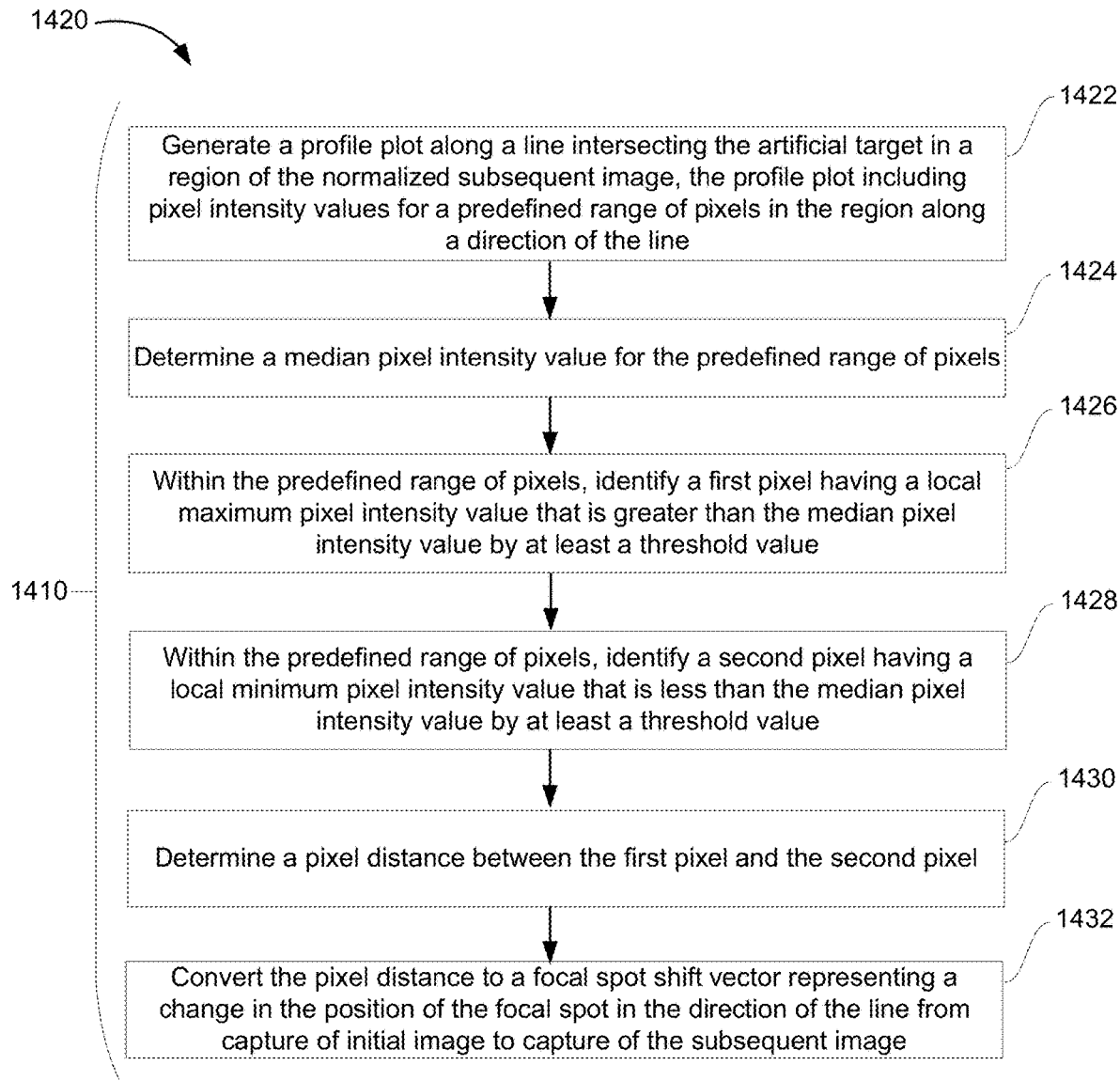
FIG. 14B depicts an example method for identifying a change in focal spot position.

FIG. 14B illustrates an example method 1420 for identifying a change in focal spot position. In some examples, the method 1420 can be used to at least partially perform the operation 1410 described in FIG. 14. The method 1420 may be performed by an image processing system, such as image processing system 208 shown and described with reference to FIG. 2.

At operation 1422, a profile plot may be generated along a line intersecting the artificial target in a region of the normalized subsequent image. The profile plot may include pixel intensity values for a predefined range of pixels in the region along a direction of the line. In some examples, the profile plot may be generated along the x-axis as shown and described with reference to FIG. 5. In other examples, the profile plot may be generated along the y-axis as shown and described with reference to FIG. 6.

At operation 1424, a median pixel intensity value for the predefined range of pixels may be determined. Based on the median pixel intensity value, a first pixel having a local maximum pixel intensity value and a second pixel having a local minimum pixel intensity value may be determined within the predefined range of pixels at operations 1426 and 1428. For example, at operation 1426, a first pixel having a local maximum pixel intensity value that is greater that the median pixel intensity value by at least a threshold value may be identified. At operation 1428, a second pixel having a local minimum pixel intensity value that is less than the median pixel intensity value by at least a threshold value may be identified.

At operation 1430, a pixel distance between the first pixel and the second pixel may be determined. In some examples, the pixel distance may be used to adjust the normalized subsequent image to correct for (e.g., reverse) the shift. In further examples, the pixel distance may be used to adjust the gain map, which may then be reapplied to the normalized subsequent image. For example, the normalized subsequent image or the gain map may be adjusted according to a same magnitude of the pixel distance but in an opposite direction to correct for the shift.

At operation 1432, the pixel distance may be converted to a focal spot shift vector that represents a change in the position of the focal spot in the direction of the line from the capture of the initial image to the capture of the subsequent image. In some examples, a control signal may be generated based on the focal spot shift vector for transmission to an apparatus that is capable of controlling dimensions of an electron beam received at an anode of the x-ray tube, such as the apparatus shown and described with reference to FIG. 11 or the apparatus shown and described with reference to FIGS. 12 and 13. The dimensions of the electron beam affect the position of the focal spot on the anode, and therefore, the control signal may cause the apparatus to adjust the dimensions of the electron beam to reverse the change in the position of the focal spot in the direction of the line.

Figure 15:
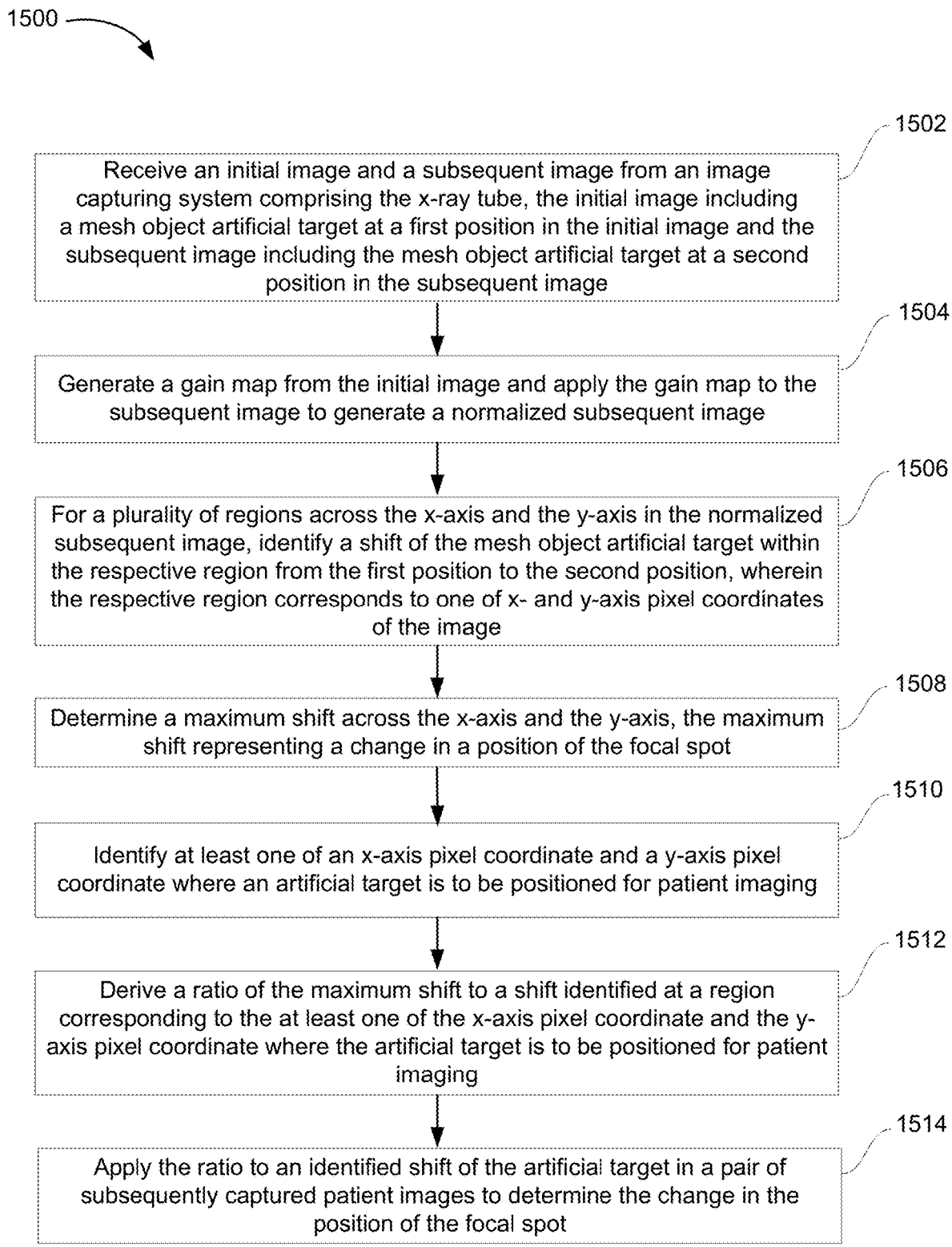
FIG. 15 illustrates an example calibration method.

FIG. 15 illustrates an example calibration method 1500. The example calibration method 1500 may be performed in conjunction with and/or prior to other described methods, such as the methods 1400, 1420 described with reference to FIGS. 14A and 14B. In some examples, the calibration method 1500 may be performed by an image processing system, such as image processing system 208 shown and described with reference to FIG. 2.

For the calibration (e.g., prior to patient imaging), a mesh object artificial target, similar to the mesh object artificial target 802 described with reference to FIG. 8, may be arranged relative to an image capturing system that comprises an x-ray tube and a detector. The mesh object artificial target may be comprised of a first set of strands substantially parallel to the y-axis of the detector and a second set of strands that intersect with the first set of strands and are substantially parallel to the x-axis of the detector. At operation 1502, a pair of images comprising an initial image and subsequent image may be received from the image capturing system. The initial image may include the mesh object artificial target at a first position. The subsequent image may include mesh object artificial target at a second position.

At operation 1504, a gain map may be generated from the initial image and applied to the subject image to generate a normalized subsequent image. The normalized subsequent image may include a plurality of regions across the x-axis and the y-axis. Each region across the x-axis may represent a strand from the first set of strands at a particular x-coordinate (e.g., regions 908 in FIGS. 9A-9B), and each region across the y-axis may represent a strand from the second set of strands at a particular y-axis coordinate (e.g., regions 1008 in FIGS. 10A-10B).

At operation 1506, a shift of the mesh object artificial target from the first position to the second position may be identified within each region of the plurality of regions. The shift for each region may be identified using similar operations described with reference to the method 1420 in FIG. 14B. The shifts may be different across the image, due to an angle of the projection path of the x-rays from the focal spot to the detector. For example, a portion of the x-rays may follow a linear projection path from the apex of the focal spot to the detector, while remaining x-rays may follow progressively angled projection paths from the focal spot to the detector as the projection paths increase in distance from the substantially linear projection path along the x- and y-axes. This causes the intensity of the x-ray beam to drop as it projects further away from the apex of the focal spot. Resultantly, progressively smaller shifts are identified among the regions that are further away from the apex of the focal spot.

From among the shifts identified at operation 1506, a maximum shift across the x-axis and a maximum shift across the y-axis may be determined at operation 1508. The maximum shift across the x- and y-axes may occur at respective x- and y-axis coordinates of regions located within the linear projection path from the apex of the focal spot to the detector. The maximum shift across the x- and y-axes may represent an actual change in position of the focal spot.

At operation 1510, an x-axis pixel coordinate and/or a y-axis coordinate at which an artificial target is to be positioned for patient imaging is identified. As previously discussed, targets such as the mesh object artificial target and/or any other target positioned within the substantially linear projection path from the apex of the focal spot (e.g., near the chest wall) cannot be used while imaging a patient's breast because the targets will obstruct a view of the breast. Instead, an artificial target is positioned at a back of the field of view (e.g., furthest away from the chest wall) so that the artificial target does not overlap with any portion of the imaged breast. Accordingly, when identifying the shift of the artificial target in captured images of the breast, the position of the artificial target must be taken into account as the shift identified will be less than the actual change of position in the focal spot due to the highly angled projection path of the x-rays at the back of the field of view relative to the substantially linear projection path from the apex of the focal spot near the chest wall.

At operation 1512, a ratio of the maximum shift determined at operation 1508 to a shift identified at the x-axis pixel coordinate and/or y-axis pixel coordinate where the artificial target is to be positioned for patient imaging (e.g., the coordinate(s) identified at operation 1510) is derived. In some examples, similar ratios of the maximum shift to each of the other shifts identified across the regions may also be derived for use in independently adjusting each region of the image to correct for respective shifts.

At operation 1514, the ratio determined at operation 1512 may be applied to a shift of the artificial target identified in a pair of subsequently captured patient images to determine the change in the position of the focal spot. For example, the ratio can be applied to the shift identified at operation 1410 with reference to FIG. 4A, further described as the pixel distance between the first and second pixel determined at operation 1430 with reference to FIG. 4B. The patient images may then be adjusted to correct for the pixel shift caused by the change in position of the focal spot, and/or the position of the focal spot may be physically reversed.

Figure 16:
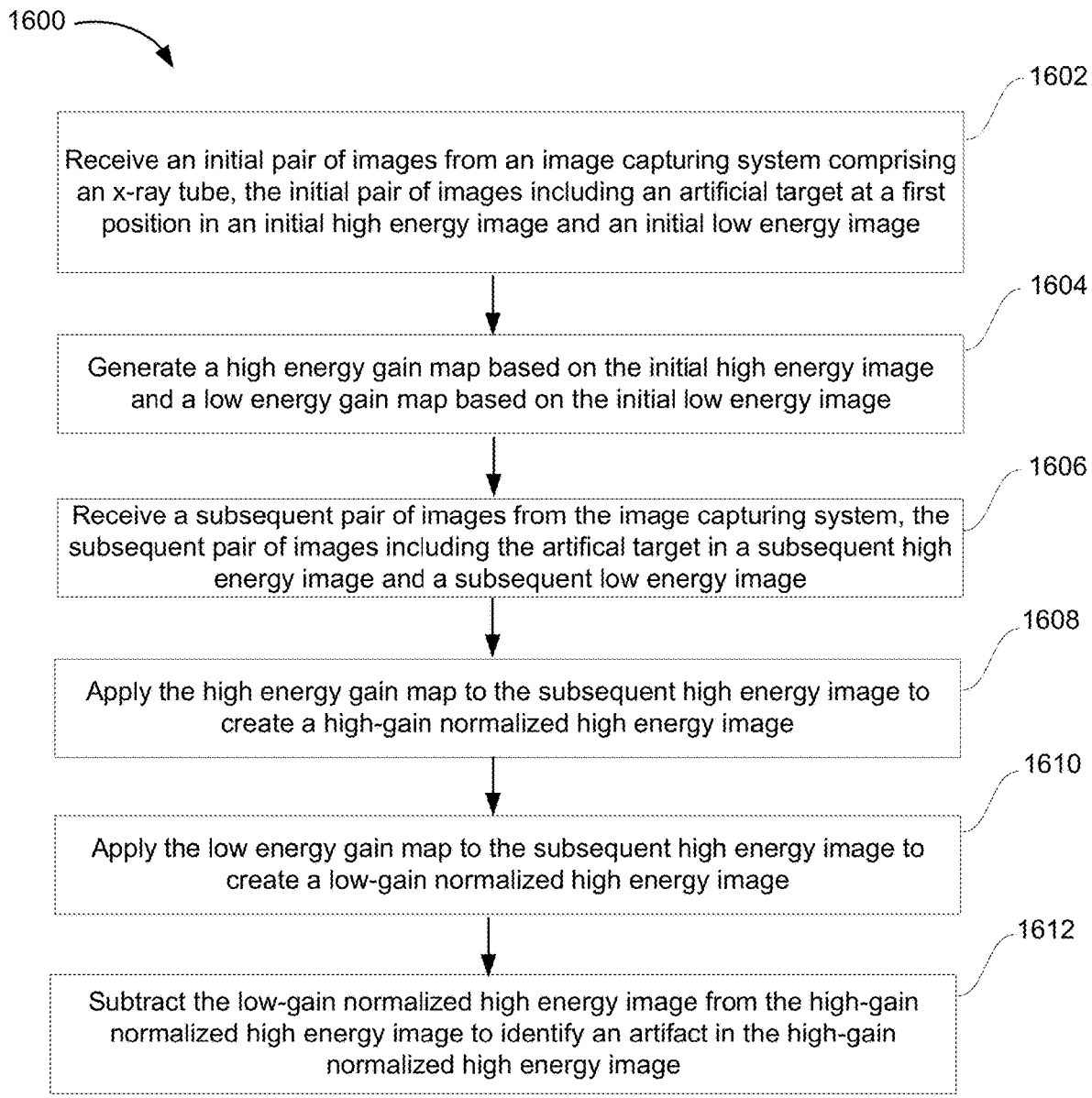
FIG. 16 depicts an example method for identifying an artifact.

FIG. 16 illustrates an example method 1600 for identifying an artifact. The method 1600 may be performed by an image processing system, such as image processing system 208 of system 200 shown and described with reference to FIG. 2. In some examples, the method 1600 may be performed when contrast-enhanced digital mammography (CEDM) is implemented by the system for x-ray imaging.

For CEDM, a contrast medium may be administered intravenously to a patient (e.g., via an antecubital vein). Two images may be captured sequentially. One image may be a high energy image, while the other image may be a low energy image. The high energy image may be obtained by applying a first type of x-ray filter (e.g., a copper (Cu) filter). The low energy image may be obtained by applying a second type of x-ray filter (e.g., a rhodium (Rh) filter or a silver (Ag) filter). The electronic gains for the high energy image and the low energy image charge integration may be the same. Additionally, the high energy image and the low energy image positions may be substantially the same (e.g. at a fixed angle). The high energy image and the low energy image may be digitally subtracted from each other to produce a single image that highlights areas of neovascularity.

One source of artifacts in the single image caused by the change in position of the focal spot from the capture of the initial pair of images to the capture of the subsequent pair of images may be an x-ray filter induced artifact. For example, the change in focal spot position may cause a defect in the x-ray filter (e.g., a wrinkle) as a result of the x-ray beam projecting through a different region of the filter in the subsequent image captures.

The method 1600 may be implemented to identify an artifact within the high energy image. For example, a Cu filter artifact (e.g., a defect or wrinkle in the Cu filter) may be present in the image due the change in focal spot position. The method 1600 may begin at operation 1602, where an initial pair of images may be received from an image capturing system. The initial pair of images may include an initial high energy image and an initial low energy image. The initial high energy image may include an artificial target at a first position. The initial low energy image may include the artificial target at a first position.

At operation 1604, a high energy gain map may be generated based on the initial high energy image, and a low energy gain map may be generated based on the initial low energy image. The high energy gain map and the low energy gain map may be generated in a same or similar manner as described above with reference to FIGS. 4A and 4B. The high energy gain map and the low energy gain map may be stored in memory of the image processing system.

At operation 1606, a subsequent pair of images may be received from the image capturing system. The subsequent pair of images may include a subsequent high energy image and a subsequent low energy image. Both the subsequent high energy image and the subsequent low energy image may include the artificial target.

At operation 1608, the high energy gain map ($G_{heCu}$) may be applied to the subsequent high energy image ($I_{heCu}$) to create a high-gain normalized high energy image ($R_k$), as shown in equation (1) below:

$$R_k = (I_{heCu} * G_{heCu}) \quad (1)$$

The high-gain normalized high energy image may have a Cu filter artifact present in the high energy image.

At operation 1610, the low energy gain map ($G_{leRh}$) may be applied to the subsequent high energy image ($I_{heCu}$) to create a low-gain normalized energy image ($A_k$), as shown in equation (2) below:

$$A_k = (I_{heCu} * G_{leRh}) \quad (2)$$

The low-gain normalized energy image may not include the artifact due to the application of the low energy gain map, which was generated from the initial low energy image during which the Rh filter rather than the Cu filter was applied.

At operation 1612, the low-gain normalized high energy image ($A_k$) may be subtracted from the high-gain normalized high energy image ($R_k$) to identify the artifact ($Q_k$) in the high-gain normalized high energy image as shown in equation (3) below:

$$Q_k = A_k R_k \quad (3)$$

For example, the difference between the high-gain normalized high energy image (e.g., having the artifact) and the low-gain normalized high energy image (e.g., not having the artifact) may be the Cu filter artifact induced by the change in focal spot position. Therefore, incorporating equations (1), (2), and (3), the artifact ($Q_k$) may be identified as shown in equation (4) below:

$$Q_k = (I_{heCu} * G_{leRh}) - (I_{heCu} * G_{heCu}) \quad (4)$$

In some examples, the high-gain normalized high energy image may then be adjusted to remove the artifact. The operations in method 1600 may be performed on a pixel-by-pixel basis to identify pixels that are representative of artifacts.

Figure 17:
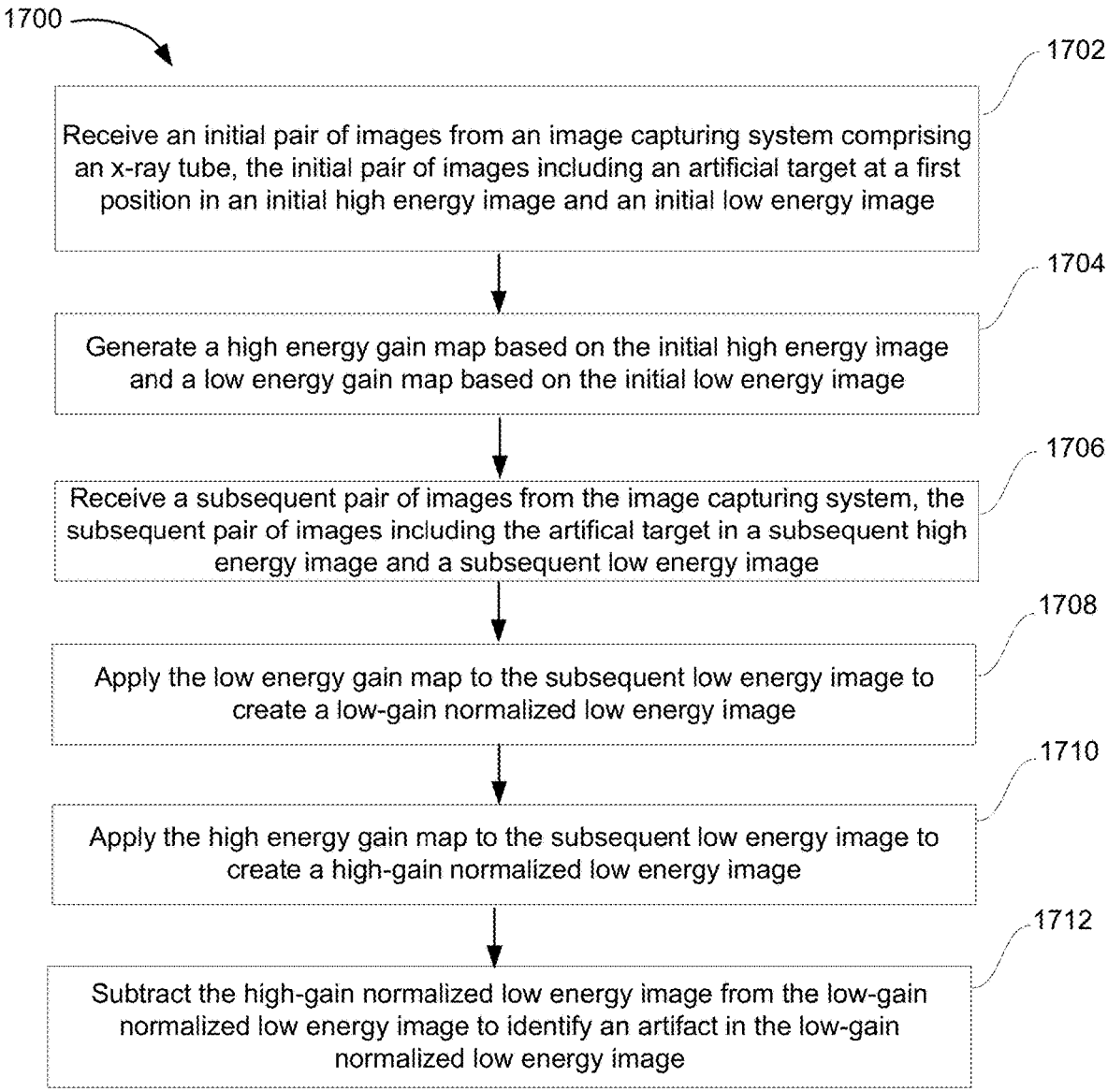
FIG. 17 depicts another example method for identifying an artifact.

FIG. 17 illustrates an example method 1700 for identifying an artifact. The method 1700 may be performed by an image processing system, such as image processing system 208 of system 200 shown and described with reference to FIG. 2. Similar to the method 1600 described above with reference to FIG. 16, in some examples, the method 1700 may be performed when CEDM is implemented by the system for x-ray imaging.

As previously discussed, two images may be captured when CEDM is implemented. One image may be a high energy image, while the other image may be a low energy image. Artifacts may be present in one or both of the high energy image and the low energy image due to the change in focal spot position. For example, as described with reference to FIG. 16, a defect or wrinkle in the Cu filter applied for the capture of the high energy image may be present in the high energy image. Similarly, a defect or wrinkle in the Rh filter applied for the capture of the low energy image may be present in the low energy image.

The method 1700 may be implemented to identify an artifact within the low energy image captured. For example, an Rh filter artifact (e.g., a defect or wrinkle in the Rh filter) may be present in the image due the change in focal spot position. The method 1700 may begin at operation 1702, where an initial pair of images may be received from an image capturing system. The initial pair of images may include an initial high energy image and an initial low energy image. The initial high energy image may include an artificial target at a first position. The initial low energy image may include the artificial target at a first position.

At operation 1704, a high energy gain map may be generated based on the initial high energy image, and a low energy gain map may be generated based on the initial low energy image. The high energy gain map and the low energy gain map may be generated in a same or similar manner as described above with reference to FIGS. 4A and 4B. The high energy gain map and the low energy gain map may be stored in memory of the image processing system.

At operation 1706, a subsequent pair of images may be received from the image capturing system. The subsequent pair of images may include a subsequent high energy image and a subsequent low energy image. Both the subsequent high energy image and the subsequent low energy image may include the artificial target.

At operation 1708, the low energy gain map may be applied to the subsequent low energy image to create a low-gain normalized low energy image. The low-gain normalized low energy image may have an Rh filter artifact present in the low energy image. At operation 1710, the high energy gain map may be applied to the subsequent low energy image to create a high-gain normalized low energy image. The high-gain normalized low energy image may not include the artifact due to the application of the high energy gain map, which was generated from the initial high energy image during which the Cu filter rather than the Rh filter was applied.

At operation 1712, the high-gain normalized low energy image may be subtracted from the low-gain normalized low energy image to identify the artifact in the low-gain normalized low energy image. For example, the difference between the low-gain normalized high energy image (e.g., having the artifact) and the high-gain normalized high energy image (e.g., not having the artifact) may be the Rh filter artifact. In some examples, the low-gain normalized low energy image may then be adjusted to remove the artifact.

In some examples, both method 1600 described with reference to FIG. 16 and method 1700 may be performed such that any filter artifacts (e.g., both Cu and Rh filter artifacts) induced by the change in focal spot position can be identified and removed in the high-gain normalized high energy image and the low-gain normalized low energy image, respectively. The high-gain normalized high energy image and the low-gain normalized low energy image may then be digitally subtracted from each other to produce the single image that highlights areas of neovascularity.

Figure 18:
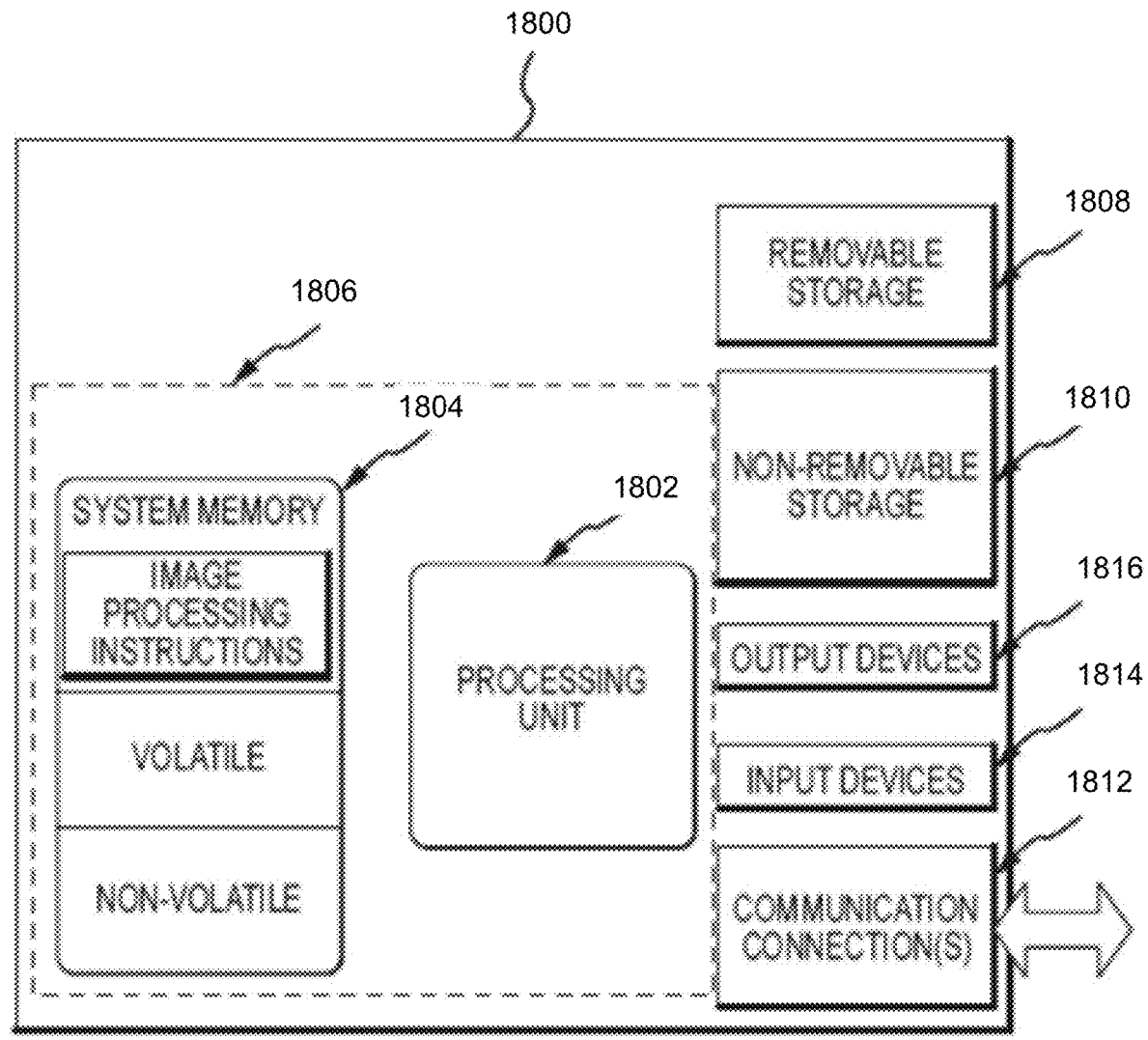
FIG. 18 illustrates one example of a suitable operating environment in which one or more of the present examples can be implemented.

FIG. 18 illustrates one example of a suitable operating environment 1800 in which one or more of the present embodiments can be implemented. This operating environment may be incorporated directly into the imaging systems disclosed herein, or may be incorporated into a computer system discrete from, but used to control, the imaging systems described herein. This is only one example of a suitable operating environment and is not intended to suggest any limitation as to the scope of use or functionality. Other computing systems, environments, and/or configurations that can be suitable for use include, but are not limited to, imaging systems, personal computers, server computers, hand-held or laptop devices, multiprocessor systems, microprocessor-based systems, programmable consumer electronics such as smart phones, network PCs, minicomputers, mainframe computers, tablets, distributed computing environments that include any of the above systems or devices, and the like.

In its most basic configuration, operating environment 1800 typically includes at least one processing unit 1802 and memory 1804. Depending on the exact configuration and type of computing device, memory 1804 (storing, among other things, instructions to perform the image acquisition and processing methods disclosed herein) can be volatile (such as RAM), non-volatile (such as ROM, flash memory, etc.), or some combination of the two. This most basic configuration is illustrated in FIG. 18 by dashed line 1806. Further, environment 1800 can also include storage devices (removable, 1808, and/or non-removable, 1810) including, but not limited to, magnetic or optical disks or tape. Similarly, environment 1800 can also have input device(s) 1814 such as touch screens, keyboard, mouse, pen, voice input, etc., and/or output device(s) 1816 such as a display, speakers, printer, etc. Also included in the environment can be one or more communication connections 1812, such as LAN, WAN, point to point, Bluetooth, RF, etc.

Operating environment 1800 typically includes at least some form of computer readable media. Computer readable media can be any available media that can be accessed by processing unit 1802 or other devices comprising the operating environment. By way of example, and not limitation, computer readable media can comprise computer storage media and communication media. Computer storage media includes volatile and nonvolatile, removable and non-removable media implemented in any method or technology for storage of information such as computer readable instructions, data structures, program modules or other data. Computer storage media includes, RAM, ROM, EEPROM, flash memory or other memory technology, CD-ROM, digital versatile disks (DVD) or other optical storage, magnetic cassettes, magnetic tape, magnetic disk storage or other magnetic storage devices, solid state storage, or any other tangible medium which can be used to store the desired information. Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media. A computer-readable device is a hardware device incorporating computer storage media.

The operating environment 1800 can be a single computer operating in a networked environment using logical connections to one or more remote computers. The remote computer can be a personal computer, a server, a router, a network PC, a peer device or other common network node, and typically includes many or all of the elements described above as well as others not so mentioned. The logical connections can include any method supported by available communications media. Such networking environments are commonplace in offices, enterprise-wide computer networks, intranets and the Internet.

In some embodiments, the components described herein comprise such modules or instructions executable by a computer system that can be stored on computer storage medium and other tangible mediums and transmitted in communication media. Computer storage media includes volatile and non-volatile, removable and non-removable media implemented in any method or technology for storage of information such as computer readable instructions, data structures, program modules, or other data. Combinations of any of the above should also be included within the scope of readable media. In some embodiments, computer system is part of a network that stores data in remote storage media for use by the computer system.

In light of the foregoing, it should be appreciated that the present technology is able to track a change in focal spot position throughout successive image captures using one or more artificial targets. For example, the artificial targets may be captured in an initial image associated with gain map generation, as well as in subsequent images to which the gain map is applied. Following application of the gain map to a subsequent image, a shift in the artificial targets from a first position in the gain map to a second position in the subsequent image may be identified, where the shift corresponds to a change in focal spot position from the capture of the initial image to the capture of the subsequent image. Based on the identified shift, a last image captured (e.g., the normalized subsequent image) may be adjusted to correct for the change in order to remove any artifacts induced by the change. For example, the normalized subsequent image may be adjusted according to a same magnitude but opposite direction as the identified shift. Additionally or alternatively, a position of the focal spot may be physically corrected to reverse the change in focal spot position for subsequent imaging to prevent induction of artifacts in the subsequent imaging.

The embodiments described herein may be employed using software, hardware, or a combination of software and hardware to implement and perform the systems and methods disclosed herein. Although specific devices have been recited throughout the disclosure as performing specific functions, one of skill in the art will appreciate that these devices are provided for illustrative purposes, and other devices may be employed to perform the functionality disclosed herein without departing from the scope of the disclosure.

This disclosure describes some embodiments of the present technology with reference to the accompanying drawings, in which only some of the possible embodiments were shown. Other aspects may, however, be embodied in many different forms and should not be construed as limited to the embodiments set forth herein. Rather, these embodiments were provided so that this disclosure was thorough and complete and fully conveyed the scope of the possible embodiments to those skilled in the art. Further, as used herein and in the claims, the phrase "at least one of element A, element B, or element C" is intended to convey any of: element A, element B, element C, elements A and B, elements A and C, elements B and C, and elements A, B, and C.

Although specific embodiments are described herein, the scope of the technology is not limited to those specific embodiments. One skilled in the art will recognize other embodiments or improvements that are within the scope and spirit of the present technology. Therefore, the specific structure, acts, or media are disclosed only as illustrative embodiments. The scope of the technology is defined by the following claims and any equivalents therein.

What is claimed is:

1. A method for tracking a position of a focal spot of an x-ray tube, the method comprising:
   receiving an initial image from an image capturing system comprising the x-ray tube, the initial image including an artificial target at a first position in the initial image;
   generating a gain map based on the initial image;
   receiving a subsequent image from the image capturing system, the subsequent image including the artificial target;
   applying the gain map to the subsequent image to generate a normalized subsequent image; and
   identifying a shift of the artificial target from the first position in the initial image to a second position in the normalized subsequent image, the shift corresponding to a change in the position of the focal spot from capture of the initial image to capture of the subsequent image.

2. The method of claim 1, wherein identifying the shift comprises:
   generating a profile plot along a line intersecting the artificial target in a region of the normalized subsequent image, the profile plot including pixel intensity values for a predefined range of pixels in the region along a direction of the line;
   within the predefined range of pixels, identifying a first pixel having a local maximum pixel intensity value and a second pixel having a local minimum pixel intensity value; and
   determining a pixel distance between the first pixel and the second pixel.

3. The method of claim 2, further comprising:
   adjusting the normalized subsequent image based on the pixel distance.

4. The method of claim 2, further comprising:
   adjusting the gain map based on the pixel distance; and
   reapplying the gain map to the subsequent image.

5. The method of claim 2, further comprising:
   converting the pixel distance to a focal spot shift vector representing the change in the position of the focal spot in the direction of the line; and
   generating a control signal based on the focal spot shift vector for transmission to an apparatus that is capable of controlling dimensions of an electron beam received at an anode of the x-ray tube, wherein the dimensions of the electron beam affect the position of the focal spot on the anode, and the control signal causes the apparatus to adjust the dimensions of the electron beam to reverse the change in the position of the focal spot in the direction of the line.

6. The method of claim 2, further comprising:
   determining a median pixel intensity value for the predefined range of pixels;
   identifying the first pixel having the local maximum pixel intensity value based on a determination that a pixel intensity value of the first pixel is greater than the median pixel intensity value by at least a threshold value; and
   identifying the second pixel having the local minimum pixel intensity value based on a determination that a pixel intensity value of the second pixel is less than the median pixel intensity value by at least a threshold value.

7. The method of claim 1, wherein the artificial target is arranged substantially parallel to an x-axis of a detector, and identifying the shift of the artificial target comprises identifying the shift from the first position to the second position in a direction parallel to a y-axis of the detector, the shift corresponding to the change in the position of the focal spot in the direction parallel to the y-axis of the detector.

8. The method of claim 1, wherein the artificial target is arranged substantially parallel to a y-axis of a detector, and identifying the shift of the artificial target comprises identifying the shift from the first position to the second position in a direction parallel to an x-axis of the detector, the shift corresponding to the change in the position of the focal spot in the direction parallel to the x-axis of the detector.

9. The method of claim 1, wherein:
   the initial image and the subsequent image include at least two artificial targets;
   a first artificial target of the at least two artificial targets is arranged in a first direction and a second artificial target of the at least two artificial targets is arranged in a second direction, and
   the method further comprises:
      identifying a shift of the first artificial target from a first position in the initial image to a second position in the normalized subsequent image, the shift corresponding to a change in the position of the focal spot in the second direction; and
      identifying a shift of the second artificial target from a first position in the initial image to a second position in the normalized subsequent image, the shift corresponding to a change in the position of the focal spot in the first direction.

10. The method of claim 9, further comprising:
    generating a profile plot along a line in the second direction that intersects the first artificial target in a region of the normalized subsequent image, the profile plot including pixel intensity values for a predefined range of pixels in the region along the second direction of the line;
    within the predefined range of pixels, identifying a first pixel having a local maximum pixel intensity value and a second pixel having a local minimum pixel intensity value;
    determining a pixel distance between the first pixel and the second pixel in the second direction; and
    converting the pixel distance to a second direction focal spot shift vector representing the change in the position of the focal spot in the second direction.

11. The method of claim 10, further comprising:
generating a profile plot along a line in the first direction that intersects the second artificial target in a region of the normalized subsequent image, the profile plot including pixel intensity values for a predefined range of pixels in the region along the first direction of the line;
within the predefined range of pixels, identifying a first pixel having a local maximum pixel intensity value and a second pixel having a local minimum pixel intensity value;
determining a pixel distance between the first pixel and the second pixel in the first direction; and
converting the pixel distance to a first direction focal spot shift vector representing the change in the position of the focal spot in the first direction.

12. The method of claim 11, further comprising:
determining a resultant focal spot shift vector based on the first direction focal spot shift vector and the second direction focal spot shift vector;
determining an angle associated with the resultant focal spot shift vector based on the first direction focal spot shift vector and the second direction focal spot shift vector; and
generating a control signal based on the angle for transmission to an apparatus that is capable of controlling dimensions of an electron beam received at an anode of the x-ray tube, wherein the dimensions of the electron beam affect the position of the focal spot on the anode, and the control signal causes the apparatus to adjust the dimensions of the electron beam to reverse the change in the position of the focal spot in the first direction and the second direction.

13. A system for tracking and adjusting a position of a focal spot of an x-ray tube, the system comprising:
an image capturing system comprising at least the x-ray tube and a detector;
an artificial target;
an apparatus that is capable of controlling dimensions of an electron beam received at an anode of the x-ray tube, wherein the dimensions of the electron beam affect the position of the focal spot on the anode;
an image processing system communicatively coupled to the image capturing system and the apparatus, the image processing system including at least:
a processor; and
a memory coupled to the processor and storing instructions, that when executed by the processor, cause the processor to:
receive, from the image capturing system, an initial image including the artificial target at a first position in the initial image;
generate a gain map based on the initial image;
receive, from the image capturing system, a subsequent image including the artificial target;
apply the gain map to the subsequent image to generate a normalized subsequent image;
identify a shift of the artificial target from the first position in the initial image to a second position in the normalized subsequent image, the shift corresponding to a change in the position of the focal spot from capture of the initial image to capture of the subsequent image;
generate a control signal to cause the apparatus to adjust the dimensions of the electron beam to reverse the change in the position of the focal spot; and
transmit the control signal to the apparatus.

14. The system of claim 13, wherein the artificial target is comprised of a metal or a material that highly attenuates x-rays.

15. The system of claim 13, wherein the artificial target is arranged substantially parallel to one of an x-axis or a y-axis of the detector.

16. The system of claim 13, the system comprising at least two artificial targets, wherein a first artificial target is arranged substantially parallel to an x-axis of the detector, and a second artificial target is arranged substantially parallel to a y-axis of the detector.

17. The system of claim 13, wherein the artificial target is a mesh object that is arranged to extend along an x-axis and a y-axis across an entirety of a window of the x-ray tube.

18. The system of claim 13, wherein the apparatus comprises at least a first magnet configured to deflect the electron beam in one direction and a second magnet configured to deflect the electron beam in an opposite direction, and the control signal causes the first magnet to deflect the electron beam in the one direction based on a strength of the first magnet as a function of the identified shift, and the second magnet to deflect the electron beam in the opposite direction based on a strength of the second magnet as a function of the identified shift.

19. The system of claim 13, wherein the apparatus comprises two pairs of electrodes configured to generate an electrical field that controls the dimensions of the electron beam, the two pairs of electrodes including a first pair of electrodes configured to deflect the electron beam in one direction based on a strength of the electrical field as a function of the identified shift, and a second pair of electrodes configured to deflect the electron beam in an opposite direction based on the strength of the electrical field as a function of the identified shift.

20. A calibration method to enable a position of a focal spot of an x-ray tube to be tracked during patient imaging, the method comprising:
receiving an initial image and a subsequent image from an image capturing system comprising the x-ray tube, the initial image including a mesh object artificial target at a first position in the initial image and the subsequent image including the mesh object artificial target at a second position in the subsequent image;
generating a gain map from the initial image and applying the gain map to the subsequent image to generate a normalized subsequent image;
for a plurality of regions across an x-axis and a y-axis in the normalized subsequent image, identifying a shift of the mesh object artificial target within the respective region from the first position to the second position, wherein the respective region corresponds to one of x- and y-axis pixel coordinates of the image;
determining a maximum shift across the x-axis and the y-axis, the maximum shift representing a change in a position of the focal spot;
identifying at least one of an x-axis pixel coordinate and a y-axis pixel coordinate where an artificial target is to be positioned for patient imaging;
deriving a ratio of the maximum shift to a shift identified at a region from the plurality of regions corresponding to the at least one of the x-axis pixel coordinate and the y-axis pixel coordinate where the artificial target is to be positioned for patient imaging; and applying the ratio to an identified shift of the artificial target in a pair of subsequently captured patient images to determine the change in the position of the focal spot.

* * * * *